(12) United States Patent
Hefeneider et al.

(10) Patent No.: US 7,132,399 B2
(45) Date of Patent: Nov. 7, 2006

(54) MAMMALIAN CELL SURFACE DNA RECEPTOR

(75) Inventors: Steven Hefeneider, Portland, OR (US); Robert Bennett, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 345 days.

(21) Appl. No.: 10/619,992

(22) Filed: Jul. 15, 2003

(65) Prior Publication Data

US 2005/0239163 A1   Oct. 27, 2005

Related U.S. Application Data

(62) Division of application No. 09/921,099, filed on Aug. 1, 2001, now Pat. No. 6,602,707.

(60) Provisional application No. 60/222,624, filed on Aug. 1, 2000.

(51) Int. Cl.
*A61K 38/17* (2006.01)
*C07K 14/435* (2006.01)

(52) U.S. Cl. ........................ 514/12; 530/350

(58) Field of Classification Search ............... None
See application file for complete search history.

(56) References Cited

FOREIGN PATENT DOCUMENTS

WO    WO 01/34628    5/2001

OTHER PUBLICATIONS

Siess, et al. A human gene coding for a membrane-associated nucleic acid-binding protein. J. Biol. Chem. 275:33655-33662, 2000.*
Fantin et al. Characterization of insulin receptor substrate 4 in human embryonic kidney 293 cells. J. Biol. Chem. 273:10726-10732, 1998.*
Hefeneider et al. Identification of a cell-surface DNA receptor and its association with systemic lupus erythematosus. J. Invest. Dermatol. 94:79S-84S, 1990.*
U.S. Appl. No. 60/222,624, filed Aug. 1, 2000, Siess et al.
Bennett et al., "DNA Binding to Human Leukocytes," Journal of Clinical Invest. 76:2182-2190 (1985).
Bennett et al., "Anti-DNA Antibodies React with DNA Expressed on the Surface of Monocytes and B Lymphocytes," The Journal of Rheumatology 13(4):679-685 (1986).
Bennett et al., "DNA Receptor Dysfunction in System Lupus Erythematosus And Kindred Disorders," Journal of Experimental Medicine 166:850-863 (1987).
Bennett et al., "Autoimmunity to a 28-30 kD cell membrane DNA binding protein: occurrence in selected sera from patients with SLE and mixed connective tissue disease (MCTD)," Clinical and Experimental Immunology 86(3):374-379 (1991).
Bennett et al., "Idiotypic Mimicry of a cell surface DNA receptor: evidence for anti-DNA antibodies being a subset of anti-anti-DNA receptor antibodies," Clinical and Experimental Immunology 90(3):428-433 (1992).
Bennett et al., "As Nature Intended? The Uptake of DNA and Oligonucleotides by Eukaryotic Cells," Antisense Research and Development 3(3):235-241 (1993).
Bilton et al., "New treatment in adult cystic fibrosis," Journal of the Royal Society of Medicine 90:2-5 (1997).
Bush et al., "Early Treatment With Dornase Alfa in Cystic Fibrosis: What Are the Issues?," Pediatric Pulmonology 25:79-82 (1998).
Cramer et al., "The role of dornase alfa in the treatment of cystic fibrosis," The Annals of Pharmacotherapy 30(6):656-661 (1996).
Davis et al., "Cystic Fibrosis," American Journal of Respiratory & Critical Care Medicine 154(5):1229-1256 (1996).
Doring G. "Anit-Inflammatory Therapy," Pediatric Pulmonology, Supplement 16:271-272 (1997).
Eigen et al., "A multicenter study of alternate-day prednisone therapy in patients with cystic fibrosis," The Journal of Pediatrics 126(4):515-523 (1995).
Emlen et al., "Hepatic Binding of DNA is Mediated by a Receptor on Nonparenchymal Cells," American Journa of Pathology 133(1):54-60 (1988).
Gabor & Bennett, 1984, "*Biochem Biophys. Res. Commun.*" 122:1034-1039.
Gasparro et al., "Cell Membrane DNA: A new target for Psoralen Photoadduct Formation," Photochemistry and Photobiology 52(2):315-321 (1990).
Gene Bank Accession No. 2496825.
Gene Bank Accession No. 3878739.
Gene Bank Accession No. 3879246.
Gene Bank Accession No. 422756.
Gene Bank Accession No. 5032071.
Gene Bank Accession No. 951276.
Gene Bank Accession No. L42133.
Gene Bank Accession No. U13397.
Gene Bank Accession No. U62896.
Gene Bank Accession No. X79066.

(Continued)

*Primary Examiner*—Ruixiang Li
(74) *Attorney, Agent, or Firm*—Jagtiani + Guttag

(57) ABSTRACT

The present invention relates to novel mammalian DNA-R proteins and genes that encode such proteins. The invention is directed toward the isolation and characterization of mammalian DNA-R proteins. The invention specifically provides isolated complementary DNA copies of mRNA corresponding to rat and human homologues of a mammalian DNA-R gene. Also provided are recombinant expression constructs capable of expressing the mammalian DNA-R genes of the invention in cultures of transformed prokaryotic and eukaryotic cells, as well as such cultures of transformed cells that synthesize the mammalian catecholamine receptor proteins encoded therein. The invention also provides methods for screening compounds in vitro that are capable of binding to the mammalian DNA-R proteins of the invention, and further characterizing the binding properties of such compounds in comparison with known DNA-R agonists and antagonists. Improved methods of pharmacological screening are provided thereby.

3 Claims, 27 Drawing Sheets

OTHER PUBLICATIONS

Yakov Gluzman. "SV40-Transformed Simian Cells Support the Replication of Early SV40 Mutants," Cell 23:175-182 (1981).

Hefeneider et al., "Identification of a Cell-Surface DNA Receptor and Its Association with Systemic Lupus Erythematosus," The Journal of Investigative Dermatology 94(6):79S-84S (1990).

Hefeneider et al., "DNA Binding to Mouse Cells is Mediated by Cell-Surface Molecules: The Role of These DNA-Binding Molecules as Target Antigens in Murine Lupus," Lupus 1:167-173 (1992).

Hefeneider et al., "Nucleosomes and DNA Bind to Specific Cell-Surface Molecules on Murine Cells and Induce Cytokine Production," Clinical Immunology and Immunopathology 63(3):245-251 (1992).

Hefeneider et al., "The cloning and sequencing of a human 130 kDa cell surface DNA binding protein reactive with lupus antibodies," Arthritis & Rheumatism 39(9):S35 (1996) [XP002205492].

Hegde et al. 2000 "*Assessment of Gene Expression Patterns in a Model of Colon Tumor*", XP002205495.

Henry et al., "Airway Inflammation After Treatment With Aerosolized Deoxyribonuclease in Cystic Fibrosis," Pediatric Pulmonology 26:97-100 (1998).

International Search Report from PCT/US01/24351 mailed Aug. 23, 2002.

Konstan et al., "Therapies aimed at airway inflammation in cystic fibrosis," Clinics in Chest Medicine 19(3):505-513 (1998).

Konstan et al., "Effect of high-dose Ibuprofen in patients with Cystic Fibrosis," The New England Journal of Medicine 332:848-854 (1995).

Lerner et al., "Membrane-Associated DNA in the Cytoplasm of Diploid Human Lymphocytes," Porc. Nat. Acad. Sci. 68(6):1212-1216 (1971).

Meinke et al., "Reassociation and Dissociation of Cytoplasmic Membrane-associated DNA," Journal of Molecular Biology 86(4):757-773 (1974).

Pancer et al., "Immunogenicity and Characterization of Supernatant DNA Released by Murine Spleen Cells," The Journal of Immunology 127(1):98-104 (1981).

Reid et al., "Cytoplasmic and Cell Surface Deoxyribonucleic Acids with Consideration of Their Origin," International Review of Cytology 60:27-52 (1979).

Schwartz et al., CpG Motifs in Bacterial DNA Cause Inflammation in the Lower Respiratory Tract, The Journal of Clinical Investigation 100(1):68-73 (1997).

Siess et al., "Expression of a candidate cell-surface DNA receptor gene," Arthritis & Rheumatism 41(9):S143 (1998) [XP002205491].

Siess et al., 2000 "*Journal of Biological Chemistry*", XP002205493 275(43):33655-33662.

Strausberg, 2000, "*National Institutes of Health, Mammalian Gene Collection*", XP002205494.

Sudar et al., "Localization and Internalization of Cell Surface DNA in Macrophages," Cellular and Molecular Biology 32(1):87-91 (1986).

Tang, et al., 2001 "*Database Geneseq*" Database Accession No. AAI59510, XP002205808.

Tang, et al., 2001 "*Database Geneseq*" Database Accession No. AAI59511, XP002205809.

Tang, et al., 2001 "*Database Geneseq*" Database Accession No. AAI61296, XP002205812.

Tang, et al., 2001 "*Database Geneseq*" Database Accession No. AAI61297, XP002205813.

Tang, et al., 2001 "*Database Geneseq*" Database Accession No. AAM40354, XP002205810.

Tang, et al., 2001 "*Database Geneseq*" Database Accession No. AAM40355, XP002205811.

Tang, et al., 2001 "*Database Geneseq*" Database Accession No. AAM42140, XP002205814.

Tang, et al., 2001 "*Database Geneseq*" Database Accession No. AAM42141, XP002205815.

Tanigami et al., 2000 "*NEDO Human cDNA Sequencing Project*", XP002205496.

Young et al., "Efficient isolation of genes by using antibody probes," Proc. Natl. Acad. Sci. 80:1194-1198 (1983).

* cited by examiner

A. C3HC3D Ring finger homologies

```
MNAB                              TEFLSCPIC----YNEFDENVHKPISLGCSHTVCKTCLNKLHRKA------CPFDQTAIN       58
H.sapiens ARD1                    VKVLEGVCEDVFSL--QGDKVPRLLLCGHTVCHDCLTRLPLHGR--AIRCPFDRQVTD       80
H.sapiens CART1                   KRRLLCPLCGKPMREPVQVST------CGHRFCDTCLQEFLSEG---VFKCPEDQLPLD     62
H.sapiens SBBIO3                  DEDLICPICSGVLEEPVQAPH------CEHAFCNACITQWFSQQ---Q-TCPVDRSVVT     61
C.elegans cDNA EST 3879246        --YSECLVC----YQKFDENTRIPRVMDCGHTLCDFCINQIVKMAGCYSATCPFDRVRI-    182
C.elegans 25.8KD protein          -EWRSCFICTMEY SRTDKNLH-PIILNCGHNLCRSCINKL---TGNGIVKCPFDR-----   199
C.elegans cDNA EST 3878739        QEVLCCSICNRHFNE----TFLPVSLICGHVICRKCAEKPENQTK----PCPHDDWKTT-    61
C3HC3D motif                      -----C--C---------------------C--H---C-----------C----D----
```

B. C3H Zinc finger homologies

```
MNAB                  ETPQPQPNSKYKTSMCRDLRQQGGCPRGTNCTFAHSQEELEKYRLRNK      448
C. elegans    PIE-1   ------HTEYKTRLCDAFRREGYCPYNDNCTYAHGQDELRVPRRRQE---    136
D.melanogaster DTIS11 ----QPMNTSRYKTELCRPFEEAGECKYGEKCQFAHGSHEL--------    166
H.sapiens     TIS11B  ----SSRYKTELCRPFEENGACKYGDKCQFAHGIHEL-----------    181
S.cerevisiae  CTH1    QLPQLVNKTLYKTELCESFTIKGYCKYGNKCQFAHGLNELK---------    235
C3H    motif          -------------YKTELC---------C-----------H--------
```

Fig. 4

SEQUENCE LISTING

<160> NUMBER OF SEQ ID NOS: 21

<210> SEQ ID NO 1
<211> LENGTH: 4351
<212> TYPE: DNA
<213> ORGANISM: Homo sapiens
<220> FEATURE:
<221> NAME/KEY: CDS
<222> LOCATION: (602)..(4174)

<400> SEQUENCE: 1

```
agccaagtct tgtcagagat ttcctctttc aggtggcaaa gctgttttct tcacacttga      60
gtctctacaa tattgtttgg atcagtagtt tccaaagttc attaactcct ggccatactt     120
tattatgttt tggggtactg gttatccaag ggaaacactt ttttaaacaa caaaacaaaa     180
aaaccgccca gcagtccaaa gtaatttgtt ttcctaaaaa tggaatatgg aaagttaatt     240
tgcttgtttg atgtggtcgt tgagaaaaat acataaaagc tttgatgttt attatgtgag     300
caaccaatat aaatacagtt tagttgaaag gaacactatt aagtattgt ttccaggcag      360 aatttcagaa atgtaattaa ttcagcaaat aggttttta aaaagacat ccaaaggtta       420 taaaattatt tagaagtatt ttaggtctga agctgtaata gttgacttaa gcaattaact    480
cttcaaaggt gaatgatgaa tatgtggtta attcatactt ttgtccattt ctagcttaca    540
aaacactaca cagcaaaata atgatctgct agactgctaa cccgagcatc cagcttccac    600
```

```
a atg cct gtg cag gca gct caa tgg aca gaa ttt ctg tcc tgt cca atc        649
  Met Pro Val Gln Ala Ala Gln Trp Thr Glu Phe Leu Ser Cys Pro Ile
  1               5                  10                 15 tgc tat aat gaa ttt gat gag aat gtg cac aaa ccc atc agt tta ggt         697
Cys Tyr Asn Glu Phe Asp Glu Asn Val His Lys Pro Ile Ser Leu Gly
            20                  25                  30 tgt tca cac act gtt tgc aag acc tgc ttg aat aaa ctt cat cga aaa         745
Cys Ser His Thr Val Cys Lys Thr Cys Leu Asn Lys Leu His Arg Lys
        35                  40                  45 gct tgt cct ttt gac cag act gcc atc aac aca gat att gat gta ctt         793
Ala Cys Pro Phe Asp Gln Thr Ala Ile Asn Thr Asp Ile Asp Val Leu
    50                  55                  60 cct gtc aac ttc gca ctt ctc cag tta gtt gga gcc cag gta cca gat         841
Pro Val Asn Phe Ala Leu Leu Gln Leu Val Gly Ala Gln Val Pro Asp
65                  70                  75                  80 cat cag tca att aag tta agt aat cta ggt gag aat aaa cac tat gag         889
His Gln Ser Ile Lys Leu Ser Asn Leu Gly Glu Asn Lys His Tyr Glu
                85                  90                  95 gtt gca aag aaa tgc gtt gag gat ttg gca ctc tac tta aaa cca cta         937
Val Ala Lys Lys Cys Val Glu Asp Leu Ala Leu Tyr Leu Lys Pro Leu
            100                 105                 110 agt gga ggt aaa ggt gta gct agc ttg aac cag agt gca ctg agc cgt         985
Ser Gly Gly Lys Gly Val Ala Ser Leu Asn Gln Ser Ala Leu Ser Arg
        115                 120                 125 cca atg caa agg aaa ctg gtg aca ctt gta aac tgt caa ctg gtg gag        1033
Pro Met Gln Arg Lys Leu Val Thr Leu Val Asn Cys Gln Leu Val Glu
    130                 135                 140 gaa gaa ggt cgt gta aga gcc atg cga gca gct cgt tcc ctt gga gaa        1081
Glu Glu Gly Arg Val Arg Ala Met Arg Ala Ala Arg Ser Leu Gly Glu
145                 150                 155                 160 aga act gta aca gaa ctg ata tta cag cac cag aac cct cag cag ttg        1129
Arg Thr Val Thr Glu Leu Ile Leu Gln His Gln Asn Pro Gln Gln Leu
                165                 170                 175
```

-continued

| | |
|---|---|
| tct gcc aat cta tgg gcc gct gtc agg gct cga gga tgc cag ttt tta<br>Ser Ala Asn Leu Trp Ala Ala Val Arg Ala Arg Gly Cys Gln Phe Leu<br>             180                        185                       190 | 1177 |
| ggg cca gct atg caa gaa gag gcc ttg aag ctg gtg tta ctg gca tta<br>Gly Pro Ala Met Gln Glu Glu Ala Leu Lys Leu Val Leu Leu Ala Leu<br>         195                       200                       205 | 1225 |
| gaa gat ggt tct gcc ctc tca agg aaa gtt ctg gta ctt ttt gtt gtg<br>Glu Asp Gly Ser Ala Leu Ser Arg Lys Val Leu Val Leu Phe Val Val<br>210                       215                       220 | 1273 |
| cag aga cta gaa cca aga ttt cct cag gca tca aaa aca agt att ggt<br>Gln Arg Leu Glu Pro Arg Phe Pro Gln Ala Ser Lys Thr Ser Ile Gly<br>225                       230                       235                       240 | 1321 |
| cat gtt gtg caa cta ctg tat cga gct tct tgt ttt aag gtt acc aaa<br>His Val Val Gln Leu Leu Tyr Arg Ala Ser Cys Phe Lys Val Thr Lys<br>             245                       250                       255 | 1369 |
| aga gat gaa gac tct tcc cta atg cag ctg aag gag gaa ttt cgg agt<br>Arg Asp Glu Asp Ser Ser Leu Met Gln Leu Lys Glu Glu Phe Arg Ser<br>                  260                       265                       270 | 1417 |
| tat gaa gca tta cgc aga gaa cat gat gcc caa att gtt cat att gcc<br>Tyr Glu Ala Leu Arg Arg Glu His Asp Ala Gln Ile Val His Ile Ala<br>             275                       280                       285 | 1465 |
| atg gaa gca gga ctc cgt att tca cct gaa cag tgg tcc tct ctt ttg<br>Met Glu Ala Gly Leu Arg Ile Ser Pro Glu Gln Trp Ser Ser Leu Leu<br>290                       295                       300 | 1513 |
| tat ggt gat ttg gct cat aaa tca cac atg cag tct atc att gat aag<br>Tyr Gly Asp Leu Ala His Lys Ser His Met Gln Ser Ile Ile Asp Lys<br>305                       310                       315                       320 | 1561 |
| cta cag tct cca gag tca ttt gca aag agt gtc cag gaa ttg aca att<br>Leu Gln Ser Pro Glu Ser Phe Ala Lys Ser Val Gln Glu Leu Thr Ile<br>                  325                       330                       335 | 1609 |
| gtt ttg caa cga aca ggt gac cca gct aac tta aat aga ctg agg cct<br>Val Leu Gln Arg Thr Gly Asp Pro Ala Asn Leu Asn Arg Leu Arg Pro<br>             340                       345                       350 | 1657 |
| cat tta gag ctt ctt gca aac ata gac cct aat cca gac gct gtt tca<br>His Leu Glu Leu Leu Ala Asn Ile Asp Pro Asn Pro Asp Ala Val Ser<br>                  355                       360                       365 | 1705 |
| cca act tgg gag cag ctg gaa aat gca atg gta gct gtt aaa aca gta<br>Pro Thr Trp Glu Gln Leu Glu Asn Ala Met Val Ala Val Lys Thr Val<br>         370                       375                       380 | 1753 |
| gtt cat ggc ctt gtg gac ttc ata caa aat tat agt aga aaa ggc cat<br>Val His Gly Leu Val Asp Phe Ile Gln Asn Tyr Ser Arg Lys Gly His<br>385                       390                       395                       400 | 1801 |
| gag acc cct cag cct cag cca aac agc aaa tac aag act agc atg tgc<br>Glu Thr Pro Gln Pro Gln Pro Asn Ser Lys Tyr Lys Thr Ser Met Cys<br>                  405                       410                       415 | 1849 |
| cga gat ttg cga cag cag ggg ggt tgt cca cga gga aca aat tgt aca<br>Arg Asp Leu Arg Gln Gln Gly Gly Cys Pro Arg Gly Thr Asn Cys Thr<br>             420                       425                       430 | 1897 |
| ttt gcc cat tct cag gaa gag ctt gaa aag tat cga tta agg aac aaa<br>Phe Ala His Ser Gln Glu Glu Leu Glu Lys Tyr Arg Leu Arg Asn Lys<br>                  435                       440                       445 | 1945 |
| aag atc aat gcc act gta aga acg ttt cct ctt cta aat aaa gtt ggt<br>Lys Ile Asn Ala Thr Val Arg Thr Phe Pro Leu Leu Asn Lys Val Gly<br>         450                       455                       460 | 1993 |
| gta aac aac act gtc aca acc aca gcc gga aat gtc att tct gtc ata<br>Val Asn Asn Thr Val Thr Thr Thr Ala Gly Asn Val Ile Ser Val Ile<br>465                       470                       475                       480 | 2041 |
| gga agt act gaa aca aca ggg aaa att gtt cca agt aca aac gga att<br>Gly Ser Thr Glu Thr Thr Gly Lys Ile Val Pro Ser Thr Asn Gly Ile<br>                  485                       490                       495 | 2089 |

| | | |
|---|---|---|
| tca aat gca gaa aac agt gtt tcc cag cta atc tca cgt agt act gac<br>Ser Asn Ala Glu Asn Ser Val Ser Gln Leu Ile Ser Arg Ser Thr Asp<br>500 505 510 | | 2137 |
| agt acc tta aga gct ctg gag acc gtg aag aaa gtg gga aag gtt ggc<br>Ser Thr Leu Arg Ala Leu Glu Thr Val Lys Lys Val Gly Lys Val Gly<br>515 520 525 | | 2185 |
| gct aat ggt cag aat gct gct ggg ccc tct gca gat tct gta act gaa<br>Ala Asn Gly Gln Asn Ala Ala Gly Pro Ser Ala Asp Ser Val Thr Glu<br>530 535 540 | | 2233 |
| aat aaa att ggt tct cca ccc aag act cct gta agt aat gta gca gct<br>Asn Lys Ile Gly Ser Pro Pro Lys Thr Pro Val Ser Asn Val Ala Ala<br>545 550 555 560 | | 2281 |
| acc tca gct ggg ccc tct aat gtt gga aca gag ctg aat tct gtg cct<br>Thr Ser Ala Gly Pro Ser Asn Val Gly Thr Glu Leu Asn Ser Val Pro<br>565 570 575 | | 2329 |
| caa aaa tcc agc cca ttt cta act aga gta cca gta tat cct ccg cat<br>Gln Lys Ser Ser Pro Phe Leu Thr Arg Val Pro Val Tyr Pro Pro His<br>580 585 590 | | 2377 |
| tct gaa aac att cag tat ttt caa gat cca agg act cag ata ccc ttt<br>Ser Glu Asn Ile Gln Tyr Phe Gln Asp Pro Arg Thr Gln Ile Pro Phe<br>595 600 605 | | 2425 |
| gaa gtc cca cag tac cca cag aca gga tac tat cca cca cct cca acg<br>Glu Val Pro Gln Tyr Pro Gln Thr Gly Tyr Tyr Pro Pro Pro Thr<br>610 615 620 | | 2473 |
| gta cca gct ggt gtg gct ccc tgt gtt cct cgc ttt gtg agg tcc aat<br>Val Pro Ala Gly Val Ala Pro Cys Val Pro Arg Phe Val Arg Ser Asn<br>625 630 635 640 | | 2521 |
| aac gtt cca gag tcc tcc ctc cca cct gct tcc atg cca tat gcc gat<br>Asn Val Pro Glu Ser Ser Leu Pro Pro Ala Ser Met Pro Tyr Ala Asp<br>645 650 655 | | 2569 |
| cat tac agt aca ttt tcc cct cga gat cga atg aat tct tct cct tac<br>His Tyr Ser Thr Phe Ser Pro Arg Asp Arg Met Asn Ser Ser Pro Tyr<br>660 665 670 | | 2617 |
| cag cct cct cct ccg cag ccg tat gga cca gtt cct cca gta cct tct<br>Gln Pro Pro Pro Pro Gln Pro Tyr Gly Pro Val Pro Pro Val Pro Ser<br>675 680 685 | | 2665 |
| gga atg tat gct cct gtg tac gac agc agg cgc atc tgg cgc cca cct<br>Gly Met Tyr Ala Pro Val Tyr Asp Ser Arg Arg Ile Trp Arg Pro Pro<br>690 695 700 | | 2713 |
| atg tac caa cga gat gac att att aga agc aat tct tta cct cca atg<br>Met Tyr Gln Arg Asp Asp Ile Ile Arg Ser Asn Ser Leu Pro Pro Met<br>705 710 715 720 | | 2761 |
| gat gtg atg cac tca tct gtc tat cag aca tct ttg cgg gaa aga tat<br>Asp Val Met His Ser Ser Val Tyr Gln Thr Ser Leu Arg Glu Arg Tyr<br>725 730 735 | | 2809 |
| aac tca tta gat gga tat tat tcg gtg gct tgt cag cca cca agt gag<br>Asn Ser Leu Asp Gly Tyr Tyr Ser Val Ala Cys Gln Pro Pro Ser Glu<br>740 745 750 | | 2857 |
| cca agg aca act gtg cct tta cca agg gaa cct tgt ggt cat ttg aag<br>Pro Arg Thr Thr Val Pro Leu Pro Arg Glu Pro Cys Gly His Leu Lys<br>755 760 765 | | 2905 |
| acc agt tgc gag gag cag ata aga aga aag cca gat cag tgg gca cag<br>Thr Ser Cys Glu Glu Gln Ile Arg Arg Lys Pro Asp Gln Trp Ala Gln<br>770 775 780 | | 2953 |
| tac cac act cag aaa gca cct ctt gtc tct tca act ctt cct gtg gca<br>Tyr His Thr Gln Lys Ala Pro Leu Val Ser Ser Thr Leu Pro Val Ala<br>785 790 795 800 | | 3001 |
| aca cag tca cca aca cca cct tct cct ctg ttc agt gta gac ttt cgt<br>Thr Gln Ser Pro Thr Pro Pro Ser Pro Leu Phe Ser Val Asp Phe Arg | | 3049 |

|                                                                                                     |      |
|-----------------------------------------------------------------------------------------------------|------|
| gcg gat ttc tca gag agt gtg agt ggt aca aaa ttt gaa gaa gat cat<br>Ala Asp Phe Ser Glu Ser Val Ser Gly Thr Lys Phe Glu Glu Asp His<br>      820                    825                  830 | 3097 |
| ctt tcc cat tat tct ccc tgg tct tgt ggc acc ata ggc tcc tgt ata<br>Leu Ser His Tyr Ser Pro Trp Ser Cys Gly Thr Ile Gly Ser Cys Ile<br>    835                  840                845 | 3145 |
| aat gcc att gat tca gag ccc aaa gat gtc att gct aat tca aat gct<br>Asn Ala Ile Asp Ser Glu Pro Lys Asp Val Ile Ala Asn Ser Asn Ala<br>850                  855                860 | 3193 |
| gtg tta atg gac ctg gac agt ggt gat gtt aag aga aga gta cat tta<br>Val Leu Met Asp Leu Asp Ser Gly Asp Val Lys Arg Arg Val His Leu<br>865                  870                875                880 | 3241 |
| ttt gaa acc cag aga agg aca aaa gaa gaa gat cca ata att ccc ttt<br>Phe Glu Thr Gln Arg Arg Thr Lys Glu Glu Asp Pro Ile Ile Pro Phe<br>                  885                890                895 | 3289 |
| agt gat gga ccc atc atc tca aaa tgg ggt gcg att tcc aga tct tcc<br>Ser Asp Gly Pro Ile Ile Ser Lys Trp Gly Ala Ile Ser Arg Ser Ser<br>    900                  905                910 | 3337 |
| cgt aca ggt tac cat acc aca gat cct gtc cag gcc act gct tcc caa<br>Arg Thr Gly Tyr His Thr Thr Asp Pro Val Gln Ala Thr Ala Ser Gln<br>               915                920                925 | 3385 |
| gga agt gcg act aag ccc atc agt gta tca gat tat gtc cct tat gtc<br>Gly Ser Ala Thr Lys Pro Ile Ser Val Ser Asp Tyr Val Pro Tyr Val<br>930                  935                940 | 3433 |
| aat gct gtt gat tca agg tgg agt tca tat ggc aac gag gcc aca tca<br>Asn Ala Val Asp Ser Arg Trp Ser Ser Tyr Gly Asn Glu Ala Thr Ser<br>945                  950                955                960 | 3481 |
| tca gca cac tat gtt gaa agg gac aga ttc att gtt act gat tta tct<br>Ser Ala His Tyr Val Glu Arg Asp Arg Phe Ile Val Thr Asp Leu Ser<br>               965                970                975 | 3529 |
| ggt cat aga aag cat tcc agt act ggg gac ctt ttg agc ctt gaa ctt<br>Gly His Arg Lys His Ser Ser Thr Gly Asp Leu Leu Ser Leu Glu Leu<br>    980                  985                990 | 3577 |
| cag cag gcc aag agc aac tca tta ctt ctt cag aga gag gcc aat gct<br>Gln Gln Ala Lys Ser Asn Ser Leu Leu Leu Gln Arg Glu Ala Asn Ala<br>               995               1000             1005 | 3625 |
| ttg gcc atg caa cag aag tgg aat tcc ctg gat gaa ggc cgt cac<br>Leu Ala Met Gln Gln Lys Trp Asn Ser Leu Asp Glu Gly Arg His<br>1010                  1015             1020 | 3670 |
| ctt acc tta aac ctt tta agc aag gaa att gaa cta aga aat gga<br>Leu Thr Leu Asn Leu Leu Ser Lys Glu Ile Glu Leu Arg Asn Gly<br>1025                  1030             1035 | 3715 |
| gag tta cag agt gat tat aca gaa gat gca aca gat act aaa cct<br>Glu Leu Gln Ser Asp Tyr Thr Glu Asp Ala Thr Asp Thr Lys Pro<br>1040                  1045             1050 | 3760 |
| gat agg gat atc gag tta gag ctt tca gca ctt gat act gat gaa<br>Asp Arg Asp Ile Glu Leu Glu Leu Ser Ala Leu Asp Thr Asp Glu<br>1055                  1060             1065 | 3805 |
| cct gat gga caa agt gaa cca att gaa gag atc ttg gac ata cag<br>Pro Asp Gly Gln Ser Glu Pro Ile Glu Glu Ile Leu Asp Ile Gln<br>1070                  1075             1080 | 3850 |
| ctt ggt atc agt tct caa aat gat cag ttg cta aat gga atg gca<br>Leu Gly Ile Ser Ser Gln Asn Asp Gln Leu Leu Asn Gly Met Ala<br>1085                  1090             1095 | 3895 |
| gtg gaa aat ggg cat cca gta cag cag cac caa aag gag cca cca<br>Val Glu Asn Gly His Pro Val Gln Gln His Gln Lys Glu Pro Pro<br>1100                  1105             1110 | 3940 |
| aag cag aag aaa cag agt tta ggt gaa gac cat gtg att ctg gag | 3985 |

| | | | | | | | | | | | |
|---|---|---|---|---|---|---|---|---|---|---|---|
| Lys | Gln | Lys | Lys | Gln | Ser | Leu | Gly | Glu | Asp | His | Val | Ile Leu Glu |
| 1115 | | | | 1120 | | | | | 1125 | | |

```
gag caa aaa aca att ctg ccg gta act tct tgc ttt agc cag cca       4030
Glu Gln Lys Thr Ile Leu Pro Val Thr Ser Cys Phe Ser Gln Pro
    1130            1135                1140 ctc cca gtg tct att agc aat gca agt tgc ctc ccc atc acc aca       4075
Leu Pro Val Ser Ile Ser Asn Ala Ser Cys Leu Pro Ile Thr Thr
    1145            1150                1155 tct gtc agt gct ggc aac ctc att ctg aaa act cat gtt atg tct       4120
Ser Val Ser Ala Gly Asn Leu Ile Leu Lys Thr His Val Met Ser
    1160            1165                1170 gaa gat aaa aac gac ttt tta aaa cct gtt gca aat ggg aag atg       4165
Glu Asp Lys Asn Asp Phe Leu Lys Pro Val Ala Asn Gly Lys Met
    1175            1180                1185 gtt aac agc tgaaaggagg ttcatctttc aaatttgtga ccacaccatg          4214
Val Asn Ser
    1190 gaagcattta cactagcttt ttatatatat aatatatatt ataatgta tatttttttt   4274 aaaaaaaaga tattactggg ggcatccatt tcctgtggac tctttgatac ttcaagccct 4334 cttgcattag cattatg                                                4351

<210> SEQ ID NO 2
<211> LENGTH: 1191
<212> TYPE: PRT
<213> ORGANISM: Homo sapiens

<400> SEQUENCE: 2

Met Pro Val Gln Ala Ala Gln Trp Thr Glu Phe Leu Ser Cys Pro Ile
1               5                   10                  15

Cys Tyr Asn Glu Phe Asp Glu Asn Val His Lys Pro Ile Ser Leu Gly
                20                  25                  30

Cys Ser His Thr Val Cys Lys Thr Cys Leu Asn Lys Leu His Arg Lys
            35                  40                  45

Ala Cys Pro Phe Asp Gln Thr Ala Ile Asn Thr Asp Ile Asp Val Leu
        50                  55                  60

Pro Val Asn Phe Ala Leu Leu Gln Leu Val Gly Ala Gln Val Pro Asp
65                  70                  75                  80

His Gln Ser Ile Lys Leu Ser Asn Leu Gly Glu Asn Lys His Tyr Glu
                85                  90                  95

Val Ala Lys Lys Cys Val Glu Asp Leu Ala Leu Tyr Leu Lys Pro Leu
                100                 105                 110

Ser Gly Gly Lys Gly Val Ala Ser Leu Asn Gln Ser Ala Leu Ser Arg
            115                 120                 125

Pro Met Gln Arg Lys Leu Val Thr Leu Val Asn Cys Gln Leu Val Glu
        130                 135                 140

Glu Glu Gly Arg Val Arg Ala Met Arg Ala Ala Arg Ser Leu Gly Glu
145                 150                 155                 160

Arg Thr Val Thr Glu Leu Ile Leu Gln His Gln Asn Pro Gln Gln Leu
                165                 170                 175

Ser Ala Asn Leu Trp Ala Ala Val Arg Ala Arg Gly Cys Gln Phe Leu
            180                 185                 190

Gly Pro Ala Met Gln Glu Glu Ala Leu Lys Leu Val Leu Leu Ala Leu
        195                 200                 205

Glu Asp Gly Ser Ala Leu Ser Arg Lys Val Leu Val Leu Phe Val Val
    210                 215                 220
```

-continued

```
Gln Arg Leu Glu Pro Arg Phe Pro Gln Ala Ser Lys Thr Ser Ile Gly
225                 230                 235                 240

His Val Val Gln Leu Leu Tyr Arg Ala Ser Cys Phe Lys Val Thr Lys
            245                 250                 255

Arg Asp Glu Asp Ser Ser Leu Met Gln Leu Lys Glu Glu Phe Arg Ser
        260                 265                 270

Tyr Glu Ala Leu Arg Arg Glu His Asp Ala Gln Ile Val His Ile Ala
    275                 280                 285

Met Glu Ala Gly Leu Arg Ile Ser Pro Glu Gln Trp Ser Ser Leu Leu
290                 295                 300

Tyr Gly Asp Leu Ala His Lys Ser His Met Gln Ser Ile Ile Asp Lys
305                 310                 315                 320

Leu Gln Ser Pro Glu Ser Phe Ala Lys Ser Val Gln Glu Leu Thr Ile
                325                 330                 335

Val Leu Gln Arg Thr Gly Asp Pro Ala Asn Leu Asn Arg Leu Arg Pro
            340                 345                 350

His Leu Glu Leu Leu Ala Asn Ile Asp Pro Asn Pro Asp Ala Val Ser
        355                 360                 365

Pro Thr Trp Glu Gln Leu Glu Asn Ala Met Val Ala Val Lys Thr Val
    370                 375                 380

Val His Gly Leu Val Asp Phe Ile Gln Asn Tyr Ser Arg Lys Gly His
385                 390                 395                 400

Glu Thr Pro Gln Pro Gln Pro Asn Ser Lys Tyr Lys Thr Ser Met Cys
                405                 410                 415

Arg Asp Leu Arg Gln Gln Gly Gly Cys Pro Arg Gly Thr Asn Cys Thr
            420                 425                 430

Phe Ala His Ser Gln Glu Glu Leu Glu Lys Tyr Arg Leu Arg Asn Lys
        435                 440                 445

Lys Ile Asn Ala Thr Val Arg Thr Phe Pro Leu Leu Asn Lys Val Gly
    450                 455                 460

Val Asn Asn Thr Val Thr Thr Thr Ala Gly Asn Val Ile Ser Val Ile
465                 470                 475                 480

Gly Ser Thr Glu Thr Thr Gly Lys Ile Val Pro Ser Thr Asn Gly Ile
                485                 490                 495

Ser Asn Ala Glu Asn Ser Val Ser Gln Leu Ile Ser Arg Ser Thr Asp
            500                 505                 510

Ser Thr Leu Arg Ala Leu Glu Thr Val Lys Lys Val Gly Lys Val Gly
        515                 520                 525

Ala Asn Gly Gln Asn Ala Ala Gly Pro Ser Ala Asp Ser Val Thr Glu
    530                 535                 540

Asn Lys Ile Gly Ser Pro Pro Lys Thr Pro Val Ser Asn Val Ala Ala
545                 550                 555                 560

Thr Ser Ala Gly Pro Ser Asn Val Gly Thr Glu Leu Asn Ser Val Pro
                565                 570                 575

Gln Lys Ser Ser Pro Phe Leu Thr Arg Val Pro Val Tyr Pro Pro His
            580                 585                 590

Ser Glu Asn Ile Gln Tyr Phe Gln Asp Pro Arg Thr Gln Ile Pro Phe
        595                 600                 605

Glu Val Pro Gln Tyr Pro Gln Thr Gly Tyr Tyr Pro Pro Pro Pro Thr
    610                 615                 620

Val Pro Ala Gly Val Ala Pro Cys Val Pro Arg Phe Val Arg Ser Asn
625                 630                 635                 640

Asn Val Pro Glu Ser Ser Leu Pro Pro Ala Ser Met Pro Tyr Ala Asp
```

-continued

```
                645                 650                 655
His Tyr Ser Thr Phe Ser Pro Arg Asp Arg Met Asn Ser Ser Pro Tyr
            660                 665                 670
Gln Pro Pro Pro Gln Pro Tyr Gly Pro Val Pro Val Pro Ser
        675                 680                 685
Gly Met Tyr Ala Pro Val Tyr Asp Ser Arg Arg Ile Trp Arg Pro Pro
690                 695                 700
Met Tyr Gln Arg Asp Asp Ile Ile Arg Ser Asn Ser Leu Pro Pro Met
705                 710                 715                 720
Asp Val Met His Ser Ser Val Tyr Gln Thr Ser Leu Arg Glu Arg Tyr
                725                 730                 735
Asn Ser Leu Asp Gly Tyr Tyr Ser Val Ala Cys Gln Pro Pro Ser Glu
            740                 745                 750
Pro Arg Thr Thr Val Pro Leu Pro Arg Glu Pro Cys Gly His Leu Lys
        755                 760                 765
Thr Ser Cys Glu Glu Gln Ile Arg Arg Lys Pro Asp Gln Trp Ala Gln
        770                 775                 780
Tyr His Thr Gln Lys Ala Pro Leu Val Ser Ser Thr Leu Pro Val Ala
785                 790                 795                 800
Thr Gln Ser Pro Thr Pro Pro Ser Pro Leu Phe Ser Val Asp Phe Arg
                805                 810                 815
Ala Asp Phe Ser Glu Ser Val Ser Gly Thr Lys Phe Glu Glu Asp His
                820                 825                 830
Leu Ser His Tyr Ser Pro Trp Ser Cys Gly Thr Ile Gly Ser Cys Ile
        835                 840                 845
Asn Ala Ile Asp Ser Glu Pro Lys Asp Val Ile Ala Asn Ser Asn Ala
        850                 855                 860
Val Leu Met Asp Leu Asp Ser Gly Asp Val Lys Arg Arg Val His Leu
865                 870                 875                 880
Phe Glu Thr Gln Arg Arg Thr Lys Glu Glu Asp Pro Ile Ile Pro Phe
                885                 890                 895
Ser Asp Gly Pro Ile Ile Ser Lys Trp Gly Ala Ile Ser Arg Ser Ser
            900                 905                 910
Arg Thr Gly Tyr His Thr Thr Asp Pro Val Gln Ala Thr Ala Ser Gln
        915                 920                 925
Gly Ser Ala Thr Lys Pro Ile Ser Val Ser Asp Tyr Val Pro Tyr Val
        930                 935                 940
Asn Ala Val Asp Ser Arg Trp Ser Ser Tyr Gly Asn Glu Ala Thr Ser
945                 950                 955                 960
Ser Ala His Tyr Val Glu Arg Asp Arg Phe Ile Val Thr Asp Leu Ser
                965                 970                 975
Gly His Arg Lys His Ser Ser Thr Gly Asp Leu Leu Ser Leu Glu Leu
            980                 985                 990
Gln Gln Ala Lys Ser Asn Ser Leu  Leu Leu Gln Arg Glu  Ala Asn Ala
        995                 1000                1005
Leu Ala  Met Gln Gln Lys Trp  Asn Ser Leu Asp Glu  Gly Arg His
    1010                1015                1020
Leu Thr  Leu Asn Leu Leu Ser  Lys Glu Ile Glu Leu  Arg Asn Gly
    1025                1030                1035
Glu Leu  Gln Ser Asp Tyr Thr  Glu Asp Ala Thr Asp  Thr Lys Pro
    1040                1045                1050
Asp Arg  Asp Ile Glu Leu Glu  Leu Ser Ala Leu Asp  Thr Asp Glu
    1055                1060                1065
```

```
Pro Asp Gly Gln Ser Glu Pro Ile Glu Glu Ile Leu Asp Ile Gln
    1070            1075                1080

Leu Gly Ile Ser Ser Gln Asn Asp Gln Leu Leu Asn Gly Met Ala
    1085            1090                1095

Val Glu Asn Gly His Pro Val Gln Gln His Gln Lys Glu Pro Pro
    1100            1105                1110

Lys Gln Lys Lys Gln Ser Leu Gly Glu Asp His Val Ile Leu Glu
    1115            1120                1125

Glu Gln Lys Thr Ile Leu Pro Val Thr Ser Cys Phe Ser Gln Pro
    1130            1135                1140

Leu Pro Val Ser Ile Ser Asn Ala Ser Cys Leu Pro Ile Thr Thr
    1145            1150                1155

Ser Val Ser Ala Gly Asn Leu Ile Leu Lys Thr His Val Met Ser
    1160            1165                1170

Glu Asp Lys Asn Asp Phe Leu Lys Pro Val Ala Asn Gly Lys Met
    1175            1180                1185

Val Asn Ser
    1190

<210> SEQ ID NO 3
<211> LENGTH: 4351
<212> TYPE: DNA
<213> ORGANISM: Homo sapiens
<220> FEATURE:
<221> NAME/KEY: CDS
<222> LOCATION: (602)..(4174)

<400> SEQUENCE: 3
agccaagtct tgtcagagat ttcctctttc aggtggcaaa gctgttttct tcacacttga      60
gtctctacaa tattgtttgg atcagtagtt tccaaagttc attaactcct ggccatactt     120
tattatgttt tggggtactg gttatccaag ggaaacactt ttttaaacaa caaacaaaa     180 aaaccgccca gcagtccaaa gtaatttgtg ttcctaaaaa tggaatatgg aaagttaatt     240
tgcttgtttg atgtggtcgt tgagaaaaat acataaaagc tttgatgttt attatgtgag     300
caaccaatat aaatacagtt tagttgaaag gaacactatt aaggtattgt ttccaggcag     360
aatttcagaa atgtaattaa ttcagcaaat aggttttta aaaagacat ccaaaggtta     420 taaaattatt tagaagtatt ttaggtctga agctgtaata gttgacttaa gcaattaact     480
cttcaaaggt gaatgatgaa tatgtggtta attcatactt ttgtccattt ctagcttaca     540
aaacactaca cagcaaaata atgatctgct agactgctaa cccgagcatc cagcttccac     600 a atg gct gtg cag gca gct caa tgg aca gaa ttt ctg tcc tgt cca atc    649
  Met Ala Val Gln Ala Ala Gln Trp Thr Glu Phe Leu Ser Cys Pro Ile
  1               5                   10                  15 tgc tat aat gaa ttt gat gag aat gtg cac aaa ccc atc agt tta ggt    697
Cys Tyr Asn Glu Phe Asp Glu Asn Val His Lys Pro Ile Ser Leu Gly
            20                  25                  30 tgt tca cac act gtt tgc aag acc tgc ttg aat aaa ctt cat cga aaa    745
Cys Ser His Thr Val Cys Lys Thr Cys Leu Asn Lys Leu His Arg Lys
        35                  40                  45 gct tgt cct ttt gac cag act gcc atc aac aca gat att gat gta ctt    793
Ala Cys Pro Phe Asp Gln Thr Ala Ile Asn Thr Asp Ile Asp Val Leu
    50                  55                  60 cct gtc aac ttc gca ctt ctc cag tta gtt gga gcc cag gta cca gat    841
Pro Val Asn Phe Ala Leu Leu Gln Leu Val Gly Ala Gln Val Pro Asp
65                  70                  75                  80
```

-continued

| | | |
|---|---|---|
| cat cag tca att aag tta agt aat cta ggt gag aat aaa cac tat gag<br>His Gln Ser Ile Lys Leu Ser Asn Leu Gly Glu Asn Lys His Tyr Glu<br>                85                         90                        95 | 889 |

```
cat cag tca att aag tta agt aat cta ggt gag aat aaa cac tat gag        889
His Gln Ser Ile Lys Leu Ser Asn Leu Gly Glu Asn Lys His Tyr Glu
             85                  90                  95 gtt gca aag aaa tgc gtt gag gat ttg gca ctc tac tta aaa cca cta        937
Val Ala Lys Lys Cys Val Glu Asp Leu Ala Leu Tyr Leu Lys Pro Leu
         100                 105                 110 agt gga ggt aaa ggt gta gct agc ttg aac cag agt gca ctg agc cgt        985
Ser Gly Gly Lys Gly Val Ala Ser Leu Asn Gln Ser Ala Leu Ser Arg
         115                 120                 125 cca atg caa agg aaa ctg gtg aca ctt gta aac tgt caa ctg gtg gag       1033
Pro Met Gln Arg Lys Leu Val Thr Leu Val Asn Cys Gln Leu Val Glu
130                 135                 140 gaa gaa ggt cgt gta aga gcc atg cga gca gct cgt tcc ctt gga gaa       1081
Glu Glu Gly Arg Val Arg Ala Met Arg Ala Ala Arg Ser Leu Gly Glu
145                 150                 155                 160 aga act gta aca gaa ctg ata tta cag cac cag aac cct cag cag ttg       1129
Arg Thr Val Thr Glu Leu Ile Leu Gln His Gln Asn Pro Gln Gln Leu
             165                 170                 175 tct gcc aat cta tgg gcc gct gtc agg gct cga gga tgc cag ttt tta       1177
Ser Ala Asn Leu Trp Ala Ala Val Arg Ala Arg Gly Cys Gln Phe Leu
         180                 185                 190 ggg cca gct atg caa gaa gag gcc ttg aag ctg gtg tta ctg gca tta       1225
Gly Pro Ala Met Gln Glu Glu Ala Leu Lys Leu Val Leu Leu Ala Leu
         195                 200                 205 gaa gat ggt tct gcc ctc tca agg aaa gtt ctg gta ctt ttt gtt gtg       1273
Glu Asp Gly Ser Ala Leu Ser Arg Lys Val Leu Val Leu Phe Val Val
210                 215                 220 cag aga cta gaa cca aga ttt cct cag gca tca aaa aca agt att ggt       1321
Gln Arg Leu Glu Pro Arg Phe Pro Gln Ala Ser Lys Thr Ser Ile Gly
225                 230                 235                 240 cat gtt gtg caa cta ctg tat cga gct tct tgt ttt aag gtt acc aaa       1369
His Val Val Gln Leu Leu Tyr Arg Ala Ser Cys Phe Lys Val Thr Lys
             245                 250                 255 aga gat gaa gac tct tcc cta atg cag ctg aag gag gaa ttt cgg agt       1417
Arg Asp Glu Asp Ser Ser Leu Met Gln Leu Lys Glu Glu Phe Arg Ser
         260                 265                 270 tat gaa gca tta cgc aga gaa cat gat gcc caa att gtt cat att gcc       1465
Tyr Glu Ala Leu Arg Arg Glu His Asp Ala Gln Ile Val His Ile Ala
         275                 280                 285 atg gaa gca gga ctc cgt att tca cct gaa cag tgg tcc tct ctt ttg       1513
Met Glu Ala Gly Leu Arg Ile Ser Pro Glu Gln Trp Ser Ser Leu Leu
290                 295                 300 tat ggt gat ttg gct cat aaa tca cac atg cag tct atc att gat aag       1561
Tyr Gly Asp Leu Ala His Lys Ser His Met Gln Ser Ile Ile Asp Lys
305                 310                 315                 320 cta cag tct cca gag tca ttt gca aag agt gtc cag gaa ttg aca att       1609
Leu Gln Ser Pro Glu Ser Phe Ala Lys Ser Val Gln Glu Leu Thr Ile
             325                 330                 335 gtt ttg caa cga aca ggt gac cca gct aac tta aat aga ctg agg cct       1657
Val Leu Gln Arg Thr Gly Asp Pro Ala Asn Leu Asn Arg Leu Arg Pro
         340                 345                 350 cat tta gag ctt ctt gca aac ata gac cct aat cca gac gct gtt tca       1705
His Leu Glu Leu Leu Ala Asn Ile Asp Pro Asn Pro Asp Ala Val Ser
         355                 360                 365 cca act tgg gag cag ctg gaa aat gca atg gta gct gtt aaa aca gta       1753
Pro Thr Trp Glu Gln Leu Glu Asn Ala Met Val Ala Val Lys Thr Val
370                 375                 380 gtt cat ggc ctt gtg gac ttc ata caa aat tat agt aga aaa ggc cat       1801
Val His Gly Leu Val Asp Phe Ile Gln Asn Tyr Ser Arg Lys Gly His
385                 390                 395                 400
```

-continued

| | |
|---|---|
| gag acc cct cag cct cag cca aac agc aaa tac aag act agc atg tgc<br>Glu Thr Pro Gln Pro Gln Pro Asn Ser Lys Tyr Lys Thr Ser Met Cys<br>405                410               415 | 1849 |
| cga gat ttg cga cag cag ggg ggt tgt cca cga gga aca aat tgt aca<br>Arg Asp Leu Arg Gln Gln Gly Gly Cys Pro Arg Gly Thr Asn Cys Thr<br>        420                425               430 | 1897 |
| ttt gcc cat tct cag gaa gag ctt gaa aag tat cga tta agg aac aaa<br>Phe Ala His Ser Gln Glu Glu Leu Glu Lys Tyr Arg Leu Arg Asn Lys<br>            435                440              445 | 1945 |
| aag atc aat gcc act gta aga acg ttt cct ctt cta aat aaa gtt ggt<br>Lys Ile Asn Ala Thr Val Arg Thr Phe Pro Leu Leu Asn Lys Val Gly<br>450                455               460 | 1993 |
| gta aac aac act gtc aca acc aca gcc gga aat gtc att tct gtc ata<br>Val Asn Asn Thr Val Thr Thr Thr Ala Gly Asn Val Ile Ser Val Ile<br>465                470               475               480 | 2041 |
| gga agt act gaa aca aca ggg aaa att gtt cca agt aca aac gga att<br>Gly Ser Thr Glu Thr Thr Gly Lys Ile Val Pro Ser Thr Asn Gly Ile<br>        485                490               495 | 2089 |
| tca aat gca gaa aac agt gtt tcc cag cta atc tca cgt agt act gac<br>Ser Asn Ala Glu Asn Ser Val Ser Gln Leu Ile Ser Arg Ser Thr Asp<br>            500                505              510 | 2137 |
| agt acc tta aga gct ctg gag acc gtg aag aaa gtg gga aag gtt ggc<br>Ser Thr Leu Arg Ala Leu Glu Thr Val Lys Lys Val Gly Lys Val Gly<br>515                520               525 | 2185 |
| gct aat ggt cag aat gct gct ggg ccc tct gca gat tct gta act gaa<br>Ala Asn Gly Gln Asn Ala Ala Gly Pro Ser Ala Asp Ser Val Thr Glu<br>530                535               540 | 2233 |
| aat aaa att ggt tct cca ccc aag act cct gta agt aat gta gca gct<br>Asn Lys Ile Gly Ser Pro Pro Lys Thr Pro Val Ser Asn Val Ala Ala<br>545                550               555               560 | 2281 |
| acc tca gct ggg ccc tct aat gtt gga aca gag ctg aat tct gtg cct<br>Thr Ser Ala Gly Pro Ser Asn Val Gly Thr Glu Leu Asn Ser Val Pro<br>        565                570               575 | 2329 |
| caa aaa tcc agc cca ttt cta act aga gta cca gta tat cct ccg cat<br>Gln Lys Ser Ser Pro Phe Leu Thr Arg Val Pro Val Tyr Pro Pro His<br>            580                585              590 | 2377 |
| tct gaa aac att cag tat ttt caa gat cca agg act cag ata ccc ttt<br>Ser Glu Asn Ile Gln Tyr Phe Gln Asp Pro Arg Thr Gln Ile Pro Phe<br>595                600               605 | 2425 |
| gaa gtc cca cag tac cca cag aca gga tac tat cca cca cct cca acg<br>Glu Val Pro Gln Tyr Pro Gln Thr Gly Tyr Tyr Pro Pro Pro Pro Thr<br>        610                615               620 | 2473 |
| gta cca gct ggt gtg gct ccc tgt gtt cct cgc ttt gtg agg tcc aat<br>Val Pro Ala Gly Val Ala Pro Cys Val Pro Arg Phe Val Arg Ser Asn<br>625                630               635               640 | 2521 |
| aac gtt cca gag tcc tcc ctc cca cct gct tcc atg cca tat gcc gat<br>Asn Val Pro Glu Ser Ser Leu Pro Pro Ala Ser Met Pro Tyr Ala Asp<br>            645                650              655 | 2569 |
| cat tac agt aca ttt tcc cct cga gat cga atg aat tct tct cct tac<br>His Tyr Ser Thr Phe Ser Pro Arg Asp Arg Met Asn Ser Ser Pro Tyr<br>        660                665               670 | 2617 |
| cag cct cct cct ccg cag ccg tat gga cca gtt cct cca gta cct tct<br>Gln Pro Pro Pro Pro Gln Pro Tyr Gly Pro Val Pro Pro Val Pro Ser<br>            675                680              685 | 2665 |
| gga atg tat gct cct gtg tac gac agc agg cgc atc tgg cgc cca cct<br>Gly Met Tyr Ala Pro Val Tyr Asp Ser Arg Arg Ile Trp Arg Pro Pro<br>690                695               700 | 2713 |
| atg tac caa cga gat gac att att aga agc aat tct tta cct cca atg<br>Met Tyr Gln Arg Asp Asp Ile Ile Arg Ser Asn Ser Leu Pro Pro Met | 2761 |

-continued

| | | | |
|---|---|---|---|
| 705 | 710 | 715 | 720 | gat gtg atg cac tca tct gtc tat cag aca tct ttg cgg gaa aga tat  2809
Asp Val Met His Ser Ser Val Tyr Gln Thr Ser Leu Arg Glu Arg Tyr
            725                 730                 735 aac tca tta gat gga tat tat tcg gtg gct tgt cag cca cca agt gag  2857
Asn Ser Leu Asp Gly Tyr Tyr Ser Val Ala Cys Gln Pro Pro Ser Glu
            740                 745                 750 cca agg aca act gtg cct tta cca agg gaa cct tgt ggt cat ttg aag  2905
Pro Arg Thr Thr Val Pro Leu Pro Arg Glu Pro Cys Gly His Leu Lys
        755                 760                 765 acc agt tgc gag gag cag ata aga aga aag cca gat cag tgg gca cag  2953
Thr Ser Cys Glu Glu Gln Ile Arg Arg Lys Pro Asp Gln Trp Ala Gln
        770                 775                 780 tac cac act cag aaa gca cct ctt gtc tct tca act ctt cct gtg gca  3001
Tyr His Thr Gln Lys Ala Pro Leu Val Ser Ser Thr Leu Pro Val Ala
785                 790                 795                 800 aca cag tca cca aca cca cct tct cct ctg ttc agt gta gac ttt cgt  3049
Thr Gln Ser Pro Thr Pro Pro Ser Pro Leu Phe Ser Val Asp Phe Arg
            805                 810                 815 gcg gat ttc tca gag agt gtg agt ggt aca aaa ttt gaa gaa gat cat  3097
Ala Asp Phe Ser Glu Ser Val Ser Gly Thr Lys Phe Glu Glu Asp His
            820                 825                 830 ctt tcc cat tat tct ccc tgg tct tgt ggc acc ata ggc tcc tgt ata  3145
Leu Ser His Tyr Ser Pro Trp Ser Cys Gly Thr Ile Gly Ser Cys Ile
            835                 840                 845 aat gcc att gat tca gag ccc aaa gat gtc att gct aat tca aat gct  3193
Asn Ala Ile Asp Ser Glu Pro Lys Asp Val Ile Ala Asn Ser Asn Ala
        850                 855                 860 gtg tta atg gac ctg gac agt ggt gat gtt aag aga aga gta cat tta  3241
Val Leu Met Asp Leu Asp Ser Gly Asp Val Lys Arg Arg Val His Leu
865                 870                 875                 880 ttt gaa acc cag aga agg aca aaa gaa gaa gat cca ata att ccc ttt  3289
Phe Glu Thr Gln Arg Arg Thr Lys Glu Glu Asp Pro Ile Ile Pro Phe
            885                 890                 895 agt gat gga ccc atc atc tca aaa tgg ggt gcg att tcc aga tct tcc  3337
Ser Asp Gly Pro Ile Ile Ser Lys Trp Gly Ala Ile Ser Arg Ser Ser
            900                 905                 910 cgt aca ggt tac cat acc aca gat cct gtc cag gcc act gct tcc caa  3385
Arg Thr Gly Tyr His Thr Thr Asp Pro Val Gln Ala Thr Ala Ser Gln
        915                 920                 925 gga agt gcg act aag ccc atc agt gta tca gat tat gtc cct tat gtc  3433
Gly Ser Ala Thr Lys Pro Ile Ser Val Ser Asp Tyr Val Pro Tyr Val
        930                 935                 940 aat gct gtt gat tca agg tgg agt tca tat ggc aac gag gcc aca tca  3481
Asn Ala Val Asp Ser Arg Trp Ser Ser Tyr Gly Asn Glu Ala Thr Ser
945                 950                 955                 960 tca gca cac tat gtt gaa agg gac aga ttc att gtt act gat tta tct  3529
Ser Ala His Tyr Val Glu Arg Asp Arg Phe Ile Val Thr Asp Leu Ser
            965                 970                 975 ggt cat aga aag cat tcc agt act ggg gac ctt ttg agc ctt gaa ctt  3577
Gly His Arg Lys His Ser Ser Thr Gly Asp Leu Leu Ser Leu Glu Leu
            980                 985                 990 cag cag gcc aag agc aac tca tta ctt ctt cag aga gag gcc aat gct  3625
Gln Gln Ala Lys Ser Asn Ser Leu Leu Leu Gln Arg Glu Ala Asn Ala
        995                 1000                1005 ttg gcc atg caa cag aag tgg aat tcc ctg gat gaa ggc cgt cac  3670
Leu Ala Met Gln Gln Lys Trp Asn Ser Leu Asp Glu Gly Arg His
        1010                1015                1020 ctt acc tta aac ctt tta agc aag gaa att gaa cta aga aat gga  3715

-continued

| | | | | | | | | | | | | |
|---|---|---|---|---|---|---|---|---|---|---|---|---|
| Leu | Thr | Leu | Asn | Leu | Leu | Ser | Lys | Glu | Ile | Glu | Leu | Arg Asn Gly |
| | 1025 | | | | 1030 | | | | 1035 | | | | gag tta cag agt gat tat aca gaa gat gca aca gat act aaa cct    3760
Glu Leu Gln Ser Asp Tyr Thr Glu Asp Ala Thr Asp Thr Lys Pro
    1040            1045                1050 gat agg gat atc gag tta gag ctt tca gca ctt gat act gat gaa    3805
Asp Arg Asp Ile Glu Leu Glu Leu Ser Ala Leu Asp Thr Asp Glu
    1055            1060                1065 cct gat gga caa agt gaa cca att gaa gag atc ttg gac ata cag    3850
Pro Asp Gly Gln Ser Glu Pro Ile Glu Glu Ile Leu Asp Ile Gln
    1070            1075                1080 ctt ggt atc agt tct caa aat gat cag ttg cta aat gga atg gca    3895
Leu Gly Ile Ser Ser Gln Asn Asp Gln Leu Leu Asn Gly Met Ala
    1085            1090                1095 gtg gaa aat ggg cat cca gta cag cag cac caa aag gag cca cca    3940
Val Glu Asn Gly His Pro Val Gln Gln His Gln Lys Glu Pro Pro
    1100            1105                1110 aag cag aag aaa cag agt tta ggt gaa gac cat gtg att ctg gag    3985
Lys Gln Lys Lys Gln Ser Leu Gly Glu Asp His Val Ile Leu Glu
    1115            1120                1125 gag caa aaa aca att ctg ccg gta act tct tgc ttt agc cag cca    4030
Glu Gln Lys Thr Ile Leu Pro Val Thr Ser Cys Phe Ser Gln Pro
    1130            1135                1140 ctc cca gtg tct att agc aat gca agt tgc ctc ccc atc acc aca    4075
Leu Pro Val Ser Ile Ser Asn Ala Ser Cys Leu Pro Ile Thr Thr
    1145            1150                1155 tct gtc agt gct ggc aac ctc att ctg aaa act cat gtt atg tct    4120
Ser Val Ser Ala Gly Asn Leu Ile Leu Lys Thr His Val Met Ser
    1160            1165                1170 gaa gat aaa aac gac ttt tta aaa cct gtt gca aat ggg aag atg    4165
Glu Asp Lys Asn Asp Phe Leu Lys Pro Val Ala Asn Gly Lys Met
    1175            1180                1185 gtt aac agc tgaaaggagg ttcatctttc aaatttgtga ccacaccatg        4214
Val Asn Ser
    1190 gaagcattta cactagcttt ttatatatat aatatatatt atataatgta tattttttt    4274 aaaaaaaaga tattactggg ggcatccatt tcctgtggac tctttgatac ttcaagccct    4334 cttgcattag cattatg                                                    4351

<210> SEQ ID NO 4
<211> LENGTH: 1191
<212> TYPE: PRT
<213> ORGANISM: Homo sapiens

<400> SEQUENCE: 4

Met Ala Val Gln Ala Ala Gln Trp Thr Glu Phe Leu Ser Cys Pro Ile
1               5                   10                  15

Cys Tyr Asn Glu Phe Asp Glu Asn Val His Lys Pro Ile Ser Leu Gly
                20                  25                  30

Cys Ser His Thr Val Cys Lys Thr Cys Leu Asn Lys Leu His Arg Lys
            35                  40                  45

Ala Cys Pro Phe Asp Gln Thr Ala Ile Asn Thr Asp Ile Asp Val Leu
        50                  55                  60

Pro Val Asn Phe Ala Leu Leu Gln Leu Val Gly Ala Gln Val Pro Asp
65                  70                  75                  80

His Gln Ser Ile Lys Leu Ser Asn Leu Gly Glu Asn Lys His Tyr Glu
                85                  90                  95

```
Val Ala Lys Lys Cys Val Glu Asp Leu Ala Leu Tyr Leu Lys Pro Leu
            100                 105                 110

Ser Gly Gly Lys Gly Val Ala Ser Leu Asn Gln Ser Ala Leu Ser Arg
            115                 120                 125

Pro Met Gln Arg Lys Leu Val Thr Leu Val Asn Cys Gln Leu Val Glu
            130                 135                 140

Glu Glu Gly Arg Val Arg Ala Met Arg Ala Ala Arg Ser Leu Gly Glu
145                 150                 155                 160

Arg Thr Val Thr Glu Leu Ile Leu Gln His Gln Asn Pro Gln Gln Leu
                165                 170                 175

Ser Ala Asn Leu Trp Ala Ala Val Arg Ala Arg Gly Cys Gln Phe Leu
            180                 185                 190

Gly Pro Ala Met Gln Glu Glu Ala Leu Lys Leu Val Leu Leu Ala Leu
            195                 200                 205

Glu Asp Gly Ser Ala Leu Ser Arg Lys Val Leu Val Leu Phe Val Val
210                 215                 220

Gln Arg Leu Glu Pro Arg Phe Pro Gln Ala Ser Lys Thr Ser Ile Gly
225                 230                 235                 240

His Val Val Gln Leu Leu Tyr Arg Ala Ser Cys Phe Lys Val Thr Lys
                245                 250                 255

Arg Asp Glu Asp Ser Ser Leu Met Gln Leu Lys Glu Glu Phe Arg Ser
            260                 265                 270

Tyr Glu Ala Leu Arg Arg Glu His Asp Ala Gln Ile Val His Ile Ala
            275                 280                 285

Met Glu Ala Gly Leu Arg Ile Ser Pro Glu Gln Trp Ser Ser Leu Leu
            290                 295                 300

Tyr Gly Asp Leu Ala His Lys Ser His Met Gln Ser Ile Ile Asp Lys
305                 310                 315                 320

Leu Gln Ser Pro Glu Ser Phe Ala Lys Ser Val Gln Glu Leu Thr Ile
                325                 330                 335

Val Leu Gln Arg Thr Gly Asp Pro Ala Asn Leu Asn Arg Leu Arg Pro
            340                 345                 350

His Leu Glu Leu Leu Ala Asn Ile Asp Pro Asn Pro Asp Ala Val Ser
            355                 360                 365

Pro Thr Trp Glu Gln Leu Glu Asn Ala Met Val Ala Val Lys Thr Val
            370                 375                 380

Val His Gly Leu Val Asp Phe Ile Gln Asn Tyr Ser Arg Lys Gly His
385                 390                 395                 400

Glu Thr Pro Gln Pro Gln Pro Asn Ser Lys Tyr Lys Thr Ser Met Cys
                405                 410                 415

Arg Asp Leu Arg Gln Gln Gly Gly Cys Pro Arg Gly Thr Asn Cys Thr
            420                 425                 430

Phe Ala His Ser Gln Glu Glu Leu Glu Lys Tyr Arg Leu Arg Asn Lys
            435                 440                 445

Lys Ile Asn Ala Thr Val Arg Thr Phe Pro Leu Leu Asn Lys Val Gly
            450                 455                 460

Val Asn Asn Thr Val Thr Thr Ala Gly Asn Val Ile Ser Val Ile
465                 470                 475                 480

Gly Ser Thr Glu Thr Thr Gly Lys Ile Val Pro Ser Thr Asn Gly Ile
                485                 490                 495

Ser Asn Ala Glu Asn Ser Val Ser Gln Leu Ile Ser Arg Ser Thr Asp
            500                 505                 510

Ser Thr Leu Arg Ala Leu Glu Thr Val Lys Lys Val Gly Lys Val Gly
```

```
                515                 520                 525
Ala Asn Gly Gln Asn Ala Gly Pro Ser Ala Asp Ser Val Thr Glu
    530                 535                 540

Asn Lys Ile Gly Ser Pro Pro Lys Thr Pro Val Ser Asn Val Ala Ala
545                 550                 555                 560

Thr Ser Ala Gly Pro Ser Asn Val Gly Thr Glu Leu Asn Ser Val Pro
                565                 570                 575

Gln Lys Ser Ser Pro Phe Leu Thr Arg Val Pro Val Tyr Pro Pro His
            580                 585                 590

Ser Glu Asn Ile Gln Tyr Phe Gln Asp Pro Arg Thr Gln Ile Pro Phe
        595                 600                 605

Glu Val Pro Gln Tyr Pro Gln Thr Gly Tyr Tyr Pro Pro Pro Pro Thr
    610                 615                 620

Val Pro Ala Gly Val Ala Pro Cys Val Pro Arg Phe Val Arg Ser Asn
625                 630                 635                 640

Asn Val Pro Glu Ser Ser Leu Pro Pro Ala Ser Met Pro Tyr Ala Asp
                645                 650                 655

His Tyr Ser Thr Phe Ser Pro Arg Asp Arg Met Asn Ser Ser Pro Tyr
            660                 665                 670

Gln Pro Pro Pro Gln Pro Tyr Gly Pro Val Pro Pro Val Pro Pro Ser
        675                 680                 685

Gly Met Tyr Ala Pro Val Tyr Asp Ser Arg Arg Ile Trp Arg Pro Pro
    690                 695                 700

Met Tyr Gln Arg Asp Asp Ile Ile Arg Ser Asn Ser Leu Pro Pro Met
705                 710                 715                 720

Asp Val Met His Ser Ser Val Tyr Gln Thr Ser Leu Arg Glu Arg Tyr
                725                 730                 735

Asn Ser Leu Asp Gly Tyr Tyr Ser Val Ala Cys Gln Pro Pro Ser Glu
            740                 745                 750

Pro Arg Thr Thr Val Pro Leu Pro Arg Glu Pro Cys Gly His Leu Lys
        755                 760                 765

Thr Ser Cys Glu Glu Gln Ile Arg Arg Lys Pro Asp Gln Trp Ala Gln
    770                 775                 780

Tyr His Thr Gln Lys Ala Pro Leu Val Ser Ser Thr Leu Pro Val Ala
785                 790                 795                 800

Thr Gln Ser Pro Thr Pro Ser Pro Leu Phe Ser Val Asp Phe Arg
                805                 810                 815

Ala Asp Phe Ser Glu Ser Val Ser Gly Thr Lys Phe Glu Glu Asp His
            820                 825                 830

Leu Ser His Tyr Ser Pro Trp Ser Cys Gly Thr Ile Gly Ser Cys Ile
        835                 840                 845

Asn Ala Ile Asp Ser Glu Pro Lys Asp Val Ile Ala Asn Ser Asn Ala
    850                 855                 860

Val Leu Met Asp Leu Asp Ser Gly Asp Val Lys Arg Arg Val His Leu
865                 870                 875                 880

Phe Glu Thr Gln Arg Arg Thr Lys Glu Glu Asp Pro Ile Ile Pro Phe
                885                 890                 895

Ser Asp Gly Pro Ile Ile Ser Lys Trp Gly Ala Ile Ser Arg Ser Ser
            900                 905                 910

Arg Thr Gly Tyr His Thr Thr Asp Pro Val Gln Ala Thr Ala Ser Gln
        915                 920                 925

Gly Ser Ala Thr Lys Pro Ile Ser Val Ser Asp Tyr Val Pro Tyr Val
    930                 935                 940
```

Asn Ala Val Asp Ser Arg Trp Ser Ser Tyr Gly Asn Glu Ala Thr Ser
945                 950                 955                 960

Ser Ala His Tyr Val Glu Arg Asp Arg Phe Ile Val Thr Asp Leu Ser
            965                 970                 975

Gly His Arg Lys His Ser Ser Thr Gly Asp Leu Leu Ser Leu Glu Leu
            980                 985                 990

Gln Gln Ala Lys Ser Asn Ser Leu Leu Leu Gln Arg Glu Ala Asn Ala
            995                 1000                1005

Leu Ala Met Gln Gln Lys Trp Asn Ser Leu Asp Glu Gly Arg His
    1010                1015                1020

Leu Thr Leu Asn Leu Leu Ser Lys Glu Ile Glu Leu Arg Asn Gly
    1025                1030                1035

Glu Leu Gln Ser Asp Tyr Thr Glu Asp Ala Thr Asp Thr Lys Pro
    1040                1045                1050

Asp Arg Asp Ile Glu Leu Glu Leu Ser Ala Leu Asp Thr Asp Glu
    1055                1060                1065

Pro Asp Gly Gln Ser Glu Pro Ile Glu Glu Ile Leu Asp Ile Gln
    1070                1075                1080

Leu Gly Ile Ser Ser Gln Asn Asp Gln Leu Leu Asn Gly Met Ala
    1085                1090                1095

Val Glu Asn Gly His Pro Val Gln Gln His Gln Lys Glu Pro Pro
    1100                1105                1110

Lys Gln Lys Lys Gln Ser Leu Gly Glu Asp His Val Ile Leu Glu
    1115                1120                1125

Glu Gln Lys Thr Ile Leu Pro Val Thr Ser Cys Phe Ser Gln Pro
    1130                1135                1140

Leu Pro Val Ser Ile Ser Asn Ala Ser Cys Leu Pro Ile Thr Thr
    1145                1150                1155

Ser Val Ser Ala Gly Asn Leu Ile Leu Lys Thr His Val Met Ser
    1160                1165                1170

Glu Asp Lys Asn Asp Phe Leu Lys Pro Val Ala Asn Gly Lys Met
    1175                1180                1185

Val Asn Ser
    1190

<210> SEQ ID NO 5
<211> LENGTH: 39
<212> TYPE: DNA
<213> ORGANISM: Artificial
<220> FEATURE:
<223> OTHER INFORMATION: PCR primer 1 for cloning DNA-R

<400> SEQUENCE: 5
acccgagcat ggatcckcca cmatgsctgt gcaggcagc                    39

<210> SEQ ID NO 6
<211> LENGTH: 26
<212> TYPE: DNA
<213> ORGANISM: Artificial
<220> FEATURE:
<223> OTHER INFORMATION: PCR primer 2 for cloning DNA-R

<400> SEQUENCE: 6
ggtatctaga tccatggtgt ggtcac                                  26

<210> SEQ ID NO 7
<211> LENGTH: 574

-continued

```
<212> TYPE: PRT
<213> ORGANISM: Homo sapiens

<400> SEQUENCE: 7

Met Ala Thr Leu Val Val Asn Lys Leu Gly Ala Gly Val Asp Ser Gly
1               5                   10                  15

Arg Gln Gly Ser Arg Gly Thr Ala Val Lys Val Leu Glu Cys Gly
            20                  25                  30

Val Cys Glu Asp Val Phe Ser Leu Gln Gly Asp Lys Val Pro Arg Leu
        35                  40                  45

Leu Leu Cys Gly His Thr Val Cys His Asp Cys Leu Thr Arg Leu Pro
    50                  55                  60

Leu His Gly Arg Ala Ile Arg Cys Pro Phe Asp Arg Gln Val Thr Asp
65                  70                  75                  80

Leu Gly Asp Ser Gly Val Trp Gly Leu Lys Lys Asn Phe Ala Leu Leu
                85                  90                  95

Glu Leu Leu Glu Arg Leu Gln Asn Gly Pro Ile Gly Gln Tyr Gly Ala
            100                 105                 110

Ala Glu Glu Ser Ile Gly Ile Ser Gly Glu Ser Ile Ile Arg Cys Asp
        115                 120                 125

Glu Asp Glu Ala His Leu Ala Ser Val Tyr Cys Thr Val Cys Ala Thr
    130                 135                 140

His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Cys Val Cys Lys Glu Tyr
        195                 200                 205

Gly Lys His Gln Gly His Lys His Ser Val Leu Glu Pro Glu Ala Asn
    210                 215                 220

Gln Ile Arg Ala Ser Ile Leu Asp Met Ala His Cys Ile Arg Thr Phe
225                 230                 235                 240

Thr Glu Glu Ile Ser Asp Tyr Ser Arg Lys Leu Val Gly Ile Val Gln
                245                 250                 255

His Ile Glu Gly Gly Glu Gln Ile Val Glu Asp Gly Ile Gly Met Ala
            260                 265                 270

His Thr Glu His Val Pro Gly Thr Ala Glu Asn Ala Arg Ser Cys Ile
        275                 280                 285

Arg Ala Tyr Phe Tyr Asp Leu His Glu Thr Leu Cys Arg Gln Glu Glu
    290                 295                 300

Met Ala Leu Ser Val Val Asp Ala His Val Arg Glu Lys Leu Ile Trp
305                 310                 315                 320

Leu Arg Gln Gln Gln Glu Asp Met Thr Ile Leu Leu Ser Glu Val Ser
                325                 330                 335

Ala Ala Cys Leu His Cys Glu Lys Thr Leu Gln Gln Asp Asp Cys Arg
            340                 345                 350

Val Val Leu Ala Lys Gln Glu Ile Thr Arg Leu Leu Thr Glu Leu Gln
        355                 360                 365

Lys Gln Gln Gln Gln Phe Thr Glu Val Ala Asp His Ile Gln Leu Asp
    370                 375                 380

Ala Ser Ile Pro Val Thr Phe Thr Lys Asp Asn Arg Val His Ile Gly
385                 390                 395                 400
```

-continued

Pro Lys Met Glu Ile Arg Val Val Thr Leu Gly Leu Asp Gly Ala Gly
                405                 410                 415

Lys Thr Thr Ile Leu Phe Lys Leu Lys Gln Asp Glu Phe Met Gln Pro
            420                 425                 430

Ile Pro Thr Ile Gly Phe Asn Val Glu Thr Val Glu Tyr Lys Asn Leu
        435                 440                 445

Lys Phe Thr Ile Trp Asp Val Gly Gly Lys His Lys Leu Arg Pro Leu
    450                 455                 460

Trp Lys His Tyr Tyr Leu Asn Thr Gln Ala Val Val Phe Val Val Asp
465                 470                 475                 480

Ser Ser His Arg Asp Arg Ile Ser Glu Ala His Ser Glu Leu Ala Lys
                485                 490                 495

Leu Leu Thr Glu Lys Glu Leu Arg Asp Ala Leu Leu Leu Ile Phe Ala
            500                 505                 510

Asn Lys Gln Asp Val Ala Gly Ala Leu Ser Val Glu Glu Ile Thr Glu
        515                 520                 525

Leu Leu Ser Leu His Lys Leu Cys Cys Gly Arg Ser Trp Tyr Ile Gln
    530                 535                 540

Gly Cys Asp Ala Arg Ser Gly Met Gly Leu Tyr Glu Gly Leu Asp Trp
545                 550                 555                 560

Leu Ser Arg Gln Leu Val Ala Ala Gly Val Leu Asp Val Ala
                565                 570

<210> SEQ ID NO 8
<211> LENGTH: 317
<212> TYPE: PRT
<213> ORGANISM: Homo sapiens

<400> SEQUENCE: 8

Met Gly Tyr Asp Val Thr Arg Phe Gln Gly Asp Val Asp Glu Asp Leu
1               5                   10                  15

Ile Cys Pro Ile Cys Ser Gly Val Leu Glu Glu Pro Val Gln Ala Pro
            20                  25                  30

His Cys Glu His Ala Phe Cys Asn Ala Cys Ile Thr Gln Trp Phe Ser
        35                  40                  45

Gln Gln Gln Thr Cys Pro Val Asp Arg Ser Val Thr Val Ala His
    50                  55                  60

Leu Arg Pro Val Pro Arg Ile Met Arg Asn Met Leu Ser Lys Leu Gln
65                  70                  75                  80

Ile Ala Cys Asp Asn Ala Val Phe Gly Cys Ser Ala Val Val Arg Leu
                85                  90                  95

Asp Asn Leu Met Ser His Leu Ser Asp Cys Glu His Asn Pro Lys Arg
            100                 105                 110

Pro Val Thr Cys Glu Gln Gly Cys Gly Leu Glu Met Pro Lys Asp Glu
        115                 120                 125

Leu Pro Asn His Asn Cys Ile Lys His Leu Arg Ser Val Val Gln Gln
    130                 135                 140

Gln Gln Thr Arg Ile Ala Glu Leu Glu Lys Thr Ser Ala Glu His Lys
145                 150                 155                 160

His Gln Leu Ala Glu Gln Lys Arg Asp Ile Gln Leu Leu Lys Ala Tyr
                165                 170                 175

Met Arg Ala Ile Arg Ser Val Asn Pro Asn Leu Gln Asn Leu Glu Glu
            180                 185                 190

Thr Ile Glu Tyr Asn Glu Ile Leu Glu Trp Val Asn Ser Leu Gln Pro

-continued

```
                    195                 200                 205
Ala Arg Val Thr Arg Trp Gly Gly Met Ile Ser Thr Pro Asp Ala Val
    210                 215                 220

Leu Gln Ala Val Ile Lys Arg Ser Leu Val Glu Ser Gly Cys Pro Ala
225                 230                 235                 240

Ser Ile Val Asn Glu Leu Ile Glu Asn Ala His Glu Arg Ser Trp Pro
                245                 250                 255

Gln Gly Leu Ala Thr Leu Glu Thr Arg Gln Met Asn Arg Arg Tyr Tyr
            260                 265                 270

Glu Asn Tyr Val Ala Lys Arg Ile Pro Gly Lys Gln Ala Val Val Val
        275                 280                 285

Met Ala Cys Glu Asn Gln His Met Gly Asp Asp Met Val Gln Glu Pro
    290                 295                 300

Gly Leu Val Met Ile Phe Ala His Gly Val Glu Ile
305                 310                 315
```

<210> SEQ ID NO 9
<211> LENGTH: 202
<212> TYPE: PRT
<213> ORGANISM: Caenorhabditis elegans

<400> SEQUENCE: 9

```
Met Arg Met Met Glu Ala Glu Ile Lys Asp Gln Arg Asn Asn Leu Gln
1               5                   10                  15

Ala Leu Lys Asn Ser Gln Arg Leu Ser Val Arg Gly Ser Ile Gln Ser
            20                  25                  30

Asn Met Ser Ser Arg Thr Asp Gly Ile Leu Gln Arg Arg Leu Asp Glu
        35                  40                  45

Thr Glu Arg Lys Leu Ala Lys Thr Ser Ala Glu Leu Lys Ala Lys Asp
    50                  55                  60

Glu Lys Leu Lys Lys Glu Thr Ala Ser Leu Glu Ala Ser Arg Glu Ala
65                  70                  75                  80

His Arg Leu Leu Gln Glu Glu Ser Asn Lys Ser Lys Val Ser Val Met
                85                  90                  95

Arg Leu Thr Phe Lys Leu Asn Arg Ile Thr His Glu Ser Val Lys Glu
            100                 105                 110

Gln Ala Val Leu Lys Lys Leu Leu Asp Cys Glu Thr Arg Leu Ala
        115                 120                 125

Thr Tyr Ser Glu Cys Leu Val Cys Tyr Gln Lys Phe Asp Glu Asn Thr
    130                 135                 140

Arg Ile Pro Arg Val Met Asp Cys Gly His Thr Leu Cys Asp Phe Cys
145                 150                 155                 160

Ile Asn Gln Ile Val Lys Met Ala Gly Cys Tyr Ser Ala Thr Cys Pro
                165                 170                 175

Phe Asp Arg Val Arg Ile Phe Gly Phe Gly Lys Ser Arg Arg Leu Glu
            180                 185                 190

Asp Arg Pro Cys Asn Arg Phe Ile Met Lys
        195                 200
```

<210> SEQ ID NO 10
<211> LENGTH: 218
<212> TYPE: PRT
<213> ORGANISM: Caenorhabditis elegans

<400> SEQUENCE: 10

Met Ala Pro Ile Arg Arg Ser Ser Arg Leu Ala Glu Arg Tyr Asp Ala

```
                 1               5                  10                 15
Ile Glu Ser Lys Lys Arg Ser Leu Lys Arg Leu Glu Glu Gln Ile Lys
                20                  25                  30

Ala Glu Glu Gln Phe Ser Asp Lys Met Lys Gln Leu Glu Asp Glu
        35                  40                  45

Ile Lys Ile Lys Glu Gln Val Ile Thr Met Phe Lys Arg Lys Thr Val
        50                  55                  60

Arg Arg Glu Trp Met Arg Asn Ser Arg Gln Ala Thr Thr Asn Ile Asn
65                      70                  75                  80

Ile Ala Gln Ile Glu Ser Leu Lys Leu Gln Leu Glu Glu Gly Glu Lys
                85                  90                  95

Asp Ile Ala Glu Ala Glu Lys Gln Ala Glu Pro Thr Thr Pro Gln Gln
            100                 105                 110

Glu Ala Glu Leu Ser Glu Thr Phe Lys Gln Met Val Arg Asp Arg Met
        115                 120                 125

Lys Val Lys Asp Val Asp Glu Lys Leu Leu Gln Gln Tyr Met Lys Lys
        130                 135                 140

Glu Asn Val Glu Phe Glu Trp Arg Ser Cys Phe Ile Cys Thr Met Glu
145                 150                 155                 160

Tyr Ser Arg Thr Asp Lys Asn Leu His Pro Ile Ile Leu Asn Cys Gly
                165                 170                 175

His Asn Leu Cys Arg Ser Cys Ile Asn Lys Leu Thr Gly Asn Gly Ile
            180                 185                 190

Val Lys Cys Pro Phe Asp Arg Leu Asp Thr Arg Val Arg Val Thr Gly
        195                 200                 205

Leu Pro Arg Asn Leu Ala Leu Ile Asn Leu
        210                 215

<210> SEQ ID NO 11
<211> LENGTH: 1048
<212> TYPE: PRT
<213> ORGANISM: Caenorhabditis elegans

<400> SEQUENCE: 11

Met Ala Pro Thr Gly Gln Gly Gly Gln Trp Gln Glu Val Leu Cys Cys
1               5                   10                  15

Ser Ile Cys Asn Arg His Phe Asn Glu Thr Phe Leu Pro Val Ser Leu
                20                  25                  30

Ile Cys Gly His Val Ile Cys Arg Lys Cys Ala Glu Lys Pro Glu Asn
        35                  40                  45

Gln Thr Lys Pro Cys Pro His Asp Asp Trp Lys Thr Thr His Ser Pro
        50                  55                  60

Ser Glu Tyr Pro Asn Asn Val Ala Leu Leu Ser Val Ile Phe Pro Arg
65                      70                  75                  80

Lys Gln Cys Met Thr Leu Ser Gly Ala Val Ser Glu Ala Glu Lys Arg
                85                  90                  95

Val Asp Gln Leu Ser Ile Gln Ile Ala Lys Phe Phe Arg Glu Ala Asp
            100                 105                 110

Ser Glu Arg Gly Gly Thr Val Ser Ser Arg Glu Ile Ser Arg Thr Leu
        115                 120                 125

Gln Arg Lys Val Leu Ala Leu Leu Cys Tyr Gln Trp Arg Glu Val Asp
        130                 135                 140

Gly Arg Leu Lys Thr Leu Lys Met Cys Arg Gly Ile Ser Glu Arg Val
145                 150                 155                 160
```

```
Met Ile Glu Ile Ile Leu Ser Ile Gln Ser Asn Thr His Val Ser Ser
                165                 170                 175

Gln Leu Trp Ser Ala Val Arg Ala Arg Gly Cys Gln Phe Leu Gly Pro
            180                 185                 190

Ala Met Gln Asp Asp Val Leu Arg Leu Ile Leu Met Thr Leu Glu Thr
        195                 200                 205

Gly Glu Cys Ile Ala Arg Lys Asn Leu Val Met Tyr Val Val Gln Thr
    210                 215                 220

Leu Ala Ser Asp Tyr Pro Gln Val Ser Lys Thr Cys Val Gly His Val
225                 230                 235                 240

Val Gln Leu Leu Tyr Arg Ala Ser Cys Phe Asn Val Leu Lys Arg Asp
                245                 250                 255

Gly Glu Ser Ser Leu Met Gln Leu Lys Glu Glu Phe Arg Thr Tyr Glu
            260                 265                 270

Ser Leu Arg Arg Glu His Asp Ser Gln Ile Val Gln Ile Ala Phe Glu
        275                 280                 285

Ser Gly Leu Arg Ile Gly Pro Asp Gln Trp Ser Ala Leu Leu Tyr Ala
    290                 295                 300

Asp Gln Ser His Arg Ser His Met Gln Ser Ile Ile Asp Lys Leu Gln
305                 310                 315                 320

Ser Lys Asn Ser Tyr Gln Gln Gly Val Glu Glu Leu Arg Ala Leu Ala
                325                 330                 335

Gly Ser Gln Thr Ser Met Leu Val Pro Ala Tyr Arg Tyr Phe Leu Thr
            340                 345                 350

Gln Val Ile Pro Cys Leu Glu Phe Phe Ala Gly Ile Glu His Glu Asp
        355                 360                 365

Thr Ser Met Arg Met Ile Gly Asp Ala Leu His Gln Ile Arg Ile Leu
    370                 375                 380

Leu Lys Leu His Cys Ser Gln Asp Asp Leu Arg Lys Met Pro Lys Glu
385                 390                 395                 400

Glu Arg Arg Gly Val Ile Leu Gln Ala Glu Val Pro Gly Gly Met Gly
                405                 410                 415

Gly Gly Pro Gly Gly Ser Gly Ala Glu Ala Gly Arg Ile Gly Gly
            420                 425                 430

Leu His Pro Leu Tyr Ser Gln Ile Asp Glu Thr Gly Arg Ser Ile Ser
        435                 440                 445

Arg Thr Asn Pro Lys Asp Asn Ser His Asn Ser Pro Gln Thr Pro Pro
    450                 455                 460

Lys Gln Pro Arg Gln Lys Arg Tyr Gln Met Gly Ile Pro Pro Asn Arg
465                 470                 475                 480

Met Gly Tyr Ser Ser Asp Ala Pro Pro Phe Ile Pro Ser His Gln Gln
                485                 490                 495

Gln Pro Pro Pro Gln Phe Phe Asn Ser Gln His Leu Pro Gln Arg Phe
            500                 505                 510

Arg Gly Gly Arg Gln Arg Gly Ala Pro Pro Pro Pro Gln Pro
        515                 520                 525

Met Pro Met Leu Ile Gly Tyr Asp Met Pro Gly Ala Pro Met Met Gln
    530                 535                 540

Ala Thr Glu Val Leu Thr Ala Asp Gly Gln Met Val Asn Gly Thr Pro
545                 550                 555                 560

Gln Arg Val Val Ile Met Gln Ser Pro Thr His Leu Pro Gly Gly Pro
                565                 570                 575

Val Val Met Ile Pro Gln Gln Gln Met Val Pro Pro Pro Gln Ser Met
```

-continued

```
             580                 585                 590
Thr Pro Val Gly Gly Pro Met Gly Pro Met Gly Pro Met Thr Pro Ser
             595                 600                 605
Ile Pro Val Gln Val Pro Pro Asn Thr Met Trp Thr Ala Thr Ser Pro
             610                 615                 620
Thr Gly Ser Val Ile Tyr Pro Ala Ala Ser Pro Pro Gly Gln Pro Pro
625                  630                 635                 640
His Thr Ile Trp Ile Gln Ser Ile Gly Val Phe Lys Arg Lys Ser Asn
                     645                 650                 655
Phe Leu Lys Ile Val Arg Lys Ile Ser Phe Leu Asn Phe Tyr Asp
             660                 665                 670
Phe Phe Leu Ile Leu Arg Lys Leu Lys Lys Glu Lys Lys Gly Ala Asp
             675                 680                 685
Ile Glu Phe Glu Lys Ile Lys Ser Thr Asp Phe Lys Lys Tyr Pro
             690                 695                 700
Ser Ser Phe Ser Arg Thr Asp Gly Asn Met Phe Pro Met Phe Asp Arg
705                  710                 715                 720
Gly Ser Gly Gly Met Val Trp Gly Pro Gly Thr Met Leu Arg Glu Ser
                     725                 730                 735
Gly Ala Asp Ala Glu Gln Leu Leu Ala Lys Arg Tyr Glu Ile Leu Lys
             740                 745                 750
Arg Leu Gln Pro Ser Glu Asp Asp Asp Pro Glu Asp Gly Gly Ile
             755                 760                 765
Gly His Val Ser Tyr Thr Val Ala Ser Ser Val Leu Asp Asp Arg Met
770                  775                 780
Asp His His Pro Leu Thr Met Ile Pro Val Pro Thr Ile Asp Leu Pro
785                  790                 795                 800
Ala Ile Pro Ile Ser Phe Ala Asn Met Pro Thr Glu Thr Met Thr
             805                 810                 815
Met Ile Gly Glu Met Val Gln Asn Arg Pro Arg Ala Pro Ser Leu Thr
             820                 825                 830
Ala Pro Ser Ser Asn Gln Pro Met Asn Val Asn Ala Ser Ala Ser Ala
             835                 840                 845
Thr Val Gln Ala Glu Cys Glu Asn Arg Lys Ile Leu Asp Phe Pro Leu
850                  855                 860
Lys Tyr Arg Lys Met Thr Leu Met Phe Glu Lys Val Ser Thr Cys Phe
865                  870                 875                 880
His Val Thr Leu Leu Lys Asp Tyr Met Val Phe Tyr Val Leu Asn Thr
                     885                 890                 895
Leu Asn Phe Ala Ser Arg Trp Pro Arg Arg Arg Ala Ala Thr Ile
             900                 905                 910
Pro Gln Pro Val Ile Pro Met Val Gln Val Pro Val Gln Val Pro Ile
             915                 920                 925
Val Pro Ala Glu Asn Phe Asn Pro Asn Val Pro Pro Pro Pro Pro
             930                 935                 940
Pro Gln Gly Gln Pro Met Leu Val Asp Ser Ala Ile Gly Leu Leu Thr
945                  950                 955                 960
Pro Ile Arg Pro Ile Leu Val Ala His Pro Gln Asn Val Val Ser Asn
                     965                 970                 975
Ser Leu Asp Lys Ile Val Asp Val Lys Glu Arg Ile Ser Glu Ala Gln
             980                 985                 990
Gly Asn Ala Ser Glu Ala Glu Asn  Ala His Leu Arg Met  Glu Leu Arg
             995                1000                1005
```

```
Met Ala Glu Ser Gln Met Ala His Leu Asp Pro Tyr Thr Lys Asn
    1010            1015                1020

Asn Cys Leu Leu Arg Ala Leu Gln Gln Val Asp Met Glu Leu Gln
    1025            1030                1035

Gln Leu His Leu Asn Pro Thr Val Glu Gly
    1040            1045

<210> SEQ ID NO 12
<211> LENGTH: 1999
<212> TYPE: DNA
<213> ORGANISM: Homo sapiens
<220> FEATURE:
<221> NAME/KEY: CDS
<222> LOCATION: (86)..(1498)

<400> SEQUENCE: 12
```

| | |
|---|---:|
| gccgggagcg ccgctccagc gaggcgcggg ctgtggggcc gccgcgtgcc tggccccgct | 60 |
| cgcccgtgcc ggccgctcgc cgcc atg cct ggc ttc gac tac aag ttc ctg | 112 |
|                              Met Pro Gly Phe Asp Tyr Lys Phe Leu | |
|                                1               5                 | |
| gag aag ccc aag cga cgg ctg ctg tgc cca ctg tgc ggg aag ccc atg | 160 |
| Glu Lys Pro Lys Arg Arg Leu Leu Cys Pro Leu Cys Gly Lys Pro Met | |
|  10              15                  20                  25      | |
| cgc gag cct gtg cag gtt tcc acc tgc ggc cac cgt ttc tgc gat acc | 208 |
| Arg Glu Pro Val Gln Val Ser Thr Cys Gly His Arg Phe Cys Asp Thr | |
|                  30                  35                  40      | |
| tgc ctg cag gag ttc ctc agt gaa gga gtc ttc aag tgc cct gag gac | 256 |
| Cys Leu Gln Glu Phe Leu Ser Glu Gly Val Phe Lys Cys Pro Glu Asp | |
|              45                  50                  55          | |
| cag ctt cct ctg gac tat gcc aag atc tac cca gac ccg gag ctg gaa | 304 |
| Gln Leu Pro Leu Asp Tyr Ala Lys Ile Tyr Pro Asp Pro Glu Leu Glu | |
|          60                  65                  70              | |
| gta caa gta ttg ggc ctg cct atc cgc tgc atc cac agt gag gag ggc | 352 |
| Val Gln Val Leu Gly Leu Pro Ile Arg Cys Ile His Ser Glu Glu Gly | |
|      75                  80                  85                  | |
| tgc cgc tgg agt ggg cca cta cgt cat cta cag ggc cac ctg aat acc | 400 |
| Cys Arg Trp Ser Gly Pro Leu Arg His Leu Gln Gly His Leu Asn Thr | |
|  90                  95                 100                 105  | |
| tgc agc ttc aat gtc att ccc tgc cct aat cgc tgc ccc atg aag ctg | 448 |
| Cys Ser Phe Asn Val Ile Pro Cys Pro Asn Arg Cys Pro Met Lys Leu | |
|                 110                 115                 120      | |
| agc cgc cgt gat cta cct gca cac ttg cag cat gac tgc ccc aag cgg | 496 |
| Ser Arg Arg Asp Leu Pro Ala His Leu Gln His Asp Cys Pro Lys Arg | |
|             125                 130                 135          | |
| cgc ctc aag tgc gag ttt tgt ggc tgt gac ttc agt ggg gag gcc tat | 544 |
| Arg Leu Lys Cys Glu Phe Cys Gly Cys Asp Phe Ser Gly Glu Ala Tyr | |
|         140                 145                 150              | |
| gag agc cat gag ggt atg tgc ccc cag gag agt gtc tac tgt gag aat | 592 |
| Glu Ser His Glu Gly Met Cys Pro Gln Glu Ser Val Tyr Cys Glu Asn | |
|     155                 160                 165                  | |
| aag tgt ggt gcc cgc atg atg cgg ggg ctg ctg gcc cag cat gcc acc | 640 |
| Lys Cys Gly Ala Arg Met Met Arg Gly Leu Leu Ala Gln His Ala Thr | |
| 170                 175                 180                 185  | |
| tct gag tgc ccc aag cgc act cag ccc tgc acc tac tgc act aag gag | 688 |
| Ser Glu Cys Pro Lys Arg Thr Gln Pro Cys Thr Tyr Cys Thr Lys Glu | |
|                 190                 195                 200      | |
| ttc gtc ttt gac acc atc cag agc cac cag tac cag tgc cca agg ctg | 736 |
| Phe Val Phe Asp Thr Ile Gln Ser His Gln Tyr Gln Cys Pro Arg Leu | |
|             205                 210                 215          | |

|                                                                                                                                          |      |
|------------------------------------------------------------------------------------------------------------------------------------------|------|
| cct gtt gcc tgc ccc aac caa tgt ggt gtg ggc act gtg gct cgg gag<br>Pro Val Ala Cys Pro Asn Gln Cys Gly Val Gly Thr Val Ala Arg Glu<br>220           225           230                                         | 784  |
| gac ctg cca ggc cat ctg aag gac agc tgt aac acc gcc ctg gtg ctc<br>Asp Leu Pro Gly His Leu Lys Asp Ser Cys Asn Thr Ala Leu Val Leu<br>235           240           245                                         | 832  |
| tgc cca ttc aaa gac tcc ggc tgc aag cac agg tgc cct aag ctg gca<br>Cys Pro Phe Lys Asp Ser Gly Cys Lys His Arg Cys Pro Lys Leu Ala<br>250           255           260           265                           | 880  |
| atg gca cgg cat gtg gag gag agt gtg aag cca cat ctg gcc atg atg<br>Met Ala Arg His Val Glu Glu Ser Val Lys Pro His Leu Ala Met Met<br>            270           275           280                           | 928  |
| tgt gcc ctg gtg agc cgg caa cgg cag gag ctg cag gag ctt cgg cga<br>Cys Ala Leu Val Ser Arg Gln Arg Gln Glu Leu Gln Glu Leu Arg Arg<br>        285           290           295                                 | 976  |
| gag ctg gag gag cta tca gtg ggc agt gat ggc gtg ctc atc tgg aag<br>Glu Leu Glu Glu Leu Ser Val Gly Ser Asp Gly Val Leu Ile Trp Lys<br>300           305           310                                         | 1024 |
| att ggc agc tat gga cgg cgg cta cag gag gcc aag gcc aag ccc aac<br>Ile Gly Ser Tyr Gly Arg Arg Leu Gln Glu Ala Lys Ala Lys Pro Asn<br>315           320           325                                         | 1072 |
| ctt gag tgc ttc agc cca gcc ttc tac aca cat aag tat ggt tac aag<br>Leu Glu Cys Phe Ser Pro Ala Phe Tyr Thr His Lys Tyr Gly Tyr Lys<br>330           335           340           345                           | 1120 |
| ctg cag gtg tct gca ttc ctc aat ggc aat ggc agt ggt gag ggc aca<br>Leu Gln Val Ser Ala Phe Leu Asn Gly Asn Gly Ser Gly Glu Gly Thr<br>        350           355           360                                 | 1168 |
| cac ctc tca ctg tac att cgt gtg ctg cct ggt gcc ttt gac aat ctc<br>His Leu Ser Leu Tyr Ile Arg Val Leu Pro Gly Ala Phe Asp Asn Leu<br>        365           370           375                                 | 1216 |
| ctt gag tgg ccc ttt gcc cgc cgt gtc acc ttc tcc ctg ctg gat cag<br>Leu Glu Trp Pro Phe Ala Arg Arg Val Thr Phe Ser Leu Leu Asp Gln<br>        380           385           390                                 | 1264 |
| agc gac cct ggg ctg gct aaa cca cag cac gtc act gag acc ttc cac<br>Ser Asp Pro Gly Leu Ala Lys Pro Gln His Val Thr Glu Thr Phe His<br>395           400           405                                         | 1312 |
| ccc gac cca aac tgg aag aat ttc cag aag cca ggc acg tgg cgg ggc<br>Pro Asp Pro Asn Trp Lys Asn Phe Gln Lys Pro Gly Thr Trp Arg Gly<br>410           415           420           425                           | 1360 |
| tcc ctg gat gag agt tct ctg ggc ttt ggt tat ccc aag ttc atc tcc<br>Ser Leu Asp Glu Ser Ser Leu Gly Phe Gly Tyr Pro Lys Phe Ile Ser<br>        430           435           440                                 | 1408 |
| cac cag gac att cga aag cga aac tat gtg cgg gat gat gca gtc ttc<br>His Gln Asp Ile Arg Lys Arg Asn Tyr Val Arg Asp Asp Ala Val Phe<br>445           450           455                                         | 1456 |
| atc cgt gct gct gtt gaa ctg ccc cgg aag atc ctc agc tga<br>Ile Arg Ala Ala Val Glu Leu Pro Arg Lys Ile Leu Ser<br>460           465           470                                                              | 1498 |
| gtgcaggtgg ggttcgaggg gaaaggacga tggggcatga cctcagtcag gcactggctg                                                                        | 1558 |
| aacttggaga gggggccgga ccccgtcag ctgcttctgc tgcctaggtt ctgttacccc                                                                         | 1618 |
| atcctccctc cccagccac caccctcagg tgcctccaat tggtgcttca gccctggccc                                                                         | 1678 |
| ctgtggggaa caggtcttgg ggtcatgaag ggctggaaac aagtgacccc agggcctgtc                                                                        | 1738 |
| tcccttcttg ggtagggcag acatgccttg gtgccggtca cactctacac ggactgaggt                                                                        | 1798 |
| gcctgctcag gtgctatgtc ccaagagcca taaggggtg ggaattgggg agggagaaag                                                                         | 1858 |
| ggtagttcaa agagtctgtc ttgagatctg attttttccc cctttaccta gctgtgcccc                                                                        | 1918 |
| ctctggttat ttatttcctt agtgccagga gggcacagca ggggagccct gattttaat                                                                         | 1978 | aaatccggaa ttgtatttat t         1999

<210> SEQ ID NO 13
<211> LENGTH: 470
<212> TYPE: PRT
<213> ORGANISM: Homo sapiens

<400> SEQUENCE: 13

Met Pro Gly Phe Asp Tyr Lys Phe Leu Glu Lys Pro Lys Arg Arg Leu
1               5                   10                  15

Leu Cys Pro Leu Cys Gly Lys Pro Met Arg Glu Pro Val Gln Val Ser
            20                  25                  30

Thr Cys Gly His Arg Phe Cys Asp Thr Cys Leu Gln Glu Phe Leu Ser
        35                  40                  45

Glu Gly Val Phe Lys Cys Pro Glu Asp Gln Leu Pro Leu Asp Tyr Ala
    50                  55                  60

Lys Ile Tyr Pro Asp Pro Glu Leu Glu Val Gln Val Leu Gly Leu Pro
65                  70                  75                  80

Ile Arg Cys Ile His Ser Glu Glu Gly Cys Arg Trp Ser Gly Pro Leu
                85                  90                  95

Arg His Leu Gln Gly His Leu Asn Thr Cys Ser Phe Asn Val Ile Pro
            100                 105                 110

Cys Pro Asn Arg Cys Pro Met Lys Leu Ser Arg Arg Asp Leu Pro Ala
        115                 120                 125

His Leu Gln His Asp Cys Pro Lys Arg Leu Lys Cys Glu Phe Cys
    130                 135                 140

Gly Cys Asp Phe Ser Gly Glu Ala Tyr Glu Ser His Glu Gly Met Cys
145                 150                 155                 160

Pro Gln Glu Ser Val Tyr Cys Glu Asn Lys Cys Gly Ala Arg Met Met
                165                 170                 175

Arg Gly Leu Leu Ala Gln His Ala Thr Ser Glu Cys Pro Lys Arg Thr
            180                 185                 190

Gln Pro Cys Thr Tyr Cys Thr Lys Glu Phe Val Phe Asp Thr Ile Gln
        195                 200                 205

Ser His Gln Tyr Gln Cys Pro Arg Leu Pro Val Ala Cys Pro Asn Gln
    210                 215                 220

Cys Gly Val Gly Thr Val Ala Arg Glu Asp Leu Pro Gly His Leu Lys
225                 230                 235                 240

Asp Ser Cys Asn Thr Ala Leu Val Leu Cys Pro Phe Lys Asp Ser Gly
                245                 250                 255

Cys Lys His Arg Cys Pro Lys Leu Ala Met Ala Arg His Val Glu Glu
            260                 265                 270

Ser Val Lys Pro His Leu Ala Met Met Cys Ala Leu Val Ser Arg Gln
        275                 280                 285

Arg Gln Glu Leu Gln Glu Leu Arg Arg Glu Leu Glu Leu Ser Val
    290                 295                 300

Gly Ser Asp Gly Val Leu Ile Trp Lys Ile Gly Ser Tyr Gly Arg Arg
305                 310                 315                 320

Leu Gln Glu Ala Lys Ala Lys Pro Asn Leu Glu Cys Phe Ser Pro Ala
                325                 330                 335

Phe Tyr Thr His Lys Tyr Gly Tyr Lys Leu Gln Val Ser Ala Phe Leu
            340                 345                 350

Asn Gly Asn Gly Ser Gly Glu Gly Thr His Leu Ser Leu Tyr Ile Arg
        355                 360                 365

```
Val Leu Pro Gly Ala Phe Asp Asn Leu Leu Glu Trp Pro Phe Ala Arg
    370                 375                 380

Arg Val Thr Phe Ser Leu Leu Asp Gln Ser Asp Pro Gly Leu Ala Lys
385                 390                 395                 400

Pro Gln His Val Thr Glu Thr Phe His Pro Asp Pro Asn Trp Lys Asn
                405                 410                 415

Phe Gln Lys Pro Gly Thr Trp Arg Gly Ser Leu Asp Glu Ser Ser Leu
            420                 425                 430

Gly Phe Gly Tyr Pro Lys Phe Ile Ser His Gln Asp Ile Arg Lys Arg
        435                 440                 445

Asn Tyr Val Arg Asp Asp Ala Val Phe Ile Arg Ala Ala Val Glu Leu
    450                 455                 460

Pro Arg Lys Ile Leu Ser
465                 470

<210> SEQ ID NO 14
<211> LENGTH: 1105
<212> TYPE: DNA
<213> ORGANISM: Caenorhabditis elegans
<220> FEATURE:
<221> NAME/KEY: CDS
<222> LOCATION: (10)..(1017)

<400> SEQUENCE: 14
```

| | | | |
|---|---|---|---|
| aagtttgag atg gct caa aca aag ccg att gcc gag caa atg gct gca ctc<br>Met Ala Gln Thr Lys Pro Ile Ala Glu Gln Met Ala Ala Leu<br>1                        5                      10 | 51 |
| aac aac tca gat gac acg tcg ttc gct gcc gat cga tcg aac agt ctt<br>Asn Asn Ser Asp Asp Thr Ser Phe Ala Ala Asp Arg Ser Asn Ser Leu<br>15                   20                25                30 | 99 |
| ctg aat gcg acg tgc ccg gcg aga att caa aat tca gta gat caa cgg<br>Leu Asn Ala Thr Cys Pro Ala Arg Ile Gln Asn Ser Val Asp Gln Arg<br>                35                40                45 | 147 |
| aaa atc aat cga tca ttc aat gat tcg ctg tcg tcc gga tat agt gga<br>Lys Ile Asn Arg Ser Phe Asn Asp Ser Leu Ser Ser Gly Tyr Ser Gly<br>           50                55                60 | 195 |
| aaa tgg ctt cgt cca aag cgt gaa gcg ctc aag atc act cca ttg gct<br>Lys Trp Leu Arg Pro Lys Arg Glu Ala Leu Lys Ile Thr Pro Leu Ala<br>65                   70                75 | 243 |
| cag att gac gag gcg ccg gca act aaa aga cat agc tcg gcg aag gat<br>Gln Ile Asp Glu Ala Pro Ala Thr Lys Arg His Ser Ser Ala Lys Asp<br>     80               85                90 | 291 |
| aag cac aca gaa tac aaa acg cga ctt tgt gat gcg ttc cgc cgt gaa<br>Lys His Thr Glu Tyr Lys Thr Arg Leu Cys Asp Ala Phe Arg Arg Glu<br>95                   100              105           110 | 339 |
| gga tac tgc ccg tac aac gac aat tgc aca tat gct cac gga caa gat<br>Gly Tyr Cys Pro Tyr Asn Asp Asn Cys Thr Tyr Ala His Gly Gln Asp<br>                115              120           125 | 387 |
| gag ctg aga gtt ccg aga cgc cgc caa gag tat tat tcc cga gat cca<br>Glu Leu Arg Val Pro Arg Arg Arg Gln Glu Tyr Tyr Ser Arg Asp Pro<br>          130              135              140 | 435 |
| cca cgt gag cgc cgt gat tct cgt tct aga cga gac gac gtg gat aca<br>Pro Arg Glu Arg Arg Asp Ser Arg Ser Arg Arg Asp Asp Val Asp Thr<br>145                   150              155 | 483 |
| aca atc aat cga tcg agt tct tca gca tcg aag cat cat gat gag aat<br>Thr Ile Asn Arg Ser Ser Ser Ser Ala Ser Lys His His Asp Glu Asn<br>         160               165              170 | 531 |
| cgg aga ccc agc aac aac cac gga agc tcg aat cgt cgt cag att tgt<br>Arg Arg Pro Ser Asn Asn His Gly Ser Ser Asn Arg Arg Gln Ile Cys | 579 |

```
cac aat ttc gag aga gga aac tgc aga tat ggt cca aga tgc cgc ttc    627
His Asn Phe Glu Arg Gly Asn Cys Arg Tyr Gly Pro Arg Cys Arg Phe
            195                 200                 205 att cac gtc gaa caa atg caa cat ttc aat gcg aat gcg acg gtt tac    675
Ile His Val Glu Gln Met Gln His Phe Asn Ala Asn Ala Thr Val Tyr
        210                 215                 220 gcg cca cct tct tcc gat tgt ccg ccg ccg att gcc tac tac cat cat    723
Ala Pro Pro Ser Ser Asp Cys Pro Pro Pro Ile Ala Tyr Tyr His His
            225                 230                 235 cat cca caa cat cag caa caa ttc ctg cca ttt cca atg cca tat ttc    771
His Pro Gln His Gln Gln Gln Phe Leu Pro Phe Pro Met Pro Tyr Phe
        240                 245                 250 ttg gct cca ccg ccg caa gct caa caa gga gct cct ttt cca gtg caa    819
Leu Ala Pro Pro Pro Gln Ala Gln Gln Gly Ala Pro Phe Pro Val Gln
255                 260                 265                 270 tat att cca cag caa cat gat ttg atg aat agc cag cca atg tat gca    867
Tyr Ile Pro Gln Gln His Asp Leu Met Asn Ser Gln Pro Met Tyr Ala
                275                 280                 285 cca atg gca ccg aca tac tac tat caa cca att aat tcg aat ggc atg    915
Pro Met Ala Pro Thr Tyr Tyr Tyr Gln Pro Ile Asn Ser Asn Gly Met
        290                 295                 300 ccc atg atg gat gtg act att gat ccg aat gcc acg ggc ggt gcg ttt    963
Pro Met Met Asp Val Thr Ile Asp Pro Asn Ala Thr Gly Gly Ala Phe
            305                 310                 315 gaa gtg ttc ccc gat gga ttc ttc tct cag cca cca cca act att att   1011
Glu Val Phe Pro Asp Gly Phe Phe Ser Gln Pro Pro Pro Thr Ile Ile
320                 325                 330 tcc taa ttttgccgta ttttccatat tttgttttgt atatttatcc actcaccccc    1067
Ser
335 tctctttgtc ctgtgaatga acttgtgcca aaaaagcc                          1105

<210> SEQ ID NO 15
<211> LENGTH: 335
<212> TYPE: PRT
<213> ORGANISM: Caenorhabditis elegans

<400> SEQUENCE: 15

Met Ala Gln Thr Lys Pro Ile Ala Glu Gln Met Ala Ala Leu Asn Asn
1               5                   10                  15

Ser Asp Asp Thr Ser Phe Ala Ala Asp Arg Ser Asn Ser Leu Leu Asn
            20                  25                  30

Ala Thr Cys Pro Ala Arg Ile Gln Asn Ser Val Asp Gln Arg Lys Ile
        35                  40                  45

Asn Arg Ser Phe Asn Asp Ser Leu Ser Ser Gly Tyr Ser Gly Lys Trp
    50                  55                  60

Leu Arg Pro Lys Arg Glu Ala Leu Lys Ile Thr Pro Leu Ala Gln Ile
65                  70                  75                  80

Asp Glu Ala Pro Ala Thr Lys Arg His Ser Ser Ala Lys Asp Lys His
                85                  90                  95

Thr Glu Tyr Lys Thr Arg Leu Cys Asp Ala Phe Arg Arg Glu Gly Tyr
            100                 105                 110

Cys Pro Tyr Asn Asp Asn Cys Thr Tyr Ala His Gly Gln Asp Glu Leu
        115                 120                 125

Arg Val Pro Arg Arg Arg Gln Glu Tyr Tyr Ser Arg Asp Pro Pro Arg
    130                 135                 140
```

```
Glu Arg Arg Asp Ser Arg Ser Arg Arg Asp Asp Val Asp Thr Thr Ile
145                 150                 155                 160

Asn Arg Ser Ser Ser Ala Ser Lys His His Asp Glu Asn Arg Arg
                165                 170                 175

Pro Ser Asn Asn His Gly Ser Ser Asn Arg Arg Gln Ile Cys His Asn
            180                 185                 190

Phe Glu Arg Gly Asn Cys Arg Tyr Gly Pro Arg Cys Arg Phe Ile His
        195                 200                 205

Val Glu Gln Met Gln His Phe Asn Ala Asn Ala Thr Val Tyr Ala Pro
    210                 215                 220

Pro Ser Ser Asp Cys Pro Pro Ile Ala Tyr Tyr His His His Pro
225                 230                 235                 240

Gln His Gln Gln Gln Phe Leu Pro Phe Pro Met Pro Tyr Phe Leu Ala
                245                 250                 255

Pro Pro Pro Gln Ala Gln Gln Gly Ala Pro Phe Pro Val Gln Tyr Ile
            260                 265                 270

Pro Gln Gln His Asp Leu Met Asn Ser Gln Pro Met Tyr Ala Pro Met
        275                 280                 285

Ala Pro Thr Tyr Tyr Gln Pro Ile Asn Ser Asn Gly Met Pro Met
    290                 295                 300

Met Asp Val Thr Ile Asp Pro Asn Ala Thr Gly Gly Ala Phe Glu Val
305                 310                 315                 320

Phe Pro Asp Gly Phe Phe Ser Gln Pro Pro Thr Ile Ile Ser
                325                 330                 335

<210> SEQ ID NO 16
<211> LENGTH: 2077
<212> TYPE: DNA
<213> ORGANISM: Drosophila melanogaster
<220> FEATURE:
<221> NAME/KEY: CDS
<222> LOCATION: (301)..(1614)

<400> SEQUENCE: 16
ttttttgcga acgagcgaag agcgacagga cctctcgcgc ccgtattcaa actgattttt      60
ttttattgtt gcaatgcaat attcgcggaa cgaataacaa caacatacat aactcaatat     120
tcaagtgcaa agcaaataca aatcaaacac aaagaaaaag caacgaaata agatatata      180 gaaaagaaaa acaaaacgaa aaaattcgca cattttttct gtcttgtcca gtggaaaata     240
caacaaataa acaacaacgg ctaaatcaag ttaacaatct gttcaaaacc aatcaacaaa     300 atg tct gct gat att ctg cag aaa tca aga gag cag gat gat tcg cac      348
Met Ser Ala Asp Ile Leu Gln Lys Ser Arg Glu Gln Asp Asp Ser His
1               5                  10                  15 tac ttc gag cgt ggc gat ata tcc aaa tac gta acg atg aac gat cac      396
Tyr Phe Glu Arg Gly Asp Ile Ser Lys Tyr Val Thr Met Asn Asp His
            20                  25                  30 ttg ggt gat ttc gat tgc aac gag gtg cgc aag gaa ata agg atg ctg      444
Leu Gly Asp Phe Asp Cys Asn Glu Val Arg Lys Glu Ile Arg Met Leu
        35                  40                  45 ctc gcc cac ggc gcc aac ttg gat cag cag cac cag cag cag cca cat      492
Leu Ala His Gly Ala Asn Leu Asp Gln Gln His Gln Gln Gln Pro His
    50                  55                  60 cgc cac cat ggc ggt ctc aca cgc acc att tca cag ccg gcc cag ctc      540
Arg His His Gly Gly Leu Thr Arg Thr Ile Ser Gln Pro Ala Gln Leu
65                  70                  75                  80 atc cag cag cag cag cag caa cac caa cag cag cag cag cag cag          588
Ile Gln Gln Gln Gln Gln Gln His Gln Gln Gln Gln Gln Gln Gln
```

```
                        85                  90                  95
cca cct gtt gcc agt ctg gtg acc atc acc gag aac ctg ggc aac atg        636
Pro Pro Val Ala Ser Leu Val Thr Ile Thr Glu Asn Leu Gly Asn Met
            100                 105                 110 aac ctg cac cga aag ctg gag cga acc caa tcg gag cca ctg ccg cca        684
Asn Leu His Arg Lys Leu Glu Arg Thr Gln Ser Glu Pro Leu Pro Pro
            115                 120                 125 cag cag ccg atg aac aca tcc aga tac aag acc gag ctg tgc cgt ccg        732
Gln Gln Pro Met Asn Thr Ser Arg Tyr Lys Thr Glu Leu Cys Arg Pro
130                 135                 140 ttc gag gag gcc gga gaa tgc aag tac ggc gag aag tgc cag ttc gcc        780
Phe Glu Glu Ala Gly Glu Cys Lys Tyr Gly Glu Lys Cys Gln Phe Ala
145                 150                 155                 160 cat gga agc cat gag ttg cga aac gtg cac cgt cat ccc aag tac aag        828
His Gly Ser His Glu Leu Arg Asn Val His Arg His Pro Lys Tyr Lys
            165                 170                 175 acg gaa tac tgc cgc acc ttc cac agc gtg ggc ttc tgt ccc tac gga        876
Thr Glu Tyr Cys Arg Thr Phe His Ser Val Gly Phe Cys Pro Tyr Gly
            180                 185                 190 ccg cgc tgt cac ttt gtt cac aat gcg gac gag gcc cgc gcc caa cag        924
Pro Arg Cys His Phe Val His Asn Ala Asp Glu Ala Arg Ala Gln Gln
            195                 200                 205 gcg gcc cag gca gcc aag tcc tcc acc cag tcg cag tcg cag tcg cag        972
Ala Ala Gln Ala Ala Lys Ser Ser Thr Gln Ser Gln Ser Gln Ser Gln
210                 215                 220 cag tcg tcg tcg cag aac ttc tcg ccg aag agc aac cag agc agc aat       1020
Gln Ser Ser Ser Gln Asn Phe Ser Pro Lys Ser Asn Gln Ser Ser Asn
225                 230                 235                 240 caa agt agc aac agt agc agc agc agc agc agc ggc ggc ggc ggt           1068
Gln Ser Ser Asn Ser Ser Ser Ser Ser Ser Ser Gly Gly Gly Gly
            245                 250                 255 ggc ggc ggc aac agc atc aac aac aac aac ggt agc caa ttc tat ctg       1116
Gly Gly Gly Asn Ser Ile Asn Asn Asn Asn Gly Ser Gln Phe Tyr Leu
            260                 265                 270 ccg cta agc cca ccg ctg agc atg agc aca gga tcg gac cgg gaa tcg       1164
Pro Leu Ser Pro Pro Leu Ser Met Ser Thr Gly Ser Asp Arg Glu Ser
            275                 280                 285 ccc acc gga tca ctg tcc ctc agc ccc acc aac tcg ttg acc agc ttc       1212
Pro Thr Gly Ser Leu Ser Leu Ser Pro Thr Asn Ser Leu Thr Ser Phe
290                 295                 300 ccg ttc cac gat gcc ctg cag cat gga tat ttg gca tcg aat ggc gcc       1260
Pro Phe His Asp Ala Leu Gln His Gly Tyr Leu Ala Ser Asn Gly Ala
305                 310                 315                 320 aag agc aac agt tcc gcc tcg tcc aca tca tcg gcc tct gga atg ggt       1308
Lys Ser Asn Ser Ser Ala Ser Ser Thr Ser Ser Ala Ser Gly Met Gly
            325                 330                 335 ctg ggc atg agc atg ggc atc ggc cag ggc atg atc atc ggt cag ggt       1356
Leu Gly Met Ser Met Gly Ile Gly Gln Gly Met Ile Ile Gly Gln Gly
            340                 345                 350 ttg gga atg gga cat cat gga ccg gcc aca ccg ccg gag agc ccc aat       1404
Leu Gly Met Gly His His Gly Pro Ala Thr Pro Pro Glu Ser Pro Asn
            355                 360                 365 gtg ccc ata tcg cca gtg cat aca cca cca ccg tac gat gtg gtg gtc       1452
Val Pro Ile Ser Pro Val His Thr Pro Pro Pro Tyr Asp Val Val Val
370                 375                 380 agt gga tct gga gcg ggc aac aat agc gtt ggc agc aag cag ctc ctg       1500
Ser Gly Ser Gly Ala Gly Asn Asn Ser Val Gly Ser Lys Gln Leu Leu
385                 390                 395                 400 cag aag agc gtc agc aca ccg atg cag cag gag gat acg ccc agg ttg       1548
```

```
Gln Lys Ser Val Ser Thr Pro Met Gln Gln Glu Asp Thr Pro Arg Leu
            405                 410                 415 ccg gtt ttc aac cgt ctc agc tcc ggt gtg gag gcc tac cag cag cag       1596
Pro Val Phe Asn Arg Leu Ser Ser Gly Val Glu Ala Tyr Gln Gln Gln
            420                 425                 430 tcc aat ttg gga ctc taa acgcgtggca gtctgcgaaa caaaattgaa              1644
Ser Asn Leu Gly Leu
            435 ttgaaacacc atccagcatc caactcacgc ccatccaagc atccctccat caacaaacca    1704 gcatccttga caaatctca gtaacgacca aaccatggaa actgaaaaca aaactactct     1764 cgcagtccaa tttgaaacgc aaatatgcca aggcaaatgg atttccggtg gcgtaacttc    1824 gttgcagaat aagtgtgtat caagtatacg ccaaacacag acacccctta attatgaacc    1884 gatccttgat atcaattctc tcattgctgt gacagtcaaa cgtaatcgtt atacaataat    1944 cgttatatga gaaggaccga attacggact actacgggac aattagttag atagatacgt    2004 aaatgacaaa caacaatcc aagcaaacga tgatcttaaa ctataactaa atactaaaaa     2064 ctaaaaacta aca                                                       2077
```

```
<210> SEQ ID NO 17
<211> LENGTH: 437
<212> TYPE: PRT
<213> ORGANISM: Drosophila melanogaster

<400> SEQUENCE: 17

Met Ser Ala Asp Ile Leu Gln Lys Ser Arg Glu Gln Asp Asp Ser His
1               5                   10                  15

Tyr Phe Glu Arg Gly Asp Ile Ser Lys Tyr Val Thr Met Asn Asp His
                20                  25                  30

Leu Gly Asp Phe Asp Cys Asn Glu Val Arg Lys Glu Ile Arg Met Leu
            35                  40                  45

Leu Ala His Gly Ala Asn Leu Asp Gln Gln His Gln Gln Pro His
        50                  55                  60

Arg His His Gly Gly Leu Thr Arg Thr Ile Ser Gln Pro Ala Gln Leu
65                  70                  75                  80

Ile Gln Gln Gln Gln Gln His Gln Gln Gln Gln Gln Gln Gln
                85                  90                  95

Pro Pro Val Ala Ser Leu Val Thr Ile Thr Glu Asn Leu Gly Asn Met
            100                 105                 110

Asn Leu His Arg Lys Leu Glu Arg Thr Gln Ser Glu Pro Leu Pro Pro
        115                 120                 125

Gln Gln Pro Met Asn Thr Ser Arg Tyr Lys Thr Glu Leu Cys Arg Pro
    130                 135                 140

Phe Glu Glu Ala Gly Glu Cys Lys Tyr Gly Glu Lys Cys Gln Phe Ala
145                 150                 155                 160

His Gly Ser His Glu Leu Arg Asn Val His Arg Pro Lys Tyr Lys
                165                 170                 175

Thr Glu Tyr Cys Arg Thr Phe His Ser Val Gly Phe Cys Pro Tyr Gly
            180                 185                 190

Pro Arg Cys His Phe Val His Asn Ala Asp Glu Ala Arg Ala Gln Gln
        195                 200                 205

Ala Ala Gln Ala Ala Lys Ser Ser Thr Gln Ser Gln Ser Gln Ser Gln
    210                 215                 220

Gln Ser Ser Ser Gln Asn Phe Ser Pro Lys Ser Asn Gln Ser Ser Asn
225                 230                 235                 240
```

```
Gln Ser Ser Asn Ser Ser Ser Ser Ser Ser Gly Gly Gly
            245                 250                 255

Gly Gly Gly Asn Ser Ile Asn Asn Asn Gly Ser Gln Phe Tyr Leu
            260                 265                 270

Pro Leu Ser Pro Pro Leu Ser Met Ser Thr Gly Ser Asp Arg Glu Ser
            275                 280                 285

Pro Thr Gly Ser Leu Ser Leu Ser Pro Thr Asn Ser Leu Thr Ser Phe
        290                 295                 300

Pro Phe His Asp Ala Leu Gln His Gly Tyr Leu Ala Ser Asn Gly Ala
305                 310                 315                 320

Lys Ser Asn Ser Ser Ala Ser Ser Thr Ser Ser Ala Ser Gly Met Gly
                325                 330                 335

Leu Gly Met Ser Met Gly Ile Gly Gln Gly Met Ile Ile Gly Gln Gly
            340                 345                 350

Leu Gly Met Gly His His Gly Pro Ala Thr Pro Pro Glu Ser Pro Asn
        355                 360                 365

Val Pro Ile Ser Pro Val His Thr Pro Pro Tyr Asp Val Val Val
    370                 375                 380

Ser Gly Ser Gly Ala Gly Asn Asn Ser Val Gly Ser Lys Gln Leu Leu
385                 390                 395                 400

Gln Lys Ser Val Ser Thr Pro Met Gln Gln Glu Asp Thr Pro Arg Leu
                405                 410                 415

Pro Val Phe Asn Arg Leu Ser Ser Gly Val Glu Ala Tyr Gln Gln Gln
            420                 425                 430

Ser Asn Leu Gly Leu
        435
```

<210> SEQ ID NO 18
<211> LENGTH: 3922
<212> TYPE: DNA
<213> ORGANISM: Homo sapiens
<220> FEATURE:
<221> NAME/KEY: CDS
<222> LOCATION: (774)..(1733)

<400> SEQUENCE: 18

| | | | | |
|---|---|---|---|---|
| aagcttgctc | ttgcagccaa | agactaatt | gcaaaggcat | cttctcagtg | aaggggcgg | 60 |
| ggtgggctag | ggctgagtgg | aaatggtgag | agagattatt | gtagaaaata | tctcttccgg | 120 |
| gaacttaggg | caaagagttt | tattttcagg | aatcacatcc | ctgtctcccc | caacctcaga | 180 |
| ccaggccccc | aatctcctcc | ccacaagaaa | aagcaaaggc | agtctgaaaa | cctgttgcca | 240 |
| aaggaaggga | acacttctga | aggaggaagt | tgagagtctt | aggccaggtc | ttgaaggagg | 300 |
| gggtatcaat | taagcagaga | ctgattggaa | ggggacctaa | cgtgcctatg | atagactcct | 360 |
| ttctgaggtt | tacctgtttt | tgtcgcgggc | ggtggcgggg | cgggtgcggt | aatctagaga | 420 |
| ggtctgggtt | gtgtgagata | ttttgagttg | aagaatctat | ttgactagta | aaaagttga | 480 |
| actttaaagt | ggtagctttg | gggacagagg | acatgggggt | tgcattgcag | gagtcagcat | 540 |
| ggagcagggt | gcttgtcaca | cagtttggat | cttgtggttt | cttacgcatg | gggccaaaat | 600 |
| aaacccaggt | gaatggccta | tgggaggag | agagggaagg | gagcttgcta | gagccgaggt | 660 |
| agagatgagt | tctttgagaa | agagcgggcg | tttgtgattg | tgtaggggc | tgcccatagt | 720 |
| ggacatcctg | gtggatgtcc | tctgtcctta | ccatccttct | cttctctctc | cag ggt | 776 |
| | | | | | Gly |
| | | | | | 1 |

-continued

| | |
|---|---|
| aac aag atg ctc aac tat agt gct ccc agt gca ggg ggt tgc ctg ctg<br>Asn Lys Met Leu Asn Tyr Ser Ala Pro Ser Ala Gly Gly Cys Leu Leu<br>            5                    10                      15 | 824 |
| gac aga aag gca gtg ggc acc cct gct ggt ggg ggc ttc cct cgg agg<br>Asp Arg Lys Ala Val Gly Thr Pro Ala Gly Gly Gly Phe Pro Arg Arg<br>         20                    25                    30 | 872 |
| cac tca gtc acc ctg ccc agc tcc aag ttc cac cag aac cag ctc ctc<br>His Ser Val Thr Leu Pro Ser Ser Lys Phe His Gln Asn Gln Leu Leu<br>    35                    40                    45 | 920 |
| agc agc ctc aag ggt gag cca gcc ccc gct ctg agc tcg cga gac agc<br>Ser Ser Leu Lys Gly Glu Pro Ala Pro Ala Leu Ser Ser Arg Asp Ser<br>50                    55                    60                    65 | 968 |
| cgc ttc cga gac cgc tcc ttc tcg gaa ggg ggc gag cgg ctg ctg ccc<br>Arg Phe Arg Asp Arg Ser Phe Ser Glu Gly Gly Glu Arg Leu Leu Pro<br>                  70                    75                    80 | 1016 |
| acc cag aag cag ccc ggg ggc ggc cag gtc aac tcc agc cgc tac aag<br>Thr Gln Lys Gln Pro Gly Gly Gly Gln Val Asn Ser Ser Arg Tyr Lys<br>            85                    90                    95 | 1064 |
| acg gag ctg tgc cgc ccc ttt gag gaa aac ggt gcc tgt aag tac ggg<br>Thr Glu Leu Cys Arg Pro Phe Glu Glu Asn Gly Ala Cys Lys Tyr Gly<br>    100                   105                  110 | 1112 |
| gac aag tgc cag ttc gca cac ggc atc cac gag ctc cgc agc ctg acc<br>Asp Lys Cys Gln Phe Ala His Gly Ile His Glu Leu Arg Ser Leu Thr<br>         115                   120                  125 | 1160 |
| cgc cac ccc aag tac aag acg gag ctg tgc cgc acc ttc cac acc atc<br>Arg His Pro Lys Tyr Lys Thr Glu Leu Cys Arg Thr Phe His Thr Ile<br>130                    135                   140                145 | 1208 |
| ggc ttt tgc ccc tac ggg ccc cgc tgc cac ttc atc cac aac gct gaa<br>Gly Phe Cys Pro Tyr Gly Pro Arg Cys His Phe Ile His Asn Ala Glu<br>                     150                   155                  160 | 1256 |
| gag cgc cgt gcc ctg gcc ggg gcc cgg gac ctc tcc gct gac cgt ccc<br>Glu Arg Arg Ala Leu Ala Gly Ala Arg Asp Leu Ser Ala Asp Arg Pro<br>                165                   170                   175 | 1304 |
| cgc ctc cag cat agc ttt agc ttt gct ggg ttt ccc agt gcc gct gcc<br>Arg Leu Gln His Ser Phe Ser Phe Ala Gly Phe Pro Ser Ala Ala Ala<br>            180                   185                  190 | 1352 |
| acc gcc gct gcc acc ggg ctg ctg gac agc ccc acg tcc atc acc cca<br>Thr Ala Ala Ala Thr Gly Leu Leu Asp Ser Pro Thr Ser Ile Thr Pro<br>     195                   200                   205 | 1400 |
| ccc cct att ctg agc gcc gat gac ctc ctg ggc tca cct acc ctg ccc<br>Pro Pro Ile Leu Ser Ala Asp Asp Leu Leu Gly Ser Pro Thr Leu Pro<br>210                    215                   220                   225 | 1448 |
| gat ggc acc aat aac cct ttt gcc ttc tcc agc cag gag ctg gca agc<br>Asp Gly Thr Asn Asn Pro Phe Ala Phe Ser Ser Gln Glu Leu Ala Ser<br>                   230                   235                  240 | 1496 |
| ctc ttt gcc cct agc atg ggg ctg ccc ggg ggt ggc tcc ccg acc acc<br>Leu Phe Ala Pro Ser Met Gly Leu Pro Gly Gly Gly Ser Pro Thr Thr<br>                245                   250                   255 | 1544 |
| ttc ctc ttc cgg ccc atg tcc gag tcc cct cac atg ttt gac tct ccc<br>Phe Leu Phe Arg Pro Met Ser Glu Ser Pro His Met Phe Asp Ser Pro<br>            260                   265                  270 | 1592 |
| ccc agc cct cag gat tct ctc tcg gac cag gag ggc tac ctg agc agc<br>Pro Ser Pro Gln Asp Ser Leu Ser Asp Gln Glu Gly Tyr Leu Ser Ser<br>275                    280                   285 | 1640 |
| tcc agc agc agc cac agt ggc tca gac tcc ccg acc ttg gac aac tca<br>Ser Ser Ser Ser His Ser Gly Ser Asp Ser Pro Thr Leu Asp Asn Ser<br>290                    295                   300                  305 | 1688 |
| aga cgc ctg ccc atc ttc agc aga ctt tcc atc tca gat gac taa<br>Arg Arg Leu Pro Ile Phe Ser Arg Leu Ser Ile Ser Asp Asp<br>                   310                   315 | 1733 |

-continued

```
gccagggtag ggagggacct cctgcctact ccagccccta ccctgcaccc acatcccata    1793
ccctcttctc cctacccatc ccattcccca caggccctac attaacaagg ttaagctcaa    1853
cccctttccc ccagcacctc agaatgtgcc ctccctctcc ccctcataac cccacctaac    1913
ataaggacaa gtcaatttgt cagtagcttc ttctggcttg aaaccccctc cctggatttt    1973
atagcccact taccatgcat aacagacaag tcccatattt tgtcagtaga tgcctttttt    2033
tttcgcttaa gccttaagtg ccaaatcaca agagaaaaag cagtaacagt ttacagaagc    2093
aacttagtgc cttgtaatct aactttgtca ctgtgactac attacctctt cagcgccaga    2153
gggcacccgt gggcctcccg gagcctctgc ccatggcggg gtggagaccc ggaaccagca    2213
gccccctcca ctggcgacac aactgcacct tccctcattt cagtctcccg cacacttatt    2273
cctcctcccc tcttcccggt ggcacctctc cacctgtacc gccccccacc cccccacccc    2333
ctgccccttg gaagagttgt tgccagacca gggttttggg ggaaacctgt cttgacattc    2393
aaaacctttt tcttcccgat ctgaacccct gttgactaat cttgcctggg tttgtgtagg    2453
tctgcaggaa ggaaggctga aaaagcggac gaagattttg acttaagtgg actttgtgat    2513
ttaatttttt ctttttttta agtggggagg aaggggaagc tagatggact aggagagact    2573
tgattttggt gctaaagttc cccagttcat atgtgcatc tttttaaaaa aaataacaac     2633
aaaaaaaaaa tgagagaaaa gctaaaaaaa aaaagtaag gggtgagcag ttaatggtat     2693
tcattccaca tacaatatct gtgtaaaacg atttcctgta gaagtagctt taatggtttt    2753
tgctctagaa taccgtaggt ctatccttag agcactcacg ccatgctttc ttccctgggt    2813
tttaaacttc atataacttt cagaaattgg agagcaaaaa ttttgcttgt cactgcacat    2873
caatataaaa aagcttattt aacttatcaa aacgtattta ttgccaaact atgcttttt     2933
ttgttaattt tgttcatatt tatcgggatg acaaatccat agaatatatt cttttatgtt    2993
aaattatgat cttcatatta atcttaaaat tttgtgacgt gtcttttcc tttttttcca     3053
cagttttaat atattattct tcaacgacat tttttgtaac tttacacttt tttggttatt    3113
ttattttaaa aaaatgaaaa attaatttaa aaaaatgcaa aaaactgttg gattatttat    3173
tttagaaatt ccccccttg tgttggactg caaattgagt ttctttctct ttaggccttt     3233
cacaactagg actgagaatg tatgtaaaag ttctgtgaca gtacagaagg aaaacaactt    3293
tttatgtata gcttctaaaa ggggaaaaaa aaaaaaaga gaaacccttt gacttccacg     3353
tgcccatctc aagacattcc actcacagat ttgaggttct ggattccagg tctggagttt    3413
tccaatgtta atgtaaacag aactggcaca cacacattaa gatgaatgta attattattc    3473
ctcttgctgg tcactaccgt cgctttctat ttctctttct ttgtgtgaat ttatttaaaa    3533
gaaaaaaaac ttttttgtaac gactatttgc agtttaaaaa tcaataaacc ccgttttttc   3593
aagaaacatt gatggtggag ctggttttac ttggttttgg tttgactttg ccagtaaggt    3653
tctccccttg tataccttgc aagtcctggg gaggggagg cggagagaga gggctgtggc     3713
tgtgggtggc ggcatctctc atccctataa gctaagccta tagctcccct ccttgatgct    3773
ggcagtttgc tgcacttaga ggggacgggg tggaggtttt ctgcaaagga gcctgtactt    3833
cctgctgtat tacttctgaa aagactgtgc agtgtgttag ttgttggctg aatagcagcg    3893
ggcccagcct tgccgacact tgtgtggcc                                      3922
```

<210> SEQ ID NO 19
<211> LENGTH: 319
<212> TYPE: PRT

<213> ORGANISM: Homo sapiens

<400> SEQUENCE: 19

```
Gly Asn Lys Met Leu Asn Tyr Ser Ala Pro Ser Ala Gly Gly Cys Leu
1               5                   10                  15

Leu Asp Arg Lys Ala Val Gly Thr Pro Ala Gly Gly Phe Pro Arg
            20                  25                  30

Arg His Ser Val Thr Leu Pro Ser Ser Lys Phe His Gln Asn Gln Leu
        35                  40                  45

Leu Ser Ser Leu Lys Gly Glu Pro Ala Pro Ala Leu Ser Ser Arg Asp
    50                  55                  60

Ser Arg Phe Arg Asp Arg Ser Phe Ser Glu Gly Glu Arg Leu Leu
65              70                  75                  80

Pro Thr Gln Lys Gln Pro Gly Gly Gly Gln Val Asn Ser Ser Arg Tyr
                85                  90                  95

Lys Thr Glu Leu Cys Arg Pro Phe Glu Glu Asn Gly Ala Cys Lys Tyr
            100                 105                 110

Gly Asp Lys Cys Gln Phe Ala His Gly Ile His Glu Leu Arg Ser Leu
        115                 120                 125

Thr Arg His Pro Lys Tyr Lys Thr Glu Leu Cys Arg Thr Phe His Thr
    130                 135                 140

Ile Gly Phe Cys Pro Tyr Gly Pro Arg Cys His Phe Ile His Asn Ala
145             150                 155                 160

Glu Glu Arg Arg Ala Leu Ala Gly Ala Arg Asp Leu Ser Ala Asp Arg
                165                 170                 175

Pro Arg Leu Gln His Ser Phe Ser Phe Ala Gly Phe Pro Ser Ala Ala
            180                 185                 190

Ala Thr Ala Ala Thr Gly Leu Leu Asp Ser Pro Thr Ser Ile Thr
        195                 200                 205

Pro Pro Pro Ile Leu Ser Ala Asp Leu Leu Gly Ser Pro Thr Leu
    210                 215                 220

Pro Asp Gly Thr Asn Asn Pro Phe Ala Phe Ser Ser Gln Glu Leu Ala
225             230                 235                 240

Ser Leu Phe Ala Pro Ser Met Gly Leu Pro Gly Gly Ser Pro Thr
                245                 250                 255

Thr Phe Leu Phe Arg Pro Met Ser Glu Ser Pro His Met Phe Asp Ser
            260                 265                 270

Pro Pro Ser Pro Gln Asp Ser Leu Ser Asp Gln Glu Gly Tyr Leu Ser
        275                 280                 285

Ser Ser Ser Ser Ser His Ser Gly Ser Asp Ser Pro Thr Leu Asp Asn
    290                 295                 300

Ser Arg Arg Leu Pro Ile Phe Ser Arg Leu Ser Ile Ser Asp Asp
305             310                 315
```

<210> SEQ ID NO 20
<211> LENGTH: 1510
<212> TYPE: DNA
<213> ORGANISM: Saccharomyces cerevisiae
<220> FEATURE:
<221> NAME/KEY: CDS
<222> LOCATION: (427)..(1404)

<400> SEQUENCE: 20

```
aatagaaaat tttcattttc caccttctgt tacccgagtt tatagaccta ggatttccaa    60
tcattactta ttaggacatt cgggaaaaat atacatatat ggcccacttc tctcacatct   120
```

```
                                                        -continued
cttttagggt ctgtgccaat ggcacccaaa ttttcttct ttcttttcg ctcgtattct     180 ctcacgctct tgatcagtgt gagcagttac taatatactg gatcagagaa cattaactca    240
aaggttgata gtgtagatca ttggacatag tgtgacggtt ttgcactctt gttgcgcttg    300
ctctcttaac aagtcacatc ttatttagcc tcttcaccca taagttgatt gtaaagccgt    360
agaaccctat atcacagtct cttcggcaac tcaaccaata agaactatta aggattaaca    420 ctagcc atg atg ccg aat gtt gct cca aac agc tac tat tta aac ata       468
       Met Met Pro Asn Val Ala Pro Asn Ser Tyr Tyr Leu Asn Ile
        1               5                  10 ccg aat gcc aat tcg acc tca acg act acg tcc tcg atc ttt tct gat      516
Pro Asn Ala Asn Ser Thr Ser Thr Thr Thr Ser Ser Ile Phe Ser Asp
15                  20                  25                  30 ctc aac aag gag tac gag tca aag att aaa gaa atc gaa gaa tat tat      564
Leu Asn Lys Glu Tyr Glu Ser Lys Ile Lys Glu Ile Glu Glu Tyr Tyr
                35                  40                  45 ata aag aca ctg ctc aat gaa aat acc gat aat gat gac agc agc agc      612
Ile Lys Thr Leu Leu Asn Glu Asn Thr Asp Asn Asp Asp Ser Ser Ser
            50                  55                  60 tcc gag ggg cat aat ata aat gaa acg gac att tta agt gaa tac tca      660
Ser Glu Gly His Asn Ile Asn Glu Thr Asp Ile Leu Ser Glu Tyr Ser
        65                  70                  75 cca agg cct tct cct tgg tta cca tcc aaa cca aac tgt tat cat ccg      708
Pro Arg Pro Ser Pro Trp Leu Pro Ser Lys Pro Asn Cys Tyr His Pro
    80                  85                  90 ttg gga gat ttt aaa gac ttg atc ata tca gat tcc aga cct aca aat      756
Leu Gly Asp Phe Lys Asp Leu Ile Ile Ser Asp Ser Arg Pro Thr Asn
95                  100                 105                 110 aca tta cct att aat aac cct ttc gca ggc aat aat aac atc tca aca      804
Thr Leu Pro Ile Asn Asn Pro Phe Ala Gly Asn Asn Asn Ile Ser Thr
                115                 120                 125 ctt gct aca act gag aaa aaa cgt aag aaa agg tca ctc gaa gtt aga      852
Leu Ala Thr Thr Glu Lys Lys Arg Lys Lys Arg Ser Leu Glu Val Arg
            130                 135                 140 gtt aac cct act tac acg aca agt gca ttt tca tta ccc ctg aca gcg      900
Val Asn Pro Thr Tyr Thr Thr Ser Ala Phe Ser Leu Pro Leu Thr Ala
        145                 150                 155 gag aat tta caa aaa cta tct cag gtg gat tct cag tct act gga ctt      948
Glu Asn Leu Gln Lys Leu Ser Gln Val Asp Ser Gln Ser Thr Gly Leu
    160                 165                 170 cca tac aca ctt cca att cag aaa aca aca aaa ctg gaa cct tgt aga      996
Pro Tyr Thr Leu Pro Ile Gln Lys Thr Thr Lys Leu Glu Pro Cys Arg
175                 180                 185                 190 agg gca cct ttg cag ctt cct caa tta gtc aat aag acc tta tac aaa     1044
Arg Ala Pro Leu Gln Leu Pro Gln Leu Val Asn Lys Thr Leu Tyr Lys
                195                 200                 205 act gag ctc tgt gaa tct ttt act att aaa ggc tat tgt aag tat gga     1092
Thr Glu Leu Cys Glu Ser Phe Thr Ile Lys Gly Tyr Cys Lys Tyr Gly
            210                 215                 220 aat aaa tgc caa ttt gct cat ggt ctt aat gaa ctg aaa ttc aag aaa     1140
Asn Lys Cys Gln Phe Ala His Gly Leu Asn Glu Leu Lys Phe Lys Lys
        225                 230                 235 aaa tca aac aat tat aga act aaa cct tgc ata aat tgg tcg aag tta     1188
Lys Ser Asn Asn Tyr Arg Thr Lys Pro Cys Ile Asn Trp Ser Lys Leu
    240                 245                 250 ggc tac tgt ccg tac ggt aag cgt tgc tgt ttc aaa cac ggt gat gat     1236
Gly Tyr Cys Pro Tyr Gly Lys Arg Cys Cys Phe Lys His Gly Asp Asp
255                 260                 265                 270 aag gac gtt gaa ata tat caa aat gct aac gat gga aga agt aag gat     1284
```

-continued

```
Lys Asp Val Glu Ile Tyr Gln Asn Ala Asn Asp Gly Arg Ser Lys Asp
                275                 280                 285 acg gcg ttg act cca ctt cct act tcc cta gcc cca agc aac aac gat      1332
Thr Ala Leu Thr Pro Leu Pro Thr Ser Leu Ala Pro Ser Asn Asn Asp
            290                 295                 300 aat atc act aat ttg agt aag cct agg aac tta cat act agt gtt aaa      1380
Asn Ile Thr Asn Leu Ser Lys Pro Arg Asn Leu His Thr Ser Val Lys
        305                 310                 315 gca ttg caa agg atg act tgg tag tcggtcaaca acaaagccct tgaatattt      1434
Ala Leu Gln Arg Met Thr Trp
    320                 325 ggcgtatttc tgctgcctct ccttatttat ttattcatta tcgttttcat atttatttca    1494
gtcacaaaac aaaatt                                                    1510

<210> SEQ ID NO 21
<211> LENGTH: 325
<212> TYPE: PRT
<213> ORGANISM: Saccharomyces cerevisiae

<400> SEQUENCE: 21

Met Met Pro Asn Val Ala Pro Asn Ser Tyr Tyr Leu Asn Ile Pro Asn
1               5                   10                  15

Ala Asn Ser Thr Ser Thr Thr Ser Ser Ile Phe Ser Asp Leu Asn
            20                  25                  30

Lys Glu Tyr Glu Ser Lys Ile Lys Glu Ile Glu Glu Tyr Tyr Ile Lys
        35                  40                  45

Thr Leu Leu Asn Glu Asn Thr Asp Asn Asp Asp Ser Ser Ser Ser Glu
    50                  55                  60

Gly His Asn Ile Asn Glu Thr Asp Ile Leu Ser Glu Tyr Ser Pro Arg
65                  70                  75                  80

Pro Ser Pro Trp Leu Pro Ser Lys Pro Asn Cys Tyr His Pro Leu Gly
                85                  90                  95

Asp Phe Lys Asp Leu Ile Ile Ser Asp Ser Arg Pro Thr Asn Thr Leu
            100                 105                 110

Pro Ile Asn Asn Pro Phe Ala Gly Asn Asn Ile Ser Thr Leu Ala
        115                 120                 125

Thr Thr Glu Lys Lys Arg Lys Lys Arg Ser Leu Glu Val Arg Val Asn
    130                 135                 140

Pro Thr Tyr Thr Thr Ser Ala Phe Ser Leu Pro Leu Thr Ala Glu Asn
145                 150                 155                 160

Leu Gln Lys Leu Ser Gln Val Asp Ser Gln Ser Thr Gly Leu Pro Tyr
                165                 170                 175

Thr Leu Pro Ile Gln Lys Thr Thr Lys Leu Glu Pro Cys Arg Arg Ala
            180                 185                 190

Pro Leu Gln Leu Pro Gln Leu Val Asn Lys Thr Leu Tyr Lys Thr Glu
        195                 200                 205

Leu Cys Glu Ser Phe Thr Ile Lys Gly Tyr Cys Lys Tyr Gly Asn Lys
    210                 215                 220

Cys Gln Phe Ala His Gly Leu Asn Glu Leu Lys Phe Lys Lys Lys Ser
225                 230                 235                 240

Asn Asn Tyr Arg Thr Lys Pro Cys Ile Asn Trp Ser Lys Leu Gly Tyr
                245                 250                 255

Cys Pro Tyr Gly Lys Arg Cys Cys Phe Lys His Gly Asp Asp Lys Asp
            260                 265                 270

Val Glu Ile Tyr Gln Asn Ala Asn Asp Gly Arg Ser Lys Asp Thr Ala
        275                 280                 285
```

-continued

```
            275                 280                 285
Leu Thr Pro Leu Pro Thr Ser Leu Ala Pro Ser Asn Asn Asp Asn Ile
    290                 295                 300

Thr Asn Leu Ser Lys Pro Arg Asn Leu His Thr Ser Val Lys Ala Leu
305                 310                 315                 320

Gln Arg Met Thr Trp
                325
```

MAMMALIAN CELL SURFACE DNA RECEPTOR

This application is a divisional of U.S. patent application, Ser. No. 09/921,099, filed Aug. 1, 2001, now U.S. Pat. No. 6,602,707 which application claims priority to U.S. Provisional Application Ser. No. 60/222,624, filed Aug. 1, 2000, the entirety of which is incorporated by reference.

BACKGROUND OF THE INVENTION

1. Field of the Invention

This invention relates to cell membrane-associated DNA binding proteins (termed DNA-R herein) from mammalian species and the genes corresponding to such receptors. Specifically, the invention relates to the isolation, cloning and sequencing of complementary DNA (cDNA) copies of messenger RNA (mRNA) encoding a novel mammalian DNA-R gene. The invention also relates to the construction of recombinant expression constructs comprising cDNA of this novel DNA-R gene, said recombinant expression constructs being capable of expressing DNA-R protein in cultures of transformed prokaryotic and eukaryotic cells. Production of the receptor protein in such cultures is also provided, as well as the production of fragments thereof having biological activity. The invention relates to the use of such cultures of such transformed cells to produce homogeneous compositions of the novel DNA-R protein. The invention also provides cultures of such cells producing this DNA-R protein for the characterization of novel and useful drugs. Antibodies against and epitopes of this novel DNA-R protein are also provided by the invention.

2. Background of the Invention

Extracellular DNA is a potent biological signal, being capable of initiating a wide range of immune responses in vivo and in vitro; including cytokine production, influx of neutrophils, IgM secretion, B-cell proliferation and enhanced natural killer activity. These properties of extracellular DNA enable naked DNA to be used as vaccines, in some instances. In addition, extracellular DNA has been used to introduce new genetic information into cells, both in vivo and in vitro.

One important aspect of extracellular DNA transfer into mammalian cells is gene therapy. Gene transfer therapy offers the potential for treatment of a variety of diseases. The ability to provide safe, efficient, and selective in vivo gene delivery will be a critical component of future protocols. Gene transfer by injection of either plasmid DNA or DNA/liposome complexes has been demonstrated to be safe and permits expression of gene products. The uptake of DNA/liposome complexes does not depend upon specific cell-surface receptors while the mechanism mediating uptake of plasmid DNA by cells remains unknown.

In order to realize the full potential of this technology, safe delivery and efficient transgene expression of DNA in selected tissues and cells must be achieved. One approach to target DNA to tissue is the use of a receptor-mediated mechanism for the binding and internalization of DNA. Viral (retrovirus, adenovirus, adeno-associated virus) delivery of DNA to cells is via a receptor-mediated mechanism, however this technique has limited in vivo clinical application. Viral vectors have been most frequently used for ex vivo gene therapy, but the technical problems associated with transplanting transduced cells remain a serious obstacle. In addition, viral vectors have the potential to lead to virus infection or to induce an immune response against antigenic viral coat proteins.

Non-viral methods of gene delivery include liposomes, the so-called "gene gun", and direct injection. Gene transfer with liposomes has been shown to result in uptake and expression of DNA. Although DNA/liposomes are effectively taken up and the cDNA on the plasmid expressed, the process is believed to be nonspecific with limited possibility of targeting selected tissue. An alternative is to administer plasmid DNA directly, without a delivery system. Cells lines in tissue culture have demonstrated in vitro uptake of plasmid DNA and the expression of the transgene on the plasmid. It has also been shown that DNA, injected directly in vivo, has been taken up and the encoded genes have been expressed. While this approach has been shown to be a safe and free from problems associated with DNA delivery by viruses, the therapeutic potential of this technology is often limited by poor transgene expression from plasmid DNA in many tissues. In addition, the mechanism by which plasmid DNA is bound and internalized into cells is not well established. Knowledge of the mechanism of plasmid DNA binding to the cell surface, and how DNA is internalized and expressed, will be critical to enhancing transgene methods that also have the potential to target selected tissues.

Antisense oligonucleotides (ODN) are another form of extracellular DNA of great importance. ODN are considered potential therapeutic agents against various pathogens and oncogenes due to their ability to specifically inhibit gene expression. When injected into tissues, ODN are internalized by cells and bind to complementary region of mRNA to inhibit translation of proteins in a highly specific manner. Different antisense ODN to HIV RNA have been shown to inhibit the infectivity of the virus in cultured human leukemia cells. Although human clinical trials using ODN to treat AIDS and other diseases are ongoing, the lack of a precise understanding of where and how gene expression is effected hinders the optimization of this technique.

Extracellular DNA is also associated with human diseases, such as cystic fibrosis. Cystic fibrosis (CF) is the most common lethal genetic disease in North America. It affects one in 2500 live births and affected individuals have a median life expectancy of 28 years (Davis et al., 1996, *Amer. J. Respir. Crit Care Med.* 157: 1234–1239). There is a growing body of evidence showing that inflammation, particularly the injurious products of neutrophils, may be responsible for lung damage (Doring, 1997, *Ped. Pulmonol. Supp.* 16: 271–272); it is now recognized that most of the morbidity and over 90% of the mortality results from chronic progressive inflammation of the lungs. Corticosteroids have abroad anti-inflammatory effect, particularly on neutrophils. A multicenter trial showed beneficial effects of oral corticosteroids on lung function. However, adverse effects such as growth retardation, glucose abnormalities and cataracts prelude this treatment as a long-term option (Eigen et al., 1995, *J. Ped.* 126: 515–523). The nonsteroidal anti-inflammatory drug, ibuprofen, has also been studied (Konstan et al., 1995, *N. Engl. J. Med.* 332: 848–854). The drug is beneficial, but continued monitoring is needed to determine the safety of long-term, high dose therapy. Other therapies that treat the injurious products of neutrophils, for example, antiproteases and antioxidants, are currently under investigation (Konstan, 1998, *Clin. Chest Med.* 19: 505–513).

The vicious airway fluid characteristic of CF can obstruct airflow and provides a viable growth medium for pathogenic bacteria, and cell lysis of these bacteria can produce extracellular DNA that causes inflammation. Recombinant human Dnase (rhDNase) has been clinical use since 1994 (Kontsan, 1998, ibid.). The rhDNase, administered by inhalation, has been used to cleave the extracelular airway DNA and reduce the viscosity of the airway fluid. Treatment with rhDNase produces a small improvement in lung function (Cramer & Bosso, 1996, *Ann. Pharmacol.* 30: 656–661). However, when treatment is stopped, patients can deteriorate to a point below their previous baseline (Bush, 1998, *Ped. Pulmonol.* 25: 79–82). In addition, a recent report showed that despite improvements in lung function, there were no changes in airway inflammation (Henry et al., 1998, *Ped. Pulmonol.* 26: 97–100). Although the DNA is broken down by the Dnase, it is not entirely degraded, and hydrolized fragments are still potentially immunostimulatory and can contribute to inflammation. Thus rhDNase may be masking the process of on-going lung destruction.

There are also a variety of conventional treatments for CF including physiotherapy, nutritional support and drugs (Bilton & Mahadeva, 1997, *J. Royal Soc. Med.* 90: Suppl. 31,2–5). Because the events that trigger and sustain inflammation in patients with CF are not clearly understood, a variety of approaches have been developed to treat different components of the disease. Antibiotics, anti-inflammatories, and therapies to reduce the viscosity of the airway fluid are all approaches that are being used and investigated. Aggressive antibiotic therapy has helped the acute control of infection, but rarely if ever are the bacteria in the airways of patients with CF completely eradicated. These pathogenic bacteria chronically stimulate and exacerbate inflammation. Although some of the currently-available treatments can help to alleviate symptoms and slow the progression of disease, none of the current treatments can prevent ultimate respiratory failure.

One important clinical observation is that greatly increased amounts of extracellular DNA, of host and bacterial origin, are present in the airway of patients with cystic fibrosis. Recent investigation has demonstrated that extracellular DNA, purified from sputum of patients with CF, will directly induce inflammation in the mouse lung (Schwartz et al., 1997, *J. Clin. Invest.* 100: 68–73). The DNA purified from the sputum of patients with cystic fibrosis has been shown to be composed primarily of host-derived DNA and only a small fraction appears to be bacterial DNA (Schwartz et al., 1997, ibid.). One possible explanation is that extracellular DNA binds to immune lung cells in the lungs and induces the secretion of pro-inflammatory cytokines and neutrophic migration to the lung, leading to severe airway inflammation. Extracellular DNA binding to immune cells in the lung, such as alveolar macrophages are stimulated to produce pro-inflammatory cytokines that recruit and activate neutrophils leading to inflammation. When these neutrophils undergo apoptosis and release their DNA the cycle is repeated and inflammation is maintained or increased. Thus, methods and reagents that block DNA binding to cytokine producing cells may therefore provide better treatment of CF patients than are currently available.

Although there have been several reports in the art that DNA could bind to cell surfaces (Bennett, 1993, *Antisense Res. Develop.* 3: 235–241; Bennett et al., 1986, *J. Rheumatol.* 13: 679–685; Gabor & Bennett, 1984, *Biochem Biophys. Res. Commun.* 122:1034–1039; Hefeneider et al., 1990, *J. Invest. Dermatol.* 94: 79S–84S; Bennett et al., 1987, *J. Exp. Med.* 166: 850–863; Bennett et al., 1991, *Clin. Exp. Immunol.* 86:374–379; Bennett et al., 1992, *Clin. Exp. Immunol* 90: 428–433; Bennett et al., 1985, *J. Clin. Invest.* 76: 2182–2190; Hefeneider et al., 1992, *Lupus* 1: 167–173; Hefeneider et al., 1992, *Clin. Immunol. Immunopath.* 63: 245–251; Reid & Chalson, 1979, *Intl. Rev. Cytol.* 60: 27–52; Lerner et al., 1971, *Proc. Natl. Acad. Sci. USA* 68: 1212–1216; Pancer et al., 1981, *J. Immunol.* 127: 98–104; Meinke & Goldstein, 1974, *J. Molec. Biol.* 86: 757–773; Sudar et al., 1986, *Cell. Molec. Biol.* 32: 87–91; Gasparro et al., 1990, *Photochem & Photobiol.* 52: 315–321; Emlen et al., 1988, *Amer. J. Pathol.* 133: 54–60), the art lacks an understanding of how cells mediate extracellular DNA binding. Thus, an understanding of the mechanisms by which eukaryotic cells, particularly mammalian cells, take up extracellular DNA would be important in improving a variety of biological processes.

SUMMARY OF THE INVENTION

The present invention relates to the cloning, expression and functional characterization of a mammalian DNA-R gene. The invention comprises nucleic acids having a nucleotide sequence of a novel mammalian DNA-R gene. The nucleic acids provided by the invention comprise a complementary DNA (cDNA) copy of the corresponding mRNA transcribed in vivo from the DNA-R genes of the invention. In a preferred embodiment, the mammalian DNA-R is a human DNA-R. Also provided are the deduced amino acid sequence of the cognate proteins of the cDNAs provided by the invention, methods of making said cognate proteins by expressing the cDNAs in cells transformed with recombinant expression constructs comprising said cDNAs, and said recombinant expression constructs and cells transformed thereby.

This invention in a first aspect provides nucleic acids, nucleic acid hybridization probes, recombinant eukaryotic expression constructs capable of expressing the DNA-Rs of the invention in cultures of transformed cells, and such cultures of transformed eukaryotic cells that synthesize the DNA-Rs of the invention. In another aspect, the invention provides homogeneous compositions of the DNA-R proteins of the invention, homogeneous compositions of fragments of said DNA-R, most preferably a fragment comprising amino acids 1–575 of the DNA-R, as well as fusion proteins between the DNA-R or fragments thereof and, inter alia, epitope markers, and membrane preparations from cells expressing the DNA-R proteins of the invention, and also antibodies against and epitopes of the DNA-R proteins or fragments thereof of the invention. The invention in another aspect provides methods for making said homogenous preparations and membrane preparations using cells transformed with the recombinant expression constructs of the invention and expressing said DNA-R proteins thereby. Methods for characterizing the receptor and biochemical properties of these receptor proteins and methods for using these proteins in the development of agents having pharmacological uses related to the DNA-R of the invention are also provided.

In a first aspect, the invention provides a nucleic acid having a nucleotide sequence encoding a mammalian DNA-R. In a first preferred embodiment, the nucleic acid encodes a human DNA-R. In this embodiment of the invention, the nucleotide sequence comprises 4351 nucleotides of human DNA-R cDNA comprising 3576 nucleotides of coding sequence, 601 nucleotides of 5' untranslated sequence and 177 nucleotides of 3' untranslated sequence. In this embodiment of the invention, the nucleotide sequence of the DNA-R is the nucleotide sequence depicted in FIG. 1 (SEQ ID No:1). The sequence shown in FIG. 1 will be understood to represent one specific embodiment of a multiplicity of nucleotide sequences that encode the human DNA-R amino acid sequence of 1192 amino acids (SEQ ID No.:2) of the invention and that these different nucleotide sequences are functionally equivalent and are intended to be encompassed by the claimed invention. In addition, it will be understood that different organisms and cells derived therefrom express preferentially certain transfer RNAs (tRNAs) corresponding to subsets of the degenerate collection of tRNAs capable of encoding certain of the naturally-occurring amino acids, and that embodiments of the multiplicity of nucleotide sequences encoding the amino acid sequence of the human DNA-R protein of the invention that are optimized for expression in specific prokaryotic and eukaryotic cells are also encompassed by the claimed invention. Isolated nucleic acid derived from human genomic DNA and isolated by conventional methods using the human cDNA provided by the invention is also within the scope of the claimed invention. Finally, it will be understood that allelic variations of the human DNA-R, including naturally occurring and in vitro modifications thereof are within the scope of this invention. Each such variant will be understood to have essentially the same amino acid sequence as the sequence of the human DNA-R disclosed herein.

Mammalian DNA-R proteins corresponding to the-human cDNA of the invention are a second aspect of the claimed invention. In a first embodiment, the mammalian DNA-R protein is a human DNA-R having a deduced amino acid sequence shown in FIG. 1 (SEQ ID No.:2). In a second embodiment is provided said human DNA-R protein comprising a membrane preparation from a cell, most preferably a recombinant cell, expressing a nucleic acid encoding a human DNA-R of the invention.

As provided in this aspect of the invention is a homogeneous composition of a mammalian DNA-R having a molecular weight of about 150 kD or derivative thereof that is a human DNA-R having an amino acid sequence shown in FIG. 1 and identified by SEQ ID No.:2, said size being understood to be the predicted size of the protein before any post-translational modifications thereof. Also provided is a homogeneous composition of An amino-terminal fragment of the human DNA-R comprising amino acid residues 1–575 of the sequence identified as SEQ ID No.: 2. Species of the protein genetically engineered to lack the transmembrane region of the DNA-R as described herein, and thereby providing soluble forms of the DNA-R of the invention, are also within the scope of this aspect of the invention and are provided herein.

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone of the invention encoding a mammalian DNA-R or fragment thereof, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the DNA-R gene in various tissues of mammals, including humans. It is also an object of the present invention to provide nucleic acid hybridization probes derived from the sequences of mammalian DNA-R genes of the invention to be used for the detection and diagnosis of genetic diseases. It is an object of this invention to provide nucleic acid hybridization probes derived from the nucleic acid sequences of the mammalian DNA-R genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of DNA-R-specific antibodies, or useful as competitors of DNA-R molecules for nucleic acid binding, or to be used for the production of inhibitors of nucleic acid binding to such DNA-R molecules.

The present invention also provides antibodies against and epitopes of the mammalian DNA-R molecules of the invention. It is an object of the present invention to provide antibodies that are immunologically reactive to the DNA-Rs of the invention. It is a particular object to provide monoclonal antibodies against these DNA-Rs. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of a mammalian DNA-R of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the mammalian DNA-R proteins of the invention. Chimeric antibodies immunologically reactive against the DNA-R proteins of the invention are also within the scope of this invention.

The present invention provides recombinant expression constructs comprising a nucleic acid encoding a mammalian DNA-R of the invention wherein the construct is capable of expressing the encoded DNA-R in cultures of cells transformed with the construct. A preferred embodiment of such constructs comprises a human DNA-R cDNA depicted in FIG. 1 (SEQ ID No.:1), such constructs being capable of expressing the human DNA-R encoded therein in cells transformed with the construct. Also provided are recombinant expression constructs encoding fragments of said DNA-R, most preferably an amino-terminal fragment comprising amino acid residues 1–575 and fragments genetically engineered to lack the transmembrane domain of said DNA-R, there by providing for production of soluble forms of the DNA-R In alternative embodiments, the recombinant expression construct encodes a DNA-R fused to epitope sequences recognized by conventional antibodies known in the art. In each instantce, the recombinant expression constructs of the invention are capable of expressing the human DNA-R encoded therein or fragment thereof in cells transformed with the construct.

The invention also provides prokaryotic and more preferably eukaryotic cells transformed with the recombinant expression constructs of the invention, each such cells being capable of and indeed expressing the mammalian DNA-R or fragment or epitope-modified species encoded in the transforming construct, as well as methods for preparing mammalian DNA-R proteins using said transformed cells.

The present invention also includes within its scope protein preparations of prokaryotic and eukaryotic cell membranes containing the DNA-R protein of the invention, or fragment or epitope-modified species thereof, derived from cultures of prokaryotic or eukaryotic cells, respectively transformed with the recombinant expression constructs of the invention.

The invention also provides methods for screening compounds for their ability to inhibit, facilitate or modulate the biochemical activity of the mammalian DNA-R molecules of the invention, in particular nucleic acid binding thereto. In preferred embodiments, the methods of the invention relate to binding of DNA, particularly double-stranded DNA, and oligonucleotides. The methods of the invention are particularly directed towards identifying compounds that influence DNA or oligonucleotide uptake into cells expressing the DNA-R. In preferred embodiments, the compounds identified by the methods of the invention influence DNA or oligonucleotide uptake by pinocytosis or endocytosis. In preferred embodiments, the compounds influence DNA or oligonucleotide uptake by increasing the amount of DNA or oligonucleotide that reaches the nucleus of the cell in a form that can be expressed therein. Preferred compounds of the invention are identified by detecting increased uptake or increased expression of a gene, most preferably a reporter gene, encoded by said DNA. In preferred embodiments, cells transformed with a recombinant expression construct of the invention are contacted with such a compound, and the amount of DNA or oligonucleotide taken up by the cell, or the frequency or amount of gene expression, most preferably reporter gene expression, in the cell is assayed.

Specific preferred embodiments of the present invention will become evident from the following more detailed description of certain preferred embodiments and the claims.

DESCRIPTION OF THE DRAWINGS

The patent or application file contains at least one drawing executed in color. Copies of this patent or patent application publication with color drawing(s) will be provided by the Office upon request and payment of the necessary fee.

An understanding of the invention is facilitated by reference to the drawings.

FIG. 4A is an alignment of conserved cysteines, histidines and aspartic acids of Membrane-associated DNA binding protein of the invention (MNAB, amino acid No. 9 to 58 of SEQ ID No.2), the C3HC3D RING finger in Homo sapiens ARD1 GTP-binding protein (Gene Bank Accession 422756; amino acid No. 26 to 80 of SEQ ID No.7), H. sapiens CART1 protein (Gene Bank Accession 951276, SEQ ID No.12; amino acid No. 13 to 62 of SEQ ID No.13), H. sapiens SBBI03 hypothetical protein (Gene Bank Accession 5032071; amino acid No. 13 to 61 of SEQ ID No:8), Caenorhabditis elegans cDNA EST (Gene Bank Accession 3879246; amino acid No. 130 to 182 of SEQ ID No.9), C. elegans hypothetical 25.8 KD protein (Gene Bank Accession 2496825; amino acid No. 150 to 199 of SEQ ID NO.10) C. elegans cDNA EST (Gene Bank Accession 3878739; amino acid No. 11 to 61 of SEQ ID No.11).

FIG. 4B is an alignment of conserved cysteines and histidines of the C3H type zinc finger in Membrane-associated DNA binding protein of the invention (MNAB, amino acid No. 401 to 448 of SEQ ID No.2), C. elegans PIE-1 (Gene Bank U62896, SEQ ID No.14; amino acid No. 96 to 136 of SEQ ID No.15), Drosophila melanogaster DTIS 11 (Gene Bank U13397, SEQ ID No.16; amino acid No. 130 to 166 of SEQ ID No.17), H sapiens TIS11B Buryrate response factors (EFT-Response factor) (Gene Bank X79067, second exon, SEQ ID No.18; amino acid No. 93 to 125 of SEQ ID No.19), Saccharomyces cerevisiae CTH1 Zinc finger protein (Gene Bank L42133, SEQ ID No.20; amino acid No. 195 to 235 of SEQ ID No.21).

In FIG. 17A (left panel), A549 cells were incubated with YOYO/pGEM4Z in the presence (solid line) and absence (dashed line) of a 25–100 fold excess calf thymus DNA for 2 hr at 4° C. In FIG. 17B (right panel), specific DNA binding to A549 cells is shown as the difference in fluorescence intensity of YOYO/pGEM4Z bound to the cells using the data from the left panel. Data are the mean±SEM of 4–9 determinations.

The cells were then washed (binding) or trypsinized and washed (uptake), and the fluorescence measured by FACS.

Figure 24:
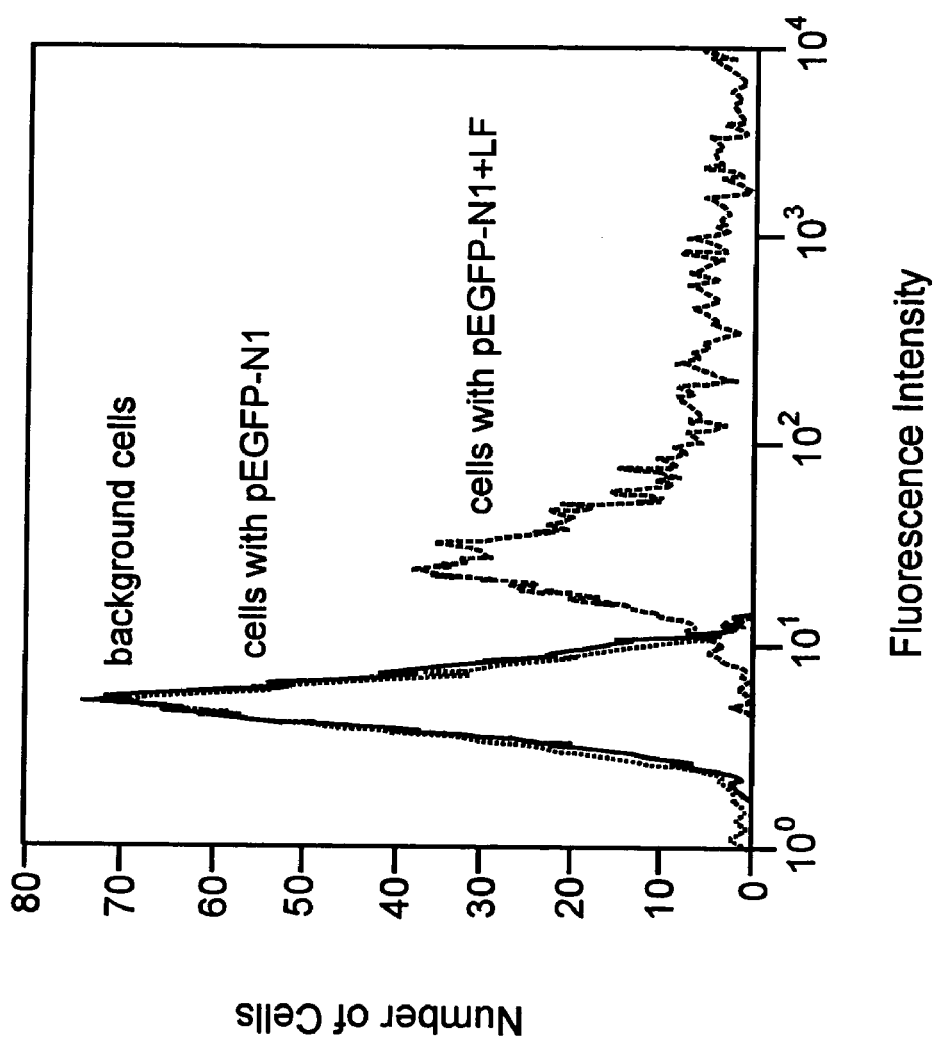

FIG. 24 shows expression in B16 cells of green fluorescence protein (GFP) transgene from plasmid DNA. Cells were incubated with 12 µg/mL pEGFP-N1 for 6 hr. After 48 hr the cells were trypsinized and fluorescence measured by FACS. Control cells incubated without DNA and cells treated with pEGFP-N1 without carrier showed similar fluorescence, whereas cells incubated with pEGFP-N1 complexed with lipofectamine showed increased fluorescence.

Figure 25:
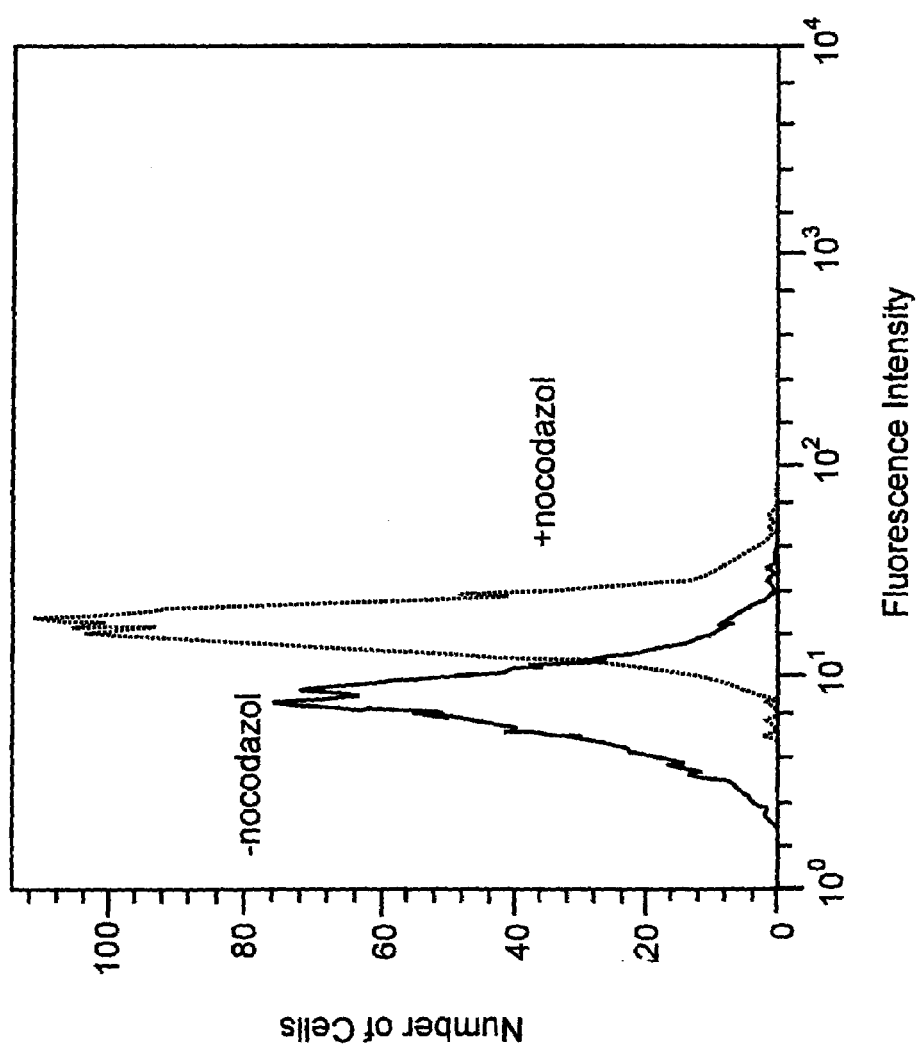

FIG. 25 show that nocodazole increases GFP transgene expression from plasmid DNA in A549 cells. A549 cells were incubated for 5 hr at 37° C. with 25 µg/mL of pEGFP-N1 in the presence (dashed line) and absence (solid line) of 33 µM nocodazole. After 24 hr the cells were trypsinized and fluorescence measured by FACS.

DETAILED DESCRIPTION OF THE PREFERRED EMBODIMENTS

Figure 1:
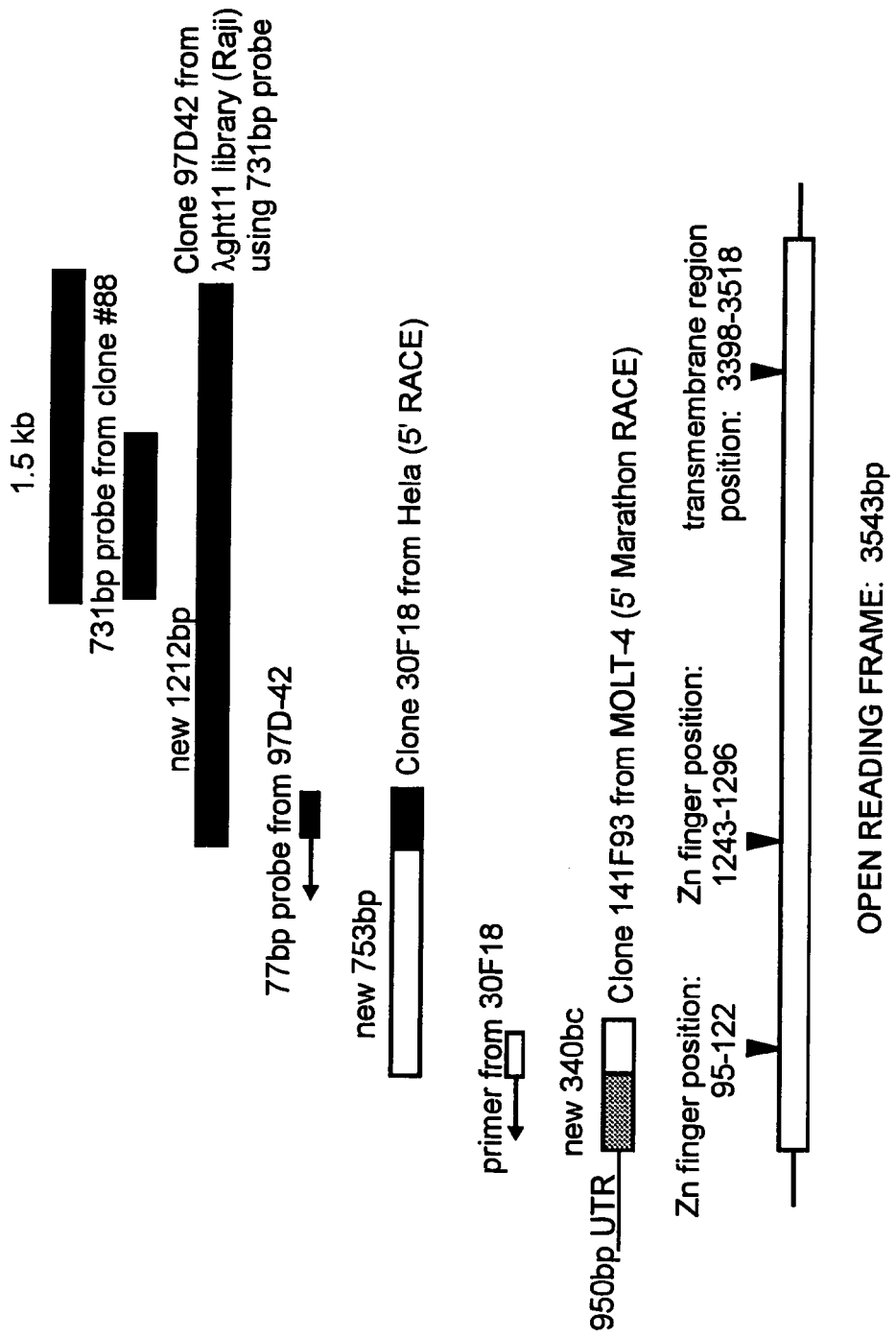
FIG. 1 is a schematic diagram illustrating cloning of the cDNA for the DNA-R of the invention. Antisera from a patient with systemic lupus erythroblastosis (SLE) and that inhibits cell surface DNA binding was used to screen λgt11 library from peripheral blood mononuclear cells. A positive clone (clone #88) containing an open reading frame (ORF) was obtained; the open reading frame remained open at the 5' end of the clone. Analysis of the nucleotide sequence of the clone identified a transmembrane region on the 3' end of the clone. A 731 bp probe from was used to screen a λgt11 cDNA library made from Raji cell line (human lymphoma cell line). Clone 97D42 which contained 462 bp of additional 5' ORF sequence was obtained from this clone. A modification of the polymerase chain reaction (5'random amplification of cDNA ends (RACE-PCR) was used to obtain the remainder of the 5' sequences from HeLa (human cervix carcinoma) and MOLT-4 (human lymphoblastic leukemia) cell lines. This sequence was compiled to produce an ORF of 3543 bp that encoded a protein with a calculated molecular weight of 130.5 kDa.

The term "mammalian DNA-R" as used herein refers to proteins consisting essentially of, and having substantially the same biological activity as, the protein encoded by the amino acid depicted in FIG. 1 (SEQ ID No.:2); This definition is intended to encompass natural allelic variations in the disclosed DNA-R. Cloned nucleic acid provided by the present invention may encode DNA-R protein of any species of origin, including, for example, mouse, rat, rabbit, cat, and human, but preferably the nucleic acid provided by the invention encodes DNA-Rs of mammalian, most preferably human, origin.

The nucleic acids provided by the invention comprise DNA or RNA having a nucleotide sequence encoding a mammalian DNA-R. Specific embodiments of said nucleic acids are depicted in FIG. 1 (SEQ ID No.:1), and include any nucleotide sequence encoding a mammalian DNA-R having an amino acid sequence as depicted in FIG. 1 (SEQ ID No.: 2). Nucleic hybridization probes as provided by the invention comprise any portion of a nucleic acid of the invention effective in nucleic acid hybridization under stringency conditions sufficient for specific hybridization. Mixtures of such nucleic acid hybridization probes are also within the scope of this embodiment of the invention. Nucleic acid probes as provided herein are useful for isolating mammalian species analogues of the specific embodiments of the nucleic acids provided by the invention. Nucleic acid probes as provided herein are also useful for detecting mammalian DNA-R gene expression in cells and tissues using techniques well-known in the art, including but not limited to Northern blot hybridization, in situ hybridization and Southern hybridization to reverse transcriptase-polymerase chain reaction product DNAs. The probes provided by the present invention, including oligonucleotides probes derived therefrom, are also useful for Southern hybridization of mammalian, preferably human, genomic DNA for screening for restriction fragment length polymorphism (RFLP) associated with certain genetic disorders.

The production of proteins such as mammalian DNA-R from cloned genes by genetic engineering means is well known in this art. The discussion which follows is accordingly intended as an overview of this field, and is not intended to reflect the full state of the art.

Nucleic acid encoding a DNA-R may be obtained, in view of the instant disclosure, by chemical synthesis, by screening reverse transcripts of mRNA from appropriate cells or cell line cultures, by screening genomic libraries from appropriate cells, or by combinations of these procedures, in accordance with known procedures as illustrated below. Screening of mRNA or genomic DNA may be carried out with oligonucleotide probes generated from the nucleic acid sequence information from mammalian DNA-R nucleic acid as disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, mammalian DNA-R nucleic acid sequences may be obtained by use of the polymerase chain reaction (PCR) procedure, using PCR oligonucleotide primers corresponding to nucleic acid sequence information derived from a DNA-R as provided herein. See U.S. Pat. No. 4,683,195 to Mullis et al. and U.S. Pat. No. 4,683,202 to Mullis.

Mammalian DNA-R protein may be synthesized in host cells transformed with a recombinant expression construct comprising a nucleic acid encoding the DNA-R nucleic acid, comprising genomic DNA or cDNA. Such recombinant expression constructs can also be comprised of a vector that is a replicable DNA construct. Vectors are used herein either to amplify DNA encoding a DNA-R and/or to express DNA encoding a DNA-R gene. For the purposes of this invention, a recombinant expression construct is a replicable DNA construct in which a nucleic acid encoding a DNA-R is operably linked to suitable control sequences capable of effecting the expression of the DNA-R in a suitable host.

The need for such control sequences will vary depending upon the host selected and the transformation method chosen. Generally, control sequences include a transcriptional promoter, an optional operator or enhancer sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 2001, *Molecular Cloning: A Laboratory Manual* (Cold Spring Harbor Press: New York).

Vectors useful for practicing the present invention include plasmids, viruses (including phage and mammalian DNA and RNA viruses), retroviruses, and integratable DNA fragments (i.e., fragments integratable into the host genome by homologous recombination). The vector can replicate the gene of interest and function independently of the host genome, or can, in some instances, integrate into the genome itself. Suitable vectors will contain replicon and control sequences which are derived from species compatible with the intended expression host. Transformed host cells are cells which have been transformed or transfected with recombinant expression constructs made using recombinant DNA techniques and comprising nucleic acid encoding a DNA-R protein. Preferred host cells are HEK293 cells, COS-7 cells (Gluzman, 1981, Cell 23:175–182) and Ltk⁻ cells. Transformed host cells may express the DNA-R protein, but host cells transformed for purposes of cloning or amplifying nucleic acid hybridization probe DNA need not express the receptor. When expressed, the DNA-R of the invention will typically be located in the host cell membrane. Accordingly, the invention provides preparations of said cell membranes comprising the DNA-R protein of the invention, as well as purified, homogeneous preparations of the receptor protein itself. See, Sambrook et al., ibid.

Cultures of cells derived from multicellular organisms are a desirable host for recombinant DNA-R protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human embryonic kidney (HEK) 293 cells, VERO and HeLa cells, Chinese hamster ovary (CHO) cell lines, mouse Ltk⁻ cell lines and WI138, BHK, COS-7, CV, and MDCK cell lines. HEK293 cell, COS-7 cells and Ltk⁻ cells are preferred.

The invention provides homogeneous compositions of mammalian DNA-R protein produced by transformed eukaryotic cells as provided herein. Each such homogeneous composition is intended to be comprised of a DNA-R protein that comprises at least 75%, more preferably at least 80%, and most preferably at least 90% of the protein in such a homogenous composition; in said homogeneous preparations, individual contaminating protein species are expected to comprise less than 5%, more preferably less than 2% and most preferably less than 1% of the preparation. The invention also provides membrane preparations from cells expressing mammalian DNA-R protein as the result of transformation with a recombinant expression construct, as described herein. Also specifically provided by the invention are fragments of the DNA-R of the invention, most preferably DNA binding fragments thereof. In preferred embodiments, said fragments include soluble forms of the receptor lacking the transmembrane domain and an amino-terminal fragment (most preferably amino acids 1–575) comprising zinc finger and RING sequence motifs known in the art to be related to DNA-protein binding.

Mammalian DNA-R proteins made from cloned genes in accordance with the present invention may be used for screening compounds that effect DNA binding to cells in vivo and in vitro, as more fully described herein, and that affect DNA uptake and expression of genes encoded thereby. For example, host cells may be transformed with a recombinant expression construct of the present invention, a mammalian DNA-R expressed in those host cells, and the cells or membranes thereof used to screen compounds for their effect on DNA binding. By selection of host cells that do not ordinarily express a DNA-R, pure preparations of membranes containing the receptor can be obtained.

The recombinant expression constructs of the present invention are useful in molecular biology to transform cells which do not ordinarily express a DNA-R to thereafter express this receptor. Such cells are useful as intermediates for making cell membrane preparations useful for receptor binding activity assays, which are in turn useful for drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful drugs synthesized, discovered or extracted from natural sources each year. This utility thereby enables rational drug design of novel therapeutically-active drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165–174).

The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Nucleic acid and oligonucleotide probes as provided by the present invention are useful as diagnostic tools for probing DNA-R gene expression in tissues of humans and other animals. For example, tissues are probed in situ with oligonucleotide probes carrying detectable groups by conventional autoradiographic or other detection techniques, to investigate native expression of this receptor or pathological conditions relating thereto. Further, chromosomes can be probed to investigate the presence or absence of the corresponding DNA-R gene, and potential pathological conditions related thereto. Oligonucleotides, particularly antisense oligonucleotides, are also useful for decreasing expression of the DNA-R in cells that overexpress the receptor or whose expression is disadvantageous in a host organism, either generally or in specific tissues. An example of the latter instance is in airway epithelial cells and macrophages in lung tissues in cystic fibrosis patients, as set forth more fully herein.

The invention also provides antibodies that are immunologically reactive to the DNA-R protein or epitopes thereof provided by the invention. The antibodies provided by the invention may be raised, using methods well known in the art, in animals by inoculation with cells that express a DNA-R or epitopes thereof, cell membranes from such cells, whether crude membrane preparations or membranes purified using methods well known in the art, or purified preparations of proteins, including protein fragments and fusion proteins, particularly fusion proteins comprising epitopes of the DNA-R protein of the invention fused to heterologous proteins and expressed using genetic engineering means in bacterial, yeast or eukaryotic cells, said proteins being isolated from such cells to varying degrees of homogeneity using conventional biochemical methods. Synthetic peptides made using established synthetic methods in vitro and optionally conjugated with heterologous sequences of amino acids, are also encompassed in these methods to produce the antibodies of the invention. Animals that are useful for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the DNA-R provided by the invention, or more preferably any cell or cell line that expresses the DNA-R of the invention, or any epitope thereof, as a result of molecular or genetic engineering, or that has been treated to increase the expression of an endogenous or heterologous DNA-R protein by physical, biochemical or genetic means. Preferred cells are mammalian cells, most preferably cells syngeneic with a rodent, most preferably a mouse host, that have been transformed with a recombinant expression construct of the invention encoding a DNA-R protein, and that express the receptor therefrom.

The present invention also provides monoclonal antibodies that are immunologically reactive with an epitope derived from a DNA-R of the invention, or fragment thereof, present on the surface of such cells or in membrane preparations thereof or used after varying degrees of biochemical purification. Particularly useful are soluble fragments of the DNA-R of the invention, including for example species of the receptor genetically engineered to remove the transmembrane domain, and amino-terminal fragments, most preferably DNA binding fragments of the receptor. Such antibodies are made using methods and techniques well known to those of skill in the art. Monoclonal antibodies provided by the present invention are produced by hybridoma cell lines, which are also provided by the invention and are made by methods well known in the art.

Hybridoma cell lines are made by fusing individual cells of a myeloma cell line with spleen cells derived from animals immunized with cells expressing a DNA-R of the invention, as described above. The myeloma cell lines used in the invention include lines derived from myelomas of mice, rats, hamsters, primates and humans. Preferred myeloma cell lines are from mouse, and the most preferred mouse myeloma cell line is P3×63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid receptor of the invention. The present invention also encompasses antigen-binding fragments, including but not limited to $F_v$, F(ab) and F(ab)$'_2$ fragments, of such antibodies. Fragments are produced by any number of methods, including but not limited to proteolytic or chemical cleavage, chemical synthesis or preparation of such fragments by means of genetic engineering technology. The present invention also encompasses single-chain antibodies that are immunologically reactive with an epitope of a DNA-R, made by methods known to those of skill in the art.

The present invention also encompasses an epitope of a DNA-R of the invention, comprised of sequences and/or a conformation of sequences present in the receptor molecule. This epitope may be naturally occurring, or may be the result of chemical or proteolytic cleavage of a receptor molecule and isolation of an epitope-containing peptide or may be obtained by chemical or in vitro synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a DNA-R-derived epitope. The chimeric antibodies embodied in the present invention include those that are derived from naturally occurring antibodies as well as chimeric antibodies made by means of genetic engineering technology well known to those of skill in the art.

Nucleic acids encoding the receptor, the DNA-R and DNA-binding fragments thereof, are advantageously used to modulate expression or activity of the receptor in cells in vivo and in vitro. As provided herein, the DNA-R of the invention, particularly soluble embodiments thereof, can competitively bind DNA to reduce said binding to cells expressing the DNA-R. DNA binding to the DNA-R in certain cells, such as airway epithelial cells and macrophages in lung, is associated with the activation of inflammatory processes that cause a significant proportion of the morbidity and mortality associated with cystic fibrosis, chronic bronchitis and other chronic lung diseases. Thus, the invention provides a variety of methods for reducing said morbidity and mortality by interfering with DNA binding to cells in the lung. In one embodiment, soluble DNA-R species can be administered, most preferably by aerosol administration using formulations, excipients and vehicles well known in the art, directly to lung tissue, and competitive DNA binding achieved thereby. In alternative embodiments, antisense oligonucleotides can be delivered to lung tissue, most preferably by aerosol administration, and expression of the DNA-R in target cells of the lung repressed thereby. In further alternatives, antibodies, most preferably monoclonal antibodies, that specifically inhibit DNA binding to the DNA-R of the invention can be used to inhibit DNA binding to said lung cells.

The DNA-R of the invention, particularly soluble embodiments and DNA-binding fragments thereof, are also useful in treating other inflammation-associated diseases and conditions, including otitis media, septic arthritis and any bacterial or viral infection that causes inflammation by interaction with the DNA-R Additionally, the DNA-R of the invention can be used to screen compounds that modulate DNA binding, uptake and expression. Introduction of DNA, particularly DNA encoding a desired gene, is a methodology well known in the art. However, DNA introduction methods have been developed empirically and without any understanding of the molecular bases of DNA uptake. Specifically, heretofore specific DNA binding to a DNA-R as disclosed herein and uptake thereby by endocytosis was unappreciated in the art. Identification of the DNA-R of the invention thus provides a novel target for developing compounds and methods for increasing efficiency of DNA uptake and expression of genes encoded thereby.

Another advantageous method provided by this invention is the use of DNA-R expressed in tumor cells to facilitate delivery of DNA-binding anticancer drugs to tumor cells. Drugs such as Adriamycin (Doxorubicin) are in clinical use for the treatment of cancer patients. Enhanced extracellular DNA uptake in tumor cells expression the DNA-R of the invention would facilitate uptake of such DNA-binding anticancer drugs by using extracellular DNA as a carrier of the drug into the cell. The association of the drug with the extracellular DNA might enable the drug to avoid active efflux produced in tumor cells, inter alia, by drug resistance mediators such as P-glycoprotein. Employing the same rationale as with gene transfer, the selective augmentation of DNA binding receptors on tumor cells would enhance uptake of DNA-binding drugs and result in an increased therapeutic effect. In alternative embodiments, other diseases, such as malaria, can be treated in a similar fashion, based on the development of cell-surface DNA binding in red blood cells parasitized with the malarial parasite *Plasmodium falciparum*.

The Examples which follow are illustrative of specific embodiments of the invention, and various uses thereof. They set forth for explanatory purposes only, and are not to be taken as limiting the invention.

EXAMPLE 1

Isolation of a Human Membrane-Associated DNA Receptor (DNA-R)

As described in the specification above, DNA binding to cells had been observed in the art, and the behavior of said binding suggested the existence of a DNA binding protein expressed at the cell surface. In order to isolate a novel DNA-binding protein from human cells, serum from a patient with systemic lupus erythematosus (SLE), treated to deplete the sera of anti-DNA antibodies by multiple (6×) passages over a DNA sepharose column, was used to screen a λgt11 cDNA expression library made from liposaccharide stimulated human monocytes. This serum has been shown to have anti-DNA receptor activities (defined by the blocking of DNA binding to cells; Bennet et al., 1992. *J. Clin. Invest.* 76: 2182–2190).

From approximately one million plaques screened with this sera, ten positive phage clones were identified and isolated according to the technique of Young and Davis (1983, *Proc. Natl. Acad. Sci. USA* 80: 1194–1198). The clones were grouped into two classes, based on Southern blot and Western blot analyses using eluted antibodies. Sequence analysis of the 1.4 kilobase (kb) insert of one clone (clone 88), which was highly reactive on Western blots with SLE serum, revealed an open reading frame that was open at the 5' end of the clone and contained a translation stop codon at the 3' end. This open reading frame coded for a 46.7 kiloDalton (kDa) protein fragment.

The full length cDNA for the putative DNA-R was obtained in segments from peripheral blood mononuclear cells, human Burkitt lymphoma cells (Raji; Accession No. CCL 86, American Type Culture Collection, Manassas, Va.), human cervical carcinoma cells (HeLa; ATCC Accession No. CCL 2), and human lymphoblastic leukemia cells (MOLT-4; ATCC Accession No. CRL 1582). A 731 base pair (bp) DNA probe from clone 88 was used to screen a λgt11 phage library from a Raji cell line (the library was obtained from Clonetech Labs, Palo Alto, Calif.). A 2409 bp clone which contained an additional 462 bp of 5' open reading frame (ORF) sequence was obtained from this screening. Additional sequence from the 5' extent of the cDNA was isolated using two variations of the 5' RACE (rapid amplification of cDNA ends) method. In the first 5' RACE method, single stranded DNA (ssDNA) was synthesized from HeLa cell mRNA using polyT primers and reverse transcriptase. A polyA tail was added to the 5' end of the ssDNA by terminal transferase. The single stranded cDNA was amplified using a gene specific primer and a polyT primer. This clone contained 753 bp of additional sequence 5' of the previously obtained sequence. The remainder of the 5' sequence of the cDNA was obtained from MOLT-4 cDNA by Marathon Race cDNA amplification (Clonetech Labs, Palo Alto, Calif.) according to the manufacturer's instructions. This procedure produced an additional 1290 bp clone consisting of 340 bp of ORF and a 950 bp 5' untranslated region. Combining the results from these screening and amplification experiments produced the predicted full length cDNA encoding the DNA-R of the invention.

A complete, full-length cDNA for the putative DNA receptor was cloned as a single RT-PCR product from MOLT-4 mRNA using oligonucleotide primers having the following sequence:

```
                                             (SEQ ID NO: 5)
Primer 5': ACCCGAGCATGGATCCGCCACCATGGCTGTGCAGGCAGC
and
                                             (SEQ ID NO: 6)
Primer 3': GGTATCTAGATCCATGGTGTGGTCAC
```

The complete sequence was 4351 nucleotides (SEQ ID NO: 1) in length with a defined open reading frame of 3576 nucleotides encoding a protein of 1192 amino acids (SEQ ID NO: 2). The isolation protocol is schematically illustrated in FIG. 1.

EXAMPLE 2

DNA Receptor Gene Expression and Protein Sequence Analysis

Figure 2:
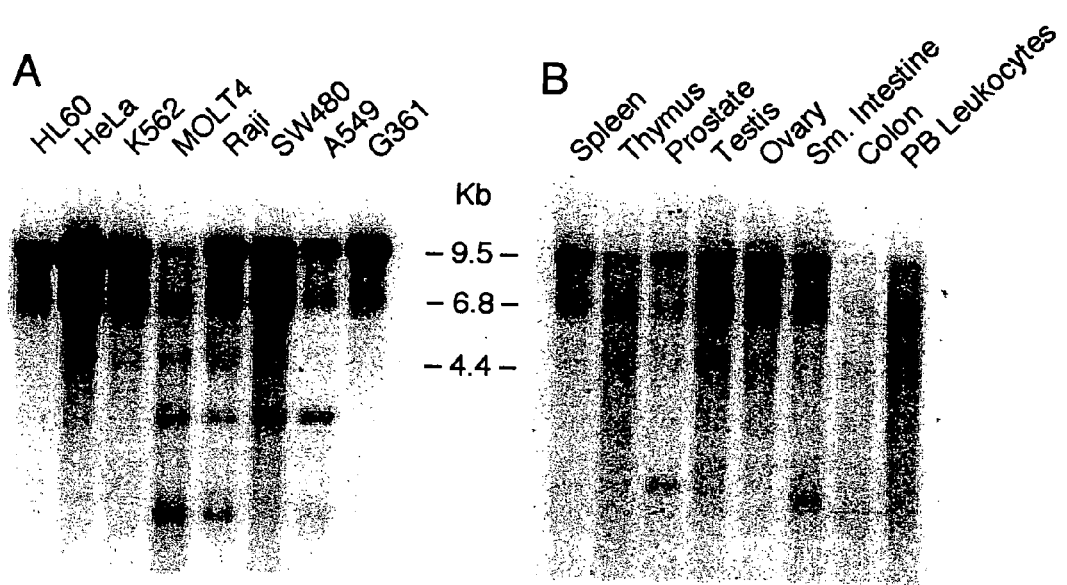
FIGS. 2A and 2B show Northern analysis of human cancer cell lines (FIG. 2A) and human tissues (FIG. 2B). A 442 bp DNA fragment (probe 11) from the 3' end of the gene coding for DNA-R was used as the radiolabeled probe for each blot.

Tissue-specific and cell line-specific expression patterns of its corresponding mRNA in various human tissues was analyzed by Northern blot analysis on RNA isolated from various tissues and cancer cell lines. The results of these experiments are shown in FIG. 2.

A panel of tissue samples was examined by Northern hybridization analysis performed under low stringency conditions, defined as hybridization at 42° C. in 5× SSPE (0.75M NaCl, 0.05 mM NaH$_2$PO$_4$, 5 mM EDTA), 10× Denhardt's solution (0.2% Ficoll, 0.2% polyvinylpyrrolidone, 0.2% bovine serum albumen), 100 µg/mL salmon sperm DNA, 2% SDS and 50% deionized formamide and 1–2×10$^6$ cpm random-primed, $^{32}$P labeled probe, followed by washing in 0.1×SSC (15 mM NaCl, 1.5 mM trisodium citrate, 0.1% SDS). The blots were hybridized with aprobe consisting of 442 bp of sequence from the 3' end of the coding sequence from the DNA-R gene to determine the distribution of receptor mRNA. This analysis revealed two major transcripts of 9.5 and 6.8 kb in all human tissues and cancer cell lines examined. Transcript expression was relatively abundant in spleen, testis, ovary, and small intestine. Several smaller transcript sizes were also observed in some of the tissues and cell lines examined (FIG. 2).

A homology search against human genomic sequence placed the DNA receptor on chromosome 9q34 (GenBank Accession number AC007066, marker HIM9.89 on Contig CHR9.SL27). The genomic sequence, which covered 85% of the cDNA starting from the 5' end, revealed the location of 16 complete exons and the beginning of a 17$^{th}$ exon. A BLAST search of the expressed tag sequence (EST) database indicated wide expression of this gene in normal human tissue (liver/spleen, prostate epithelial, germinal B cell, white adipose, pregnant uterus, fetal heart/liver and spleen) and in tumor and transformed human cells (Jurkat, HL60, 293, G361, B-cell lymphocytic leukemia, colon tumor, melanoma, and parathyroid tumor).

Figure 3:
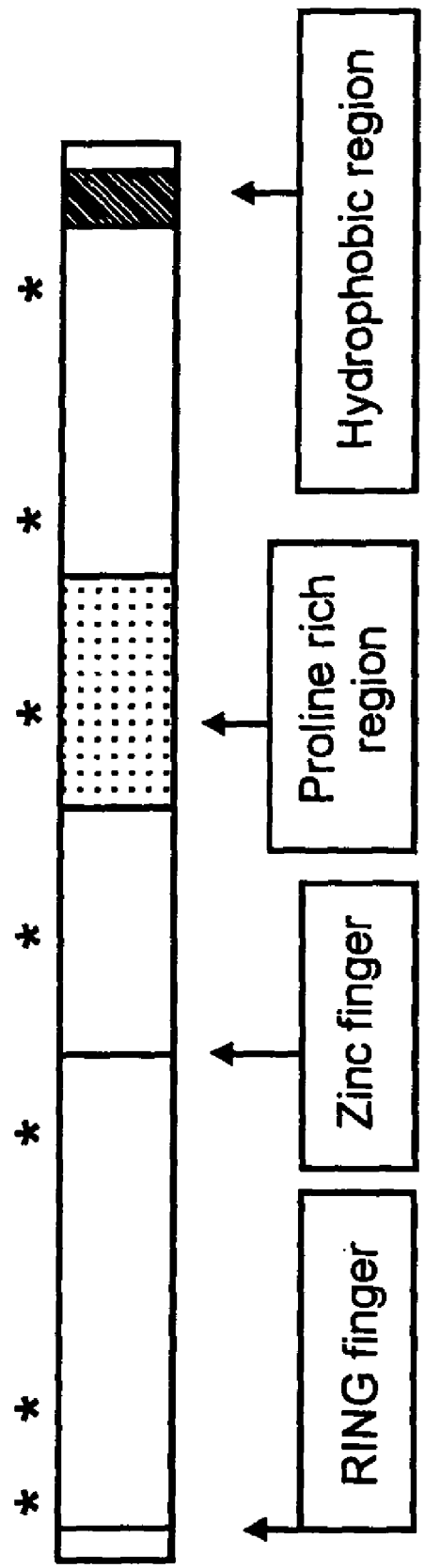
FIG. 3 is a schematic diagram of the human DNA-R of the receptor showing the location of the RING finger, zinc finger, proline rich and hydrophobic regions. An * denotes the N-linked glycosylation sites at amino acid positions 122, 394, 430, 451, 466, 468 and 1150.

FIG. 3 provides a schematic diagram of the structure of the DNA-R protein encoded by SEQ ID No. 1. Hydropathy analysis identified a 38 amino acid hydrophobic region near the carboxy terminus of the protein (amino acids 1133–1171) which is a potential transmembrane domain. Expression of a soluble species of this receptor by deleting these amino acids supported identification of this region as a transmembrane domain. In addition, seven consensus sites for linked glycolsylation have been identified (amino acid positions 122, 394, 430, 451, 466, 468, and 1150) and there is a proline rich (20% of the residues are proline) region spanning amino acids 549–809 (FIG. 3). The calculated isoelectric point of the DNA receptor protein is 6.4. The BLAST search also identified two art-recognized amino acid sequence motifs in the DNA-R sequence: a C3HC3D Ring finger subtype located near the amino terminus (amino acids 14–50) and a C3H zinc finger located near the center of the protein sequence (amino acids 416–435). An alignment of several ring finger motifs is shown in FIG. 4A; DNA-R differs from the originally identified C3HC4 Ring finger motif by the replacement of the last cysteine with an aspartic acid. The alignment of the conserved cysteines and histidines of the C3H zinc finger motif is shown in FIG. 4B.

EXAMPLE 3

DNA Receptor Expression and Protein Expression Analyses

The DNA-R of the invention was produced recombinantly as follows. A BamHI-HpaI cDNA fragment containing the coding sequence for amino acids 1–1190 (i.e., missing the two most carboxylterminal amino acids) of the DNA-R of the invention was cloned into pTriplFlu (obtained from J. Epstein, University of Pennsylvania, Philadelphia, Pa.). This vector contains a sequence encoding an epitope tag from the influenza hemagglutinin gene in triplicate inserted immediately 3' of the multiple cloning site of the parent vector, pcDNA3, and which are in-frame with the inserted DNA-R cDNA sequence. This vector was introduced into human 293 cells by transfection using Lipofectamine (Life Technologies, Gaithersburg, Md.) according to the manufacturer's instructions. Transfected cells (293-DNA-R/flu) were selected by culturing in growth media (DMEM supplemented with 10% fetal calf serum, 2 mM L-glutamine, 100 U/mL penicillin and 100 g/mL streptomycin) supplemented with 500 µg/mL G418.

In order to characterize DNA-R protein expression in mammalian cells, immunoprecipitation and Western blotting experiments were performed with protein extracts isolated from several cell lines using polyclonal antisera raised against an amino-terminal fragment of the DNA-R of the invention, comprising amino acid residues 1–575.

Polyclonal antibodies were produced to a purified fragment of the DNA-R (comprising amino acids 1–575) using conventional techniques. Three female New Zealand White rabbits (Western Oregon Rabbit Company), weighing 2.3–3.0 kg, were injected subcutaneously with 50 µg of the DNA-R peptide that was produced in bacteria as a GST fusion protein (described in Example 4) and purified from its fusion partner. The antigen was emulsified with Titre-Max (CytRx Corp., Norcross, Ga.) in a final volume of 0.5 mL. The rabbits were boosted 4 weeks later with 15 µg of antigen/Titre-Max mixture, again 2 weeks later, and were maintained on a once-a-month booster schedule thereafter. The rabbits were bled 7–10 days after each boost with antigen and the sera analyzed for reactivity to the immunizing antigen.

Figure 5:
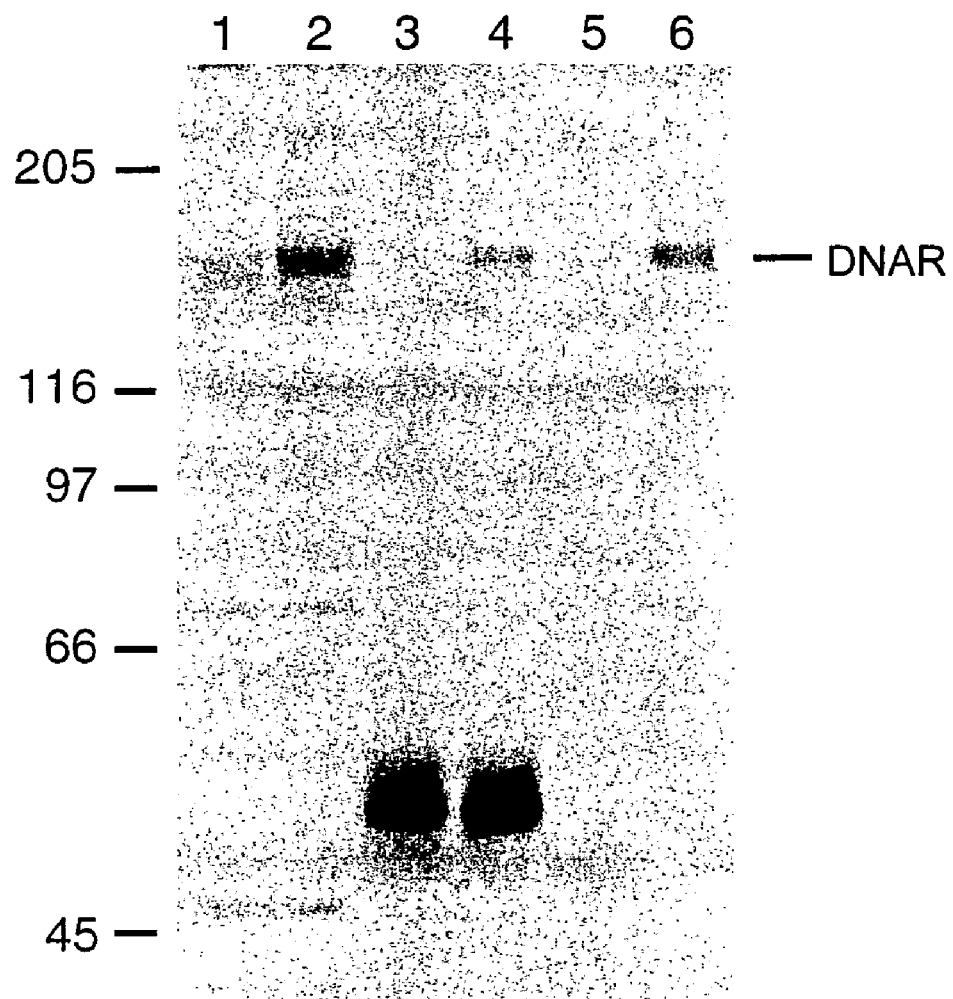
FIG. 5 is an analysis of DNA-R protein expression in mammalian cells. DNA-R was immunoprecipitated both as the native molecule and in an HA-tagged embodiment from stably-transfected human 293 cells (DNA-R/flu cells). Lane 1, lysate of 293 cells; lane 2, lysate of 293-DNA-R/flu cells; lanes 3–6, immunoprecipitation of 293-DNA-R/flu cell lysates with: rabbit preimmune serum (lane 3) or anti-DNA-R (lane 4), control mouse monoclonal antibody (lane 5) or anti-HA (lane 6). Detected by Western blotting with rabbit anti-DNA-R IgH, immunoprecipitating rabbit IgG heavy chain.

The polyclonal antisera obtained from the inoculated rabbits was used in Western blot analyses. A protein of Mr~$1.5 \times 10^5$ was identified by the anti-DNA-R antibody in most cells tested (including 293, COS7, G361, HeLa, HRE605, MOLT-4, Raji, A549, B16). A protein with a similar mobility was detected in lysates of genetically-engineered human 293 cells (293-DNA-R/flu) that were stably transfected with an expression vector for a carboxy-terminal HA-tagged DNA-R (pDNA-R/flu). As shown in FIG. 5, this protein was detected by immunoprecipitation and/or Western blot analysis with either the rabbit polyclonal anti-DNA-R (1–575) antisera described above or with a mouse monoclonal antibody (anti-HA) specific for the carboxyl-terminal HA tag in the recombinantly-produced protein.

Figure 6:
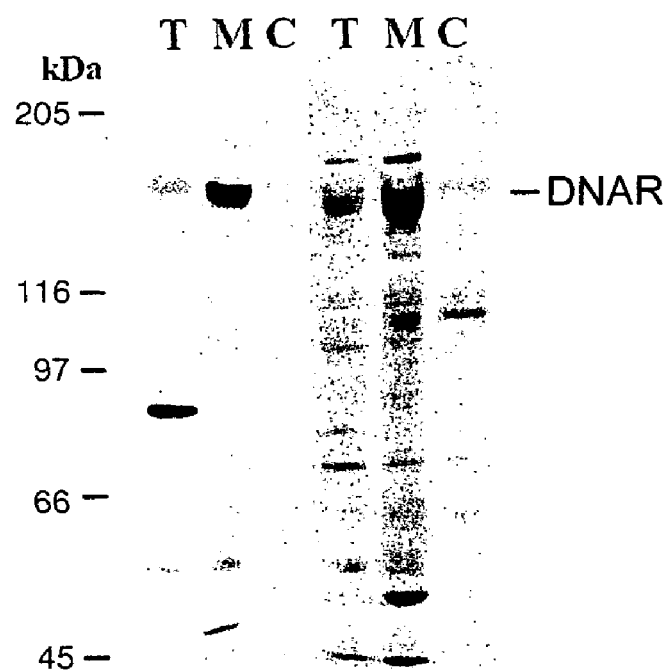
FIG. 6 shows the intracellular location of the DNA-R protein, associated with cell membranes in 293-MNAB/flu cells as detected by Western blotting with anti-HA (left half) or anti-DNA-R (right half). T, Triton X-100 whole-cell lysate; M, crude membrane fraction; C, cytosolic fraction.
Figure 7:
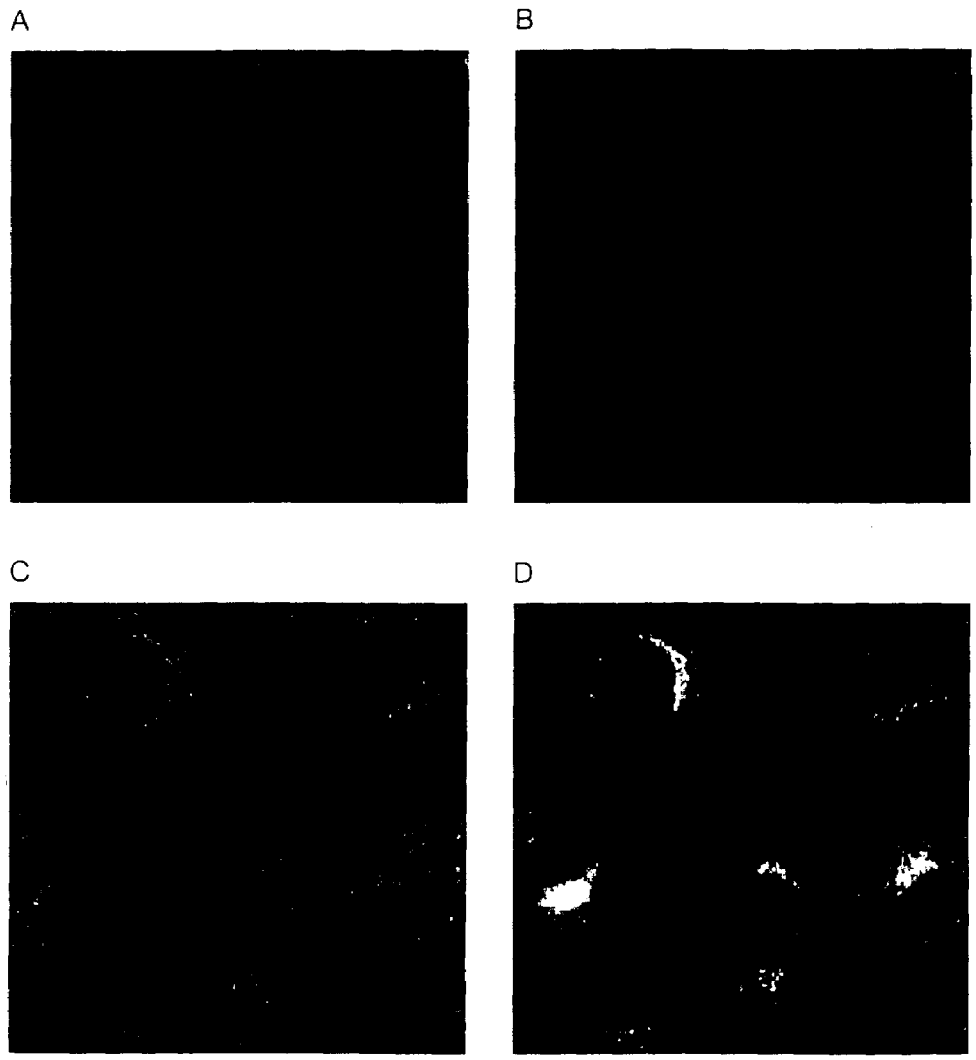
FIG. 7 illustrates immunofluorescence staining using anti-DNA-R and anti-transferrin antibodies on fixed, permeablized A549 cells. A, Double stained with rabbit and sheep nonimmune sera. B, anti-DNA-R. C, anti-transferrin receptor. D, double stained for anti-DNA-R (red) and anti-transferrin receptor (green); colocalized staining appears yellow.

In order to determine cellular localization of the DNA-R protein, crude membrane fractions from recombinant 293-DNA-R/flu cells were examined by Western blot analysis with either anti-DNA-R or anti-HA antibodies. The results shown in FIG. 6 indicated that essentially all the DNA-R protein in those cells was associated with the membrane fraction. Indirect immunofluorescence on fixed, permeabilized cells showed anti-DNA-R staining was predominantly localized to the perinuclear region of the cell, although no nuclear staining was observed (FIG. 7). Double staining with anti-DNA-R and anti-transferrin receptor antibodies showed partial colocalization of the DNA-R and transferrin receptor, however the DNA-R did not colocalize with the transferrin receptor in peripheral endosomes (FIG. 7). These results indicate that extracellular DNA is taken up by cells expressing the DNA-R of the invention by endocytosis, and suggest that compounds that influence intracellular trafficking of molecules taken by endocytosis are useful for modulating the intracellular fate (such as degradation in lysosomes or transport to the cell nucleus) of extracellular DNA.

Figure 8A:
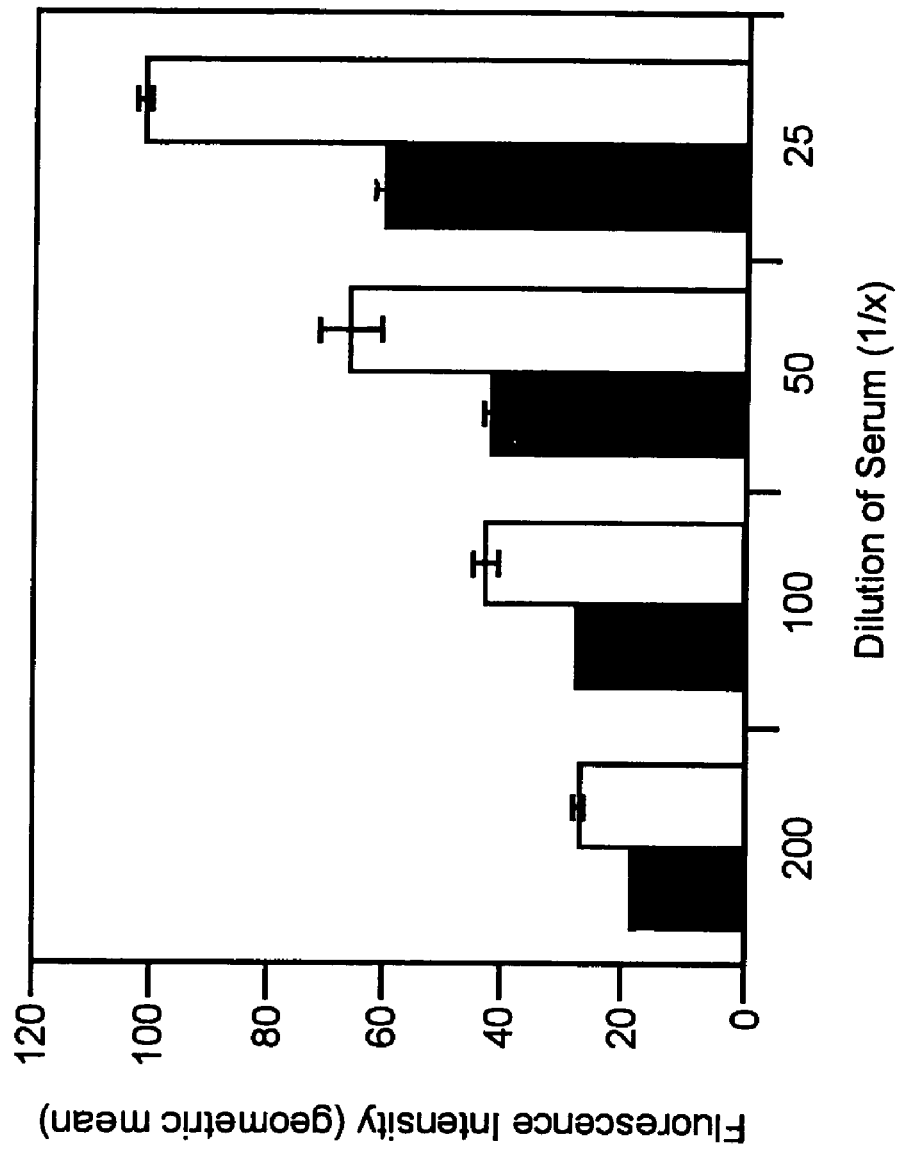
FIG. 8A shows the results of antibody staining of 293 cell surface using polyclonal rabbit antisera raised against an amino-terminal fragment (aas 1–575) of the DNA-R of the invention. 293 cells were incubated with preimmune serum (black bars) or immune serum (white bars). Antibody binding was detected with FITC conjugated goat anti-rabbit IgG by flow cytometry. Each bar represents the geometric mean fluorescence intensity±sd (n=3, 10,000 viable cells in each analysis). The geometric mean fluorescence of the secondary antibody alone was 7.6±0.08 (n=3).
Figure 8B:
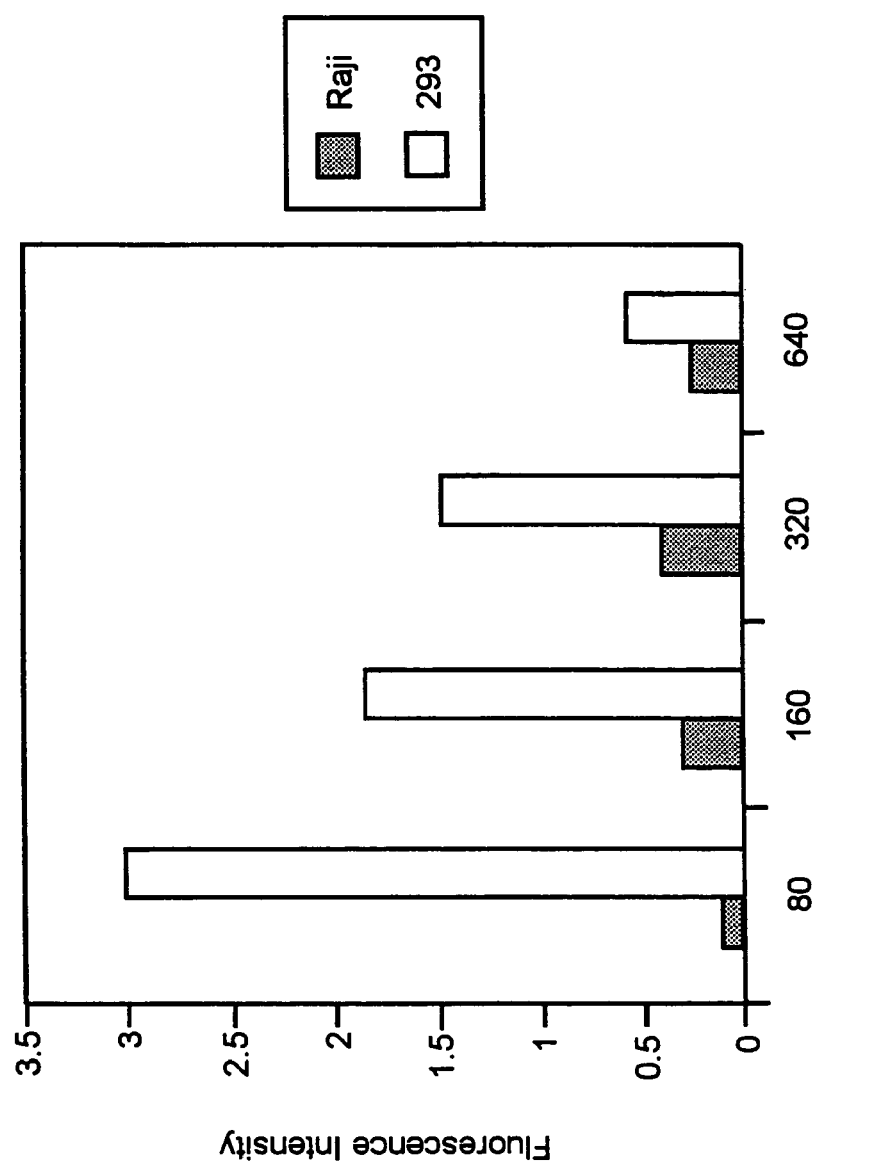
FIG. 8B shows antibody binding to the cell surface of Raji and 293 cells using antibodies raised against an amino-terminal fragment (1–575). Cells (Raji, gray bars; 293, white bars) were incubated with serial dilutions of rabbit antisera (#41 bleed 2) produced against the amino terminal portion (amino acids 1–575) of the DNA receptor. The cells were then incubated with FITC-goat anti-rabbit IgG and the fluorescence intensity measure by FACS. Fluorescence due to preimmune sera has been subtracted.

To determine if DNA-R is located on the cell surface, cells were incubated with anti-DNA-R (1–575) immune rabbit serum. Antibody binding was detected by flow cytometry with FITC labeled secondary antibodies to rabbit IgG. At all serum dilutions the fluorescence intensity of the cells incubated with immune serum was significantly higher than that of cells incubated with preimmune serum ($p<0.003$) suggesting that DNA-R is expressed on the cell surface (FIG. 8).

These results demonstrated that the DNA-R protein, either natively expressed or expressed from the cloned cDNA of the invention, or genetically-engineered embodiments thereof, localized to cell membranes as predicted by the hydropathy plot of the carboxyl terminus.

EXAMPLE 4

Soluble DNA-R Fusion Protein Binds DNA with High Affinity

Figure 9A:
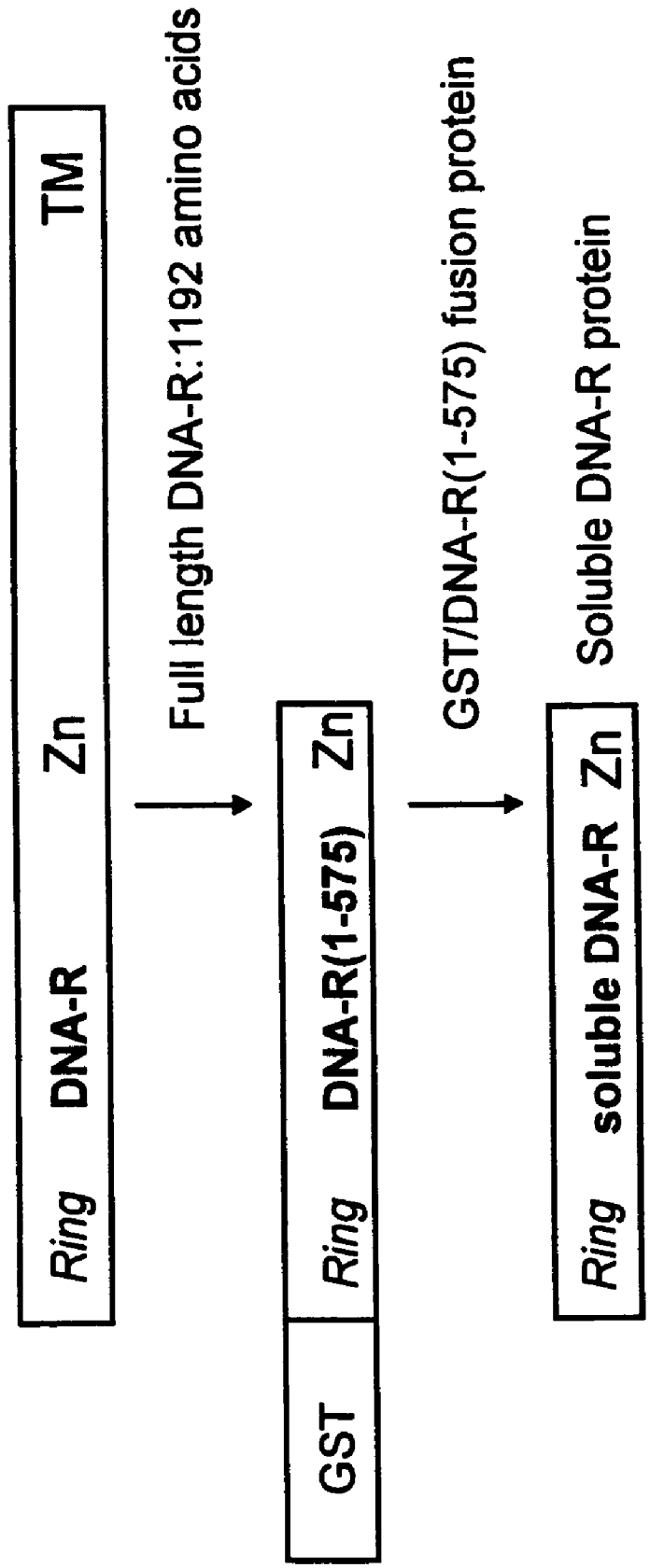
FIG. 9A is a schematic diagram of the preparation of the soluble DNA-R protein from the full length DNA-R.
Figure 9B:
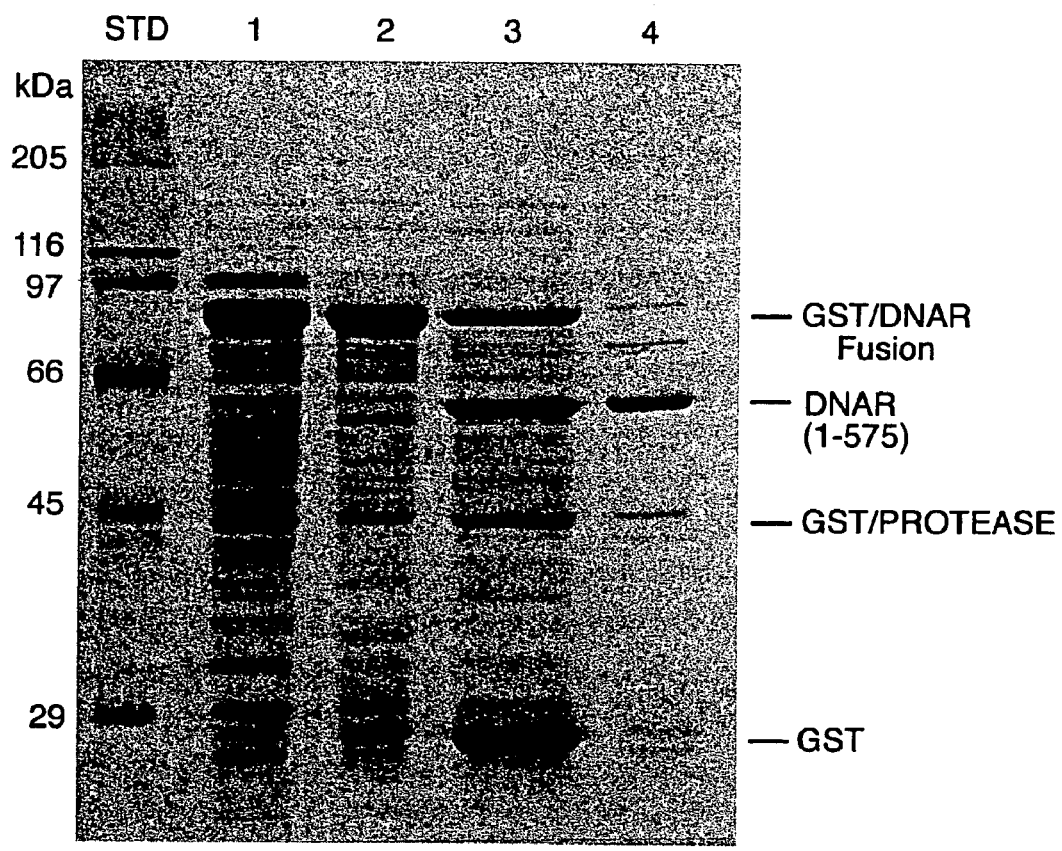
FIG. 9B is an SDS-PAGE analysis of expression, affinity purification, and proteolysis of a fusion protein (termed GST/DNA-R) created between glutathione-S-transferase (GST) and an amino-terminal fragment (1–575) of the DNA-R of the invention. Lane 1, whole cell extract of E. coli expressing GST/DNA-R; lane 2, GST/DNA-R bound to glutathione (GSH)-sepharose; lane 3, site-specific proteolysis of GST/DNA-R while bound to GSH-sepharose; lane 4, eluate from GSH-sepharose following on-gel proteolysis of GST/DNA-R containing highly purified DNA-R (1–575) peptide.

The capacity of the DNA-R of the invention to bind DNA, and particularly the capacity of a soluble form of the DNA-R protein to bind DNA (which would be useful for the development of a therapeutic agent as described more particularly below) was determined. For these experiments, a fusion protein between the amino terminal portion of the DNA receptor (amino acids 1–575), lacking the transmembrane region but containing both the RING and zinc finger domains, was produced using the pGEX vector system (Pharmacia, Kalamazoo, Mich.) for expression of glutathione-S-transferase (GST)-fusion proteins in *E. coli* and named GST/DNA-R (1–575). A schematic diagram of the production of this protein fragment and its structure relative to the full-length DNA-R of the invention is shown in FIG. 9A. Polyacrylamide gel analysis of the production, proteolysis, and purification of the recombinant DNA-R peptide is shown in FIG. 9B. The calculated molecular weights of the GST/DNA-R fusion protein and the DNA-R peptide are 90 kDa and 63 kDa respectively.

Figure 10:
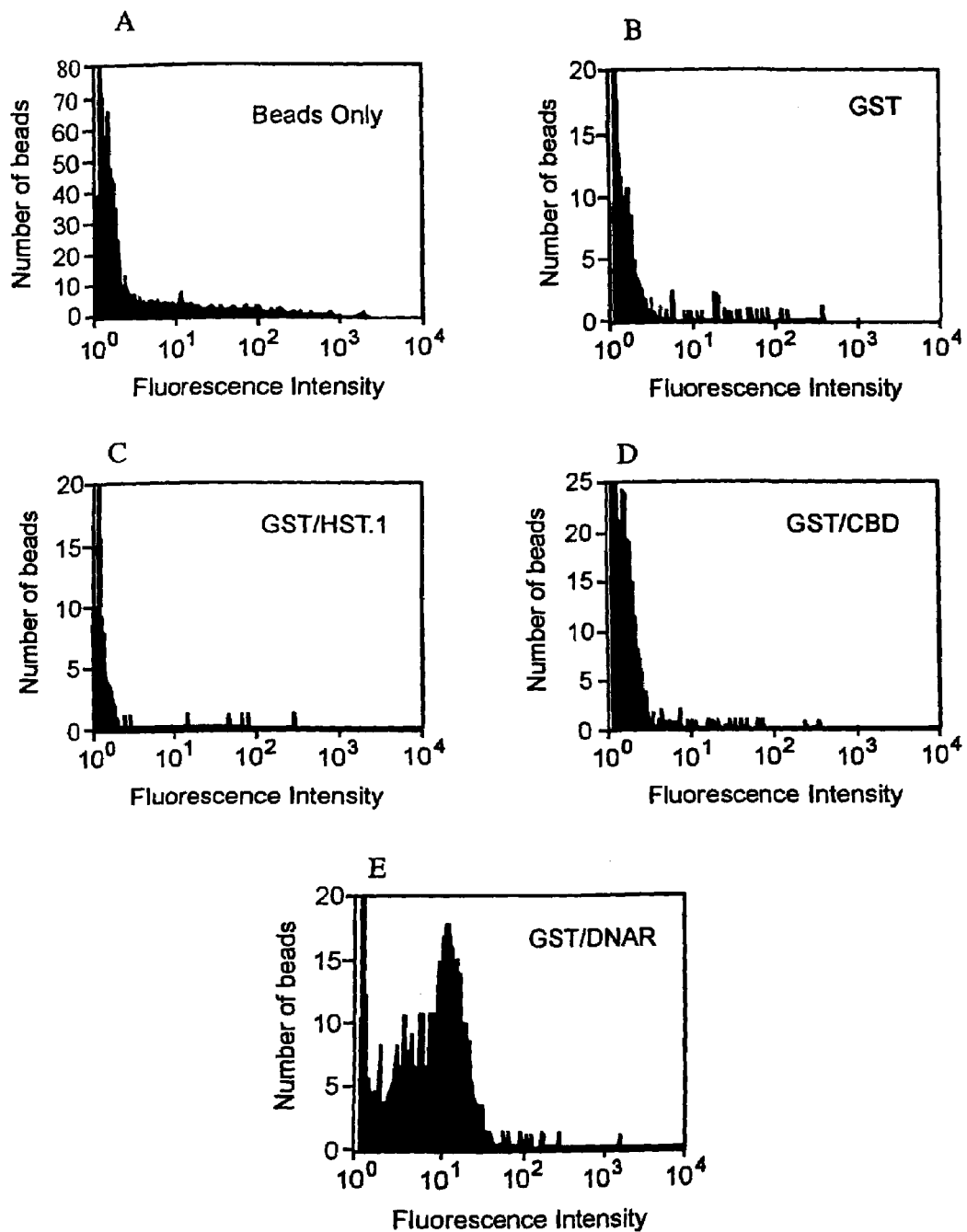
FIGS. 10A through 10E show that GST/DNA-R but not control proteins immobilized on glutathione sepharose bind a fluorescently-labeled plasmid DNA (YOYO/pGEM4Z). Shown in the figure is glutathione sepharose without immobilized protein (FIG. 10A), or with immobilized GST (FIG. 10B), GST/HST.1 (FIG. 10C), GST/CBD (FIG. 10D), or GST/DNAR (FIG. 10E) incubated with YOYO/pGEM4Z for 30 min at 4° C. After washing, the fluorescence intensity was measured by FACS.

The purified GST/DNA-R fusion protein was then examined for its ability to bind plasmid DNA. Three independent in vitro assays were used to assess DNA binding by the fusion protein. First, the ability of GST/DNA-R, bound to glutathione sepharose beads, to bind YOYO-labeled plasmid DNA was determined by incubation with 0.9 μg YOYO/ DNA in 0.5 mL of medium. (YOYO-1 is an intercalating fluorochrome that is flourescent only when bound to DNA, obtained from Molecular Probes, Eugene, Oreg.) Beads ($3.5 \times 10^5$) and YOYO/DNA were incubated for 30 minutes at 4° C., washed once and then fluorescence intensity analyzed by FACS. As seen in FIG. 10, the GST/DNA-R fusion protein was extremely efficient in binding DNA whereas purified GST protein alone and two additional, unrelated GST-fusion proteins (GST-CBD and GST-HST. 1, gifts from Dr. Roland Kwok, Vollum Institute, Portland Oreg.) failed to show any DNA binding capability. Following FACS analysis an aliquot of glutathione sepharose-bound protein from each sample used in the DNA binding assay was analyzed by SDS-PAGE followed by Coomassieblue staining. An approximately equivalent amount of each GST-fusion protein was shown to be present in each sample.

Figure 11:
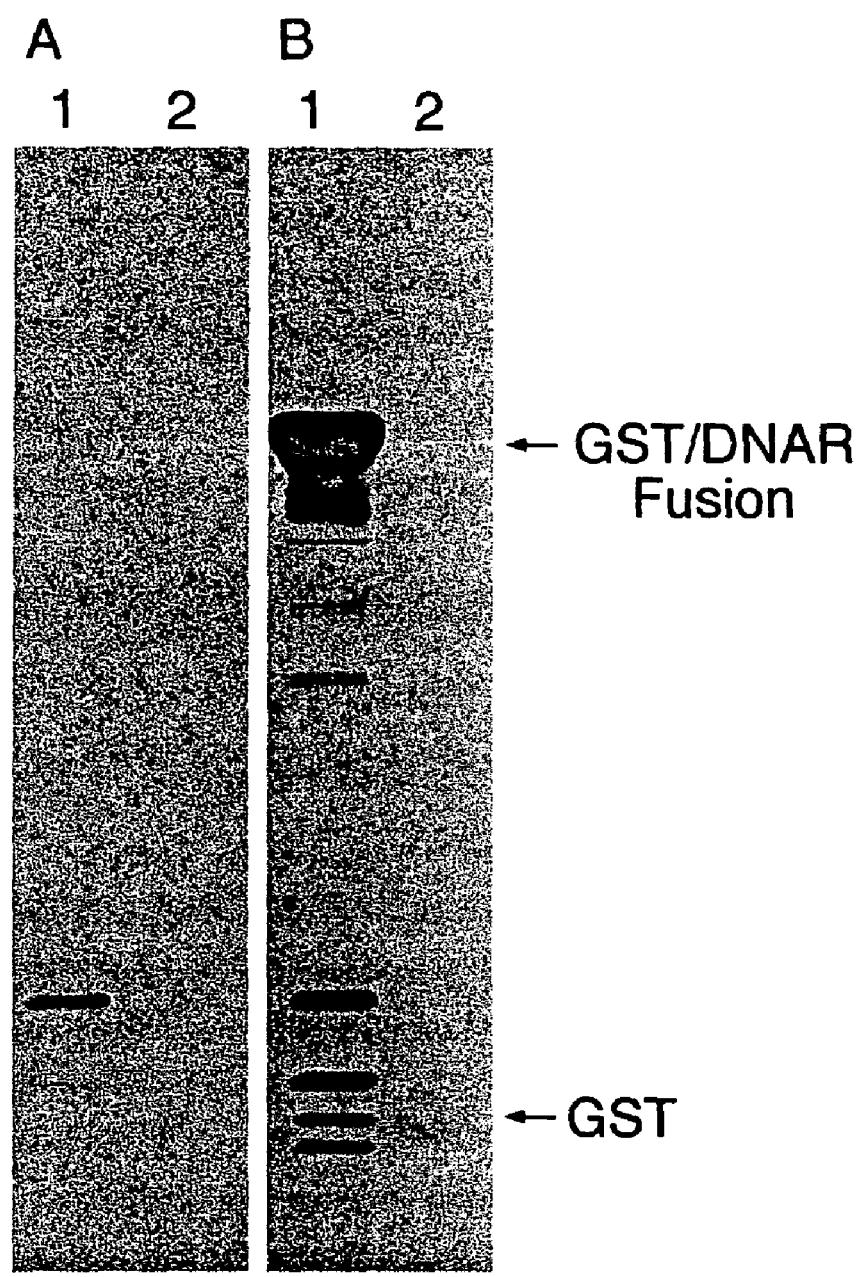
FIGS. 11A and 11B is the result of a "Southwestern" blot of nucleic acid binding to DNA-R. The experiments were performed by SDS-PAGE analysis, transfer to nitrocellulose and then incubated with (FIG. 11A) or without (FIG. 11B) biotinylated DNA, followed by binding to streptavidin conjugated with horse radish peroxidase (HRP) and reaction with colorimetric substrate. Absorbance was measured at 450 nm. These results showed that GST/DNA-R but not GST bound biotinylated DNA.

To further assess whether the GST/DNA-R fusion protein was a DNA-binding molecule, a Southwestern blot was performed. The purified GST/DNA-R fusion protein and GST protein alone were electrophoresed on a polyacrylamide gel, electrophoretically transferred to nitrocellulose and then probed with biotinylated DNA. DNA binding was visualized by addition of steptavidin conjugated with horse radish peroxidase (HRP) using conventional methods. As seen in FIG. 11, purified GST/DNA-R fusion protein (FIG. 11B, lane 1), but not GST protein alone (FIG. 11B, lane 2) bound biotinylated plasmid DNA. Other peptides seen to react with biotinylated DNA/streptavidin-HRP in the GST/ DNA-R samples (FIG. 11B, lanes 1) probably represent partially degraded GST/DNA-R peptides and/or traces of contaminating bacterial proteins. Lanes in FIG. 11A represent no added DNA.

Figure 12:
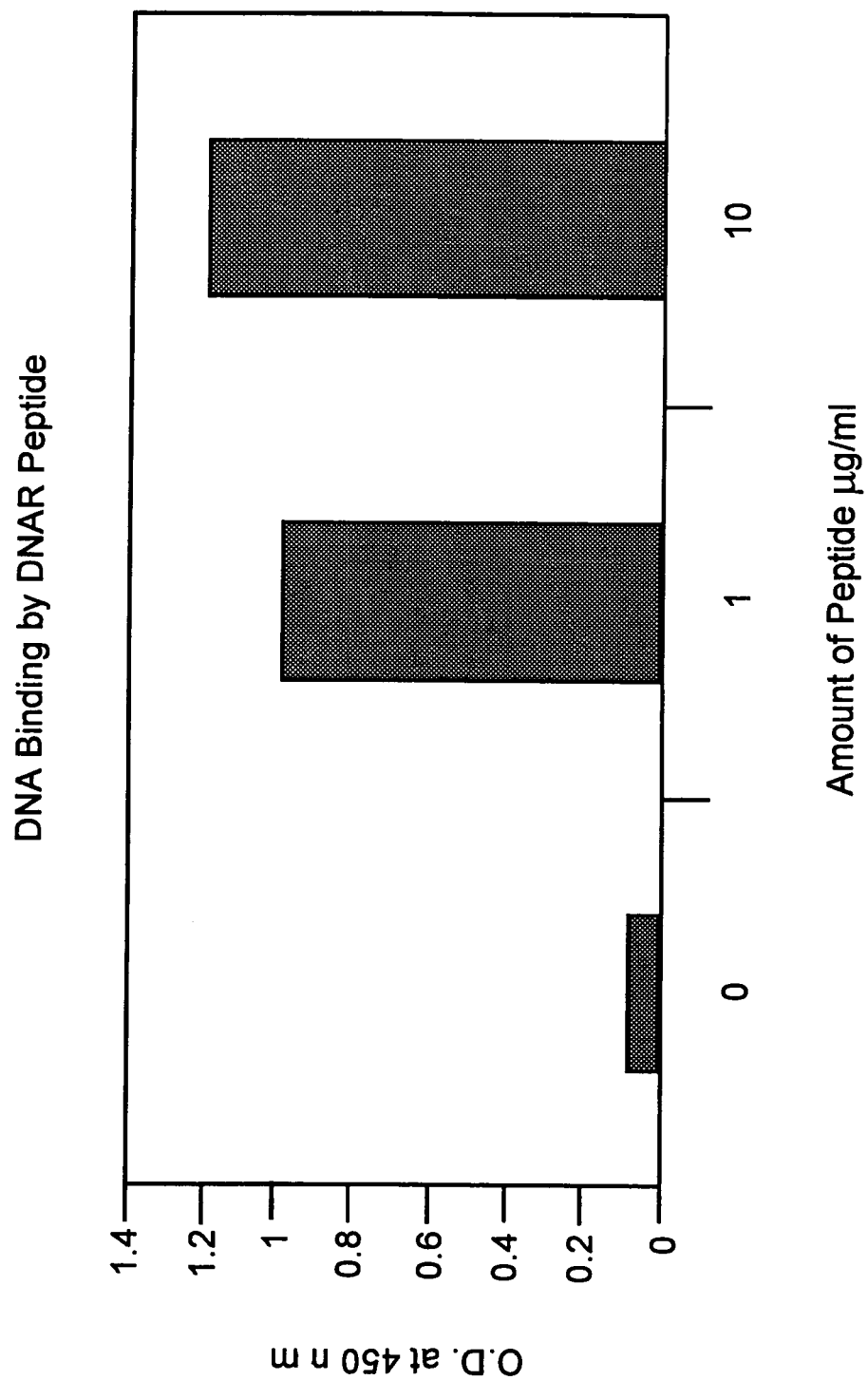
FIG. 12 shows the results of an enzyme linked immunosorbent assay (ELISA) in which purified DNA-R fragment (1–575) bound to immobilized DNA. DNA-R fragment (at concentrations of 0, 1, and 10 µ/mL) was incubated with immobilized plasmid DNA in ELISA plates. The plates were then incubated with anti-DNA antibodies at a 1:100 dilution, followed by secondary antibody conjugated to HRP and reaction with colorimetric substrate. Absorbance was measured at 450 nm.

Third, as a final assessment of the DNA binding ability of the purified DNA receptor fragment (amino acids 1–575) the ability of the purified peptide to bind to ELISA plates coated with plasmid DNA (VARELISA dsDNA kit, Pharmacia) was determined. Binding of the DNA receptor peptide was detected using the rabbit anti-DNA-R polyclonal antisera described Example 3. As shown in FIG. 12, purified DNA-R peptide bound to DNA coated plates when tested at both 1 μg/mL and 10 μg/mL. Negative controls not including the DNA-R fragment showed no reactivity.

These results demonstrate that the DNA receptor gene of the invention encodes a protein that specifically binds DNA, and that the DNA binding portion of the molecule resided in the protein fragment having amino acid sequence 1–575 of the native protein.

Figure 14:
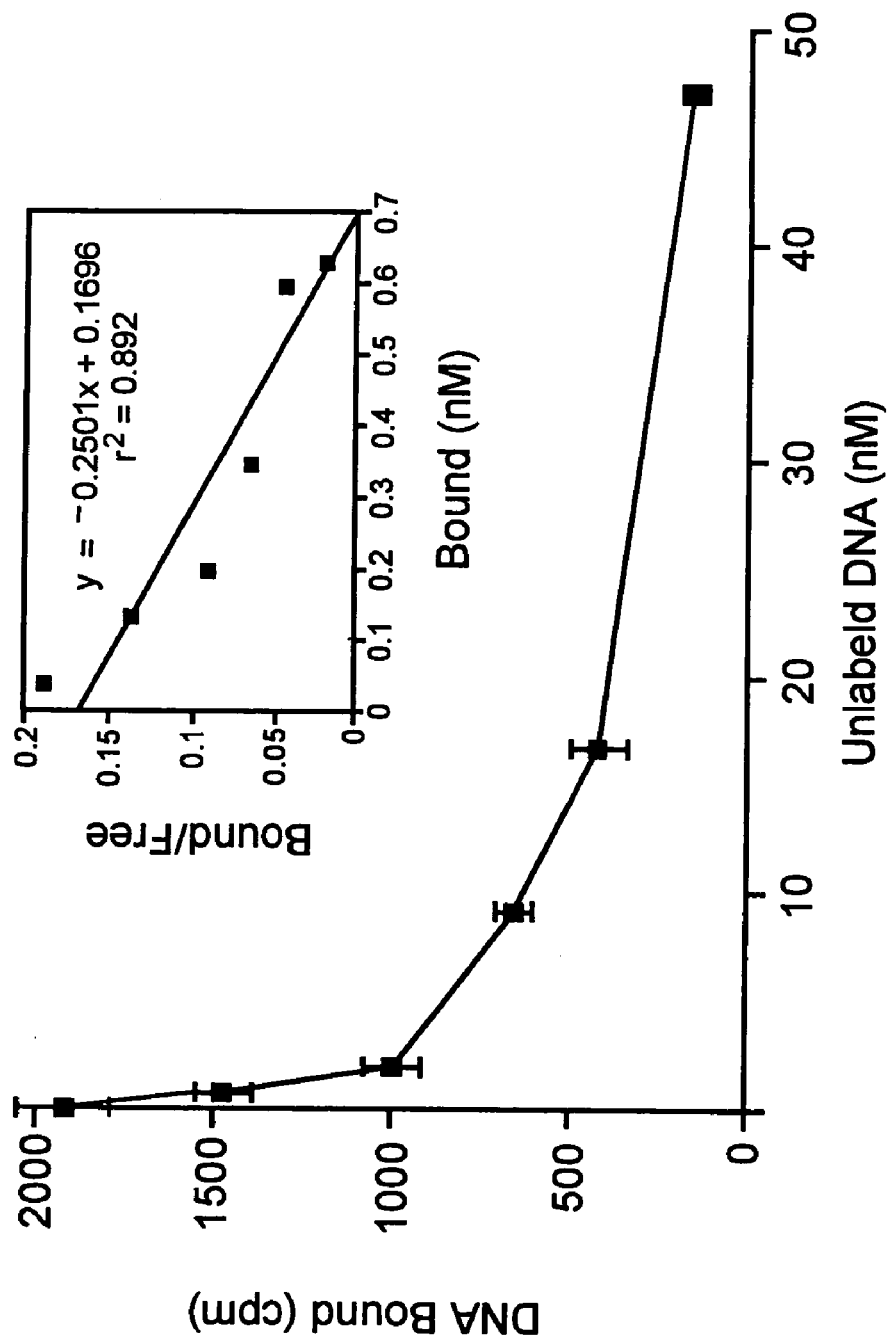
FIG. 14 illustrates results of experiments demonstrating that a soluble form of the DNA-R of the invention binds DNA with high affinity using a nitrocellulose filter binding assay. Soluble DNA-R (sDNA-R) at a concentration of 2 nM and labeled DNA (200 pM, 1×10$^6$ cpm/pmol) held constant and increasing concentrations of unlabeled DNA. Data are the mean±s.d. of triplicate binding determinations. Inset: Scatchard transformation of the binding data.

Having demonstrated that the protein encoded by the cloned cDNA of the invention bound DNA, the affinity of soluble GST-DNA-R for DNA was estimated using a nitrocellulose filter-binding assay. The assay was performed using cold DNA competition where known amounts of GST/DNA-R (2 nM) and labeled DNA (200 pM) were titrated with increasing amounts of unlabeled calf thymus DNA. These results demonstrated that DNA binding to the DNA-R of the invention was saturable, consistent with its identification as a specific receptor. A Scatchard transformation of the data yield a $K_D$~4 nM (FIG. 14).

Figure 13:
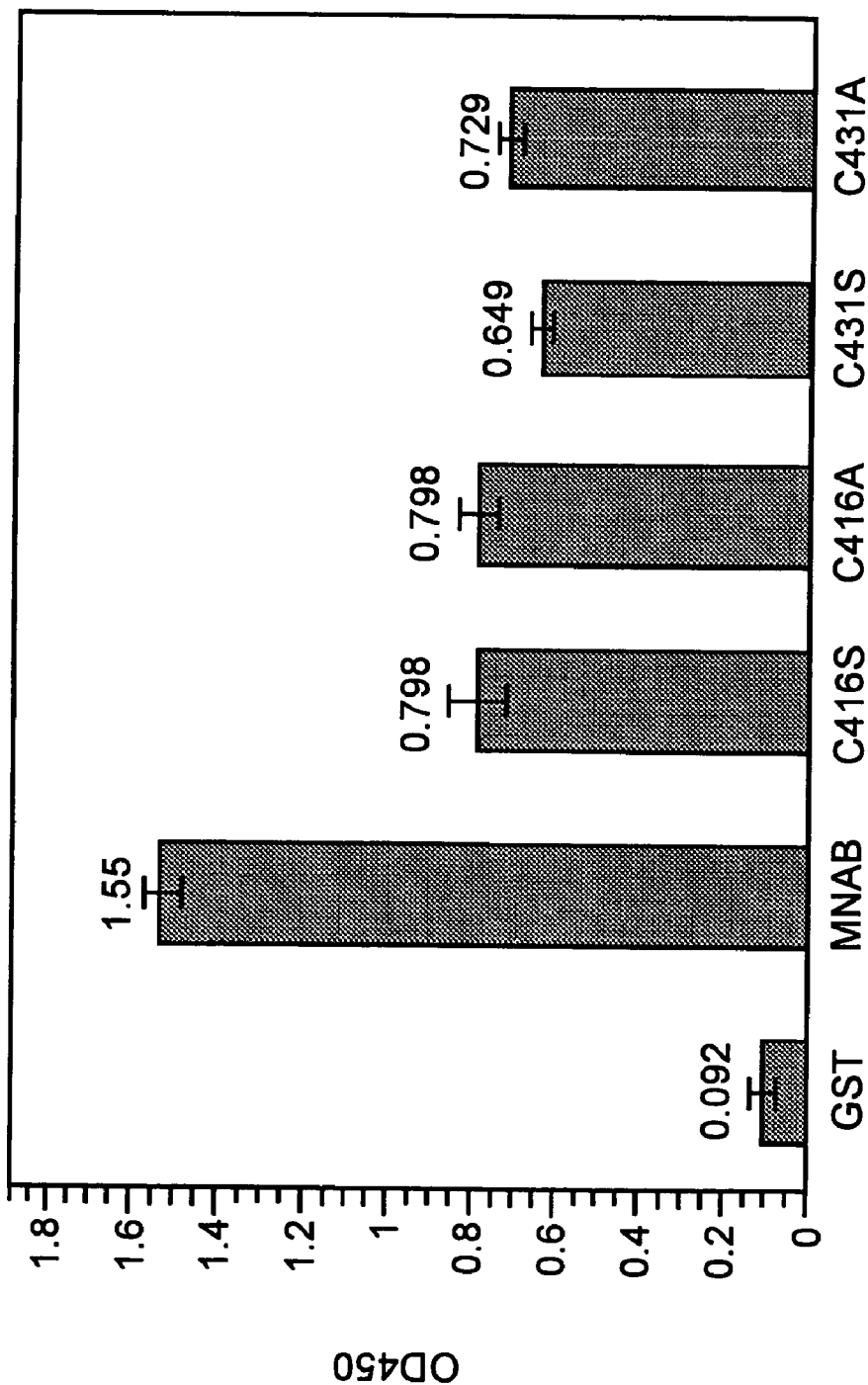
FIG. 13 shows that a DNA-R fragment comprising a zinc finger domain (at amino acids 416–435) participates in DNA binding by GST/DNA-R(1–575). Cysteine residues (at positions 416 and 431) were independently altered to serine (and termed C416S and C431S, respectively) or alanine (and termed C416A and C431A, respectively) and ELISA performed to evaluate DNA binding. The zinc finger cysteines at either 416 or 431 were altered to either a serine (C416S, C431S) or an alanine (C416A, C431A). Binding (100 ng/well) of wild-type (GST/DNA-R) or mutant GST-fusion proteins or GST alone to immobilized DNA was detected using anti-GST by ELISA. Data are the mean±s.d. of triplicate determinations.

To demonstrate that the binding of DNA by the soluble form of the DNA-R (amino acids 1–575) was not due to monospecific charge-related interactions, the role in DNA binding of the zinc finger domain at amino acids 416–435 was examined. Using site-directed mutagenesis, the codon for the conserved zinc finger cysteines at either amino acids 416 or 431 were altered to a codon for either alanine or serine. The mutagenized GST/DNA-R fusion proteins were expressed in *E. coli* and affinity purified on glutathione sepharose, then tested for their ability to bind to immobilized DNA by ELISA, all substantially as described above. Purified GST/DNA-R (1–575) fusion protein bound to ELISA plates coated with calf thymus DNA (Magiwel, United Biotech, Mountain View, Calif.), as shown in FIG. 13. Mutagenesis of either cysteine 416 or 431 reduced DNA binding to approximately 50% of the level observed for wild-type GST/DNA-R fusion protein, strongly suggesting that this zinc finger domain is involved in specific DNA binding FIG. 13.

These results demonstrated that DNA binding by the soluble DNA-R fragment is not simply a nonspecific charge related interaction, but rather is mediated by specific a DNA-binding motifs in the protein, including at least the zinc finger motif.

EXAMPLE 5

Soluble DNA-R Protein Inhibits DNA-Induced Cytokine Secretion and Blocks Binding of DNA to Cells The presence of extracellular DNA in lung tissue of several chronic lung diseases, including cystic fibrosis, chronic bronchitis and bronchiectasis, causes or contributes to chronic inflammation of lung tissues with long-term pathological consequences. Extracellular DNA is known in the art to cause lung macrophages and other cells to release cytokines that mediate inflammation as part of the chronic symptomology of cystic fibrosis patients. As described in Example 2, the DNA-R protein of the invention is expressed in lung tissues, specifically in epithelial cells of the lung. This suggests that the DNA-R receptor protein of the invention is involved in inflammation by triggering the release of inflammation-causing cytokines. Thus, the ability of a soluble form of the DNA-R to bind DNA suggested that this protein fragment could compete for binding extracellular DNA in cystic fibrosis patients and would be useful thereby as a therapeutic agent.

To determine if the soluble DNA-R fragment of the invention inhibits DNA-induced cytokine secretion, soluble DNA-R protein was examined for inhibition of CF-DNA-induced IL-6 release from J774 murine monocyte/macrophage cells in culture. In the absence of stimulating DNA, DNA-R did not induce IL-6 secretion (shown in Table I). DNA isolated and purified from a patient with cystic fibrosis (CF DNA) induced 611 pg/mL of IL-6 from J774 cells. When CF DNA was incubated first with DNA-R protein (10 ng/mL) and then added to J774 cells, the amount of IL-6 was reduced by 36% in the presence of the soluble DNA-R protein (10 ng/mL). As a negative control, calf thymus DNA failed to induce detectable IL-6. To eliminate the possibility that cytokine release was caused by the presence of contaminating endotoxin, a Limulus amoebacyte assay was performed, and the CF DNA had <0.25 ng/mL of contaminating endotoxin. In control experiments, this amount of LPS induced only 4 pg/mL of IL-6. In the second experiment (also shown in Table 1), contaminating endotoxin was removed from the soluble DNA-R, permitting the use of increased DNA-R concentrations. Soluble DNA-R protein (used in the range 10 ng/mL–50 ng/mL) was incubated with J774 cells and 50 μg/mL of *E. coli* DNA. Cell-free supernatants were collected and IL-6 quantified by ELISA. In the absence of bacterial DNA soluble DNA-R did not induce IL-6 secretion. When bacterial DNA was added to the system, however, soluble DNA receptor protein inhibited IL-6 secretion in a dose-dependent manner (Table I).

TABLE I

| Stimulus | Treatment | IL-6 (pg/mL) | % Inhibition |
|---|---|---|---|
| — | Medium | 0 | — |
| — | DNA-R (10 ng/mL) | 0 | — |
| CF DNA (10 µg/mL) | Medium | 611 | — |
| CF DNA (10 µg/mL) | DNA-R (10 ng/mL) | 438 | 22 |
| E. coli (10 µg/mL) | Medium | 1467 | — |
| E. coli (10 µg/mL) | DNA-R (10 ng/mL) | 945 | 36 |
| E. coli (50 µg/mL) | Medium | 2390 ± 344 | — |
| E. coli (50 µg/mL) | DNA-R (10 ng/mL) | 1193 ± 128 | 50.1 |
| E. coli (50 µg/mL) | DNA-R (20 ng/mL) | 983 ± 212 | 58.9 |
| E. coli (50 µg/mL) | DNA-R (50 ng/mL) | 652 ± 76 | 72.7 |
| CT DNA[1] | Medium | 0 | — |
| LPS[2] | Medium | 4 | — |

[1] CT = calf thymus DNA
[2] LPS = bacterial lipopolysaccharide (endotoxin)

Figure 15:
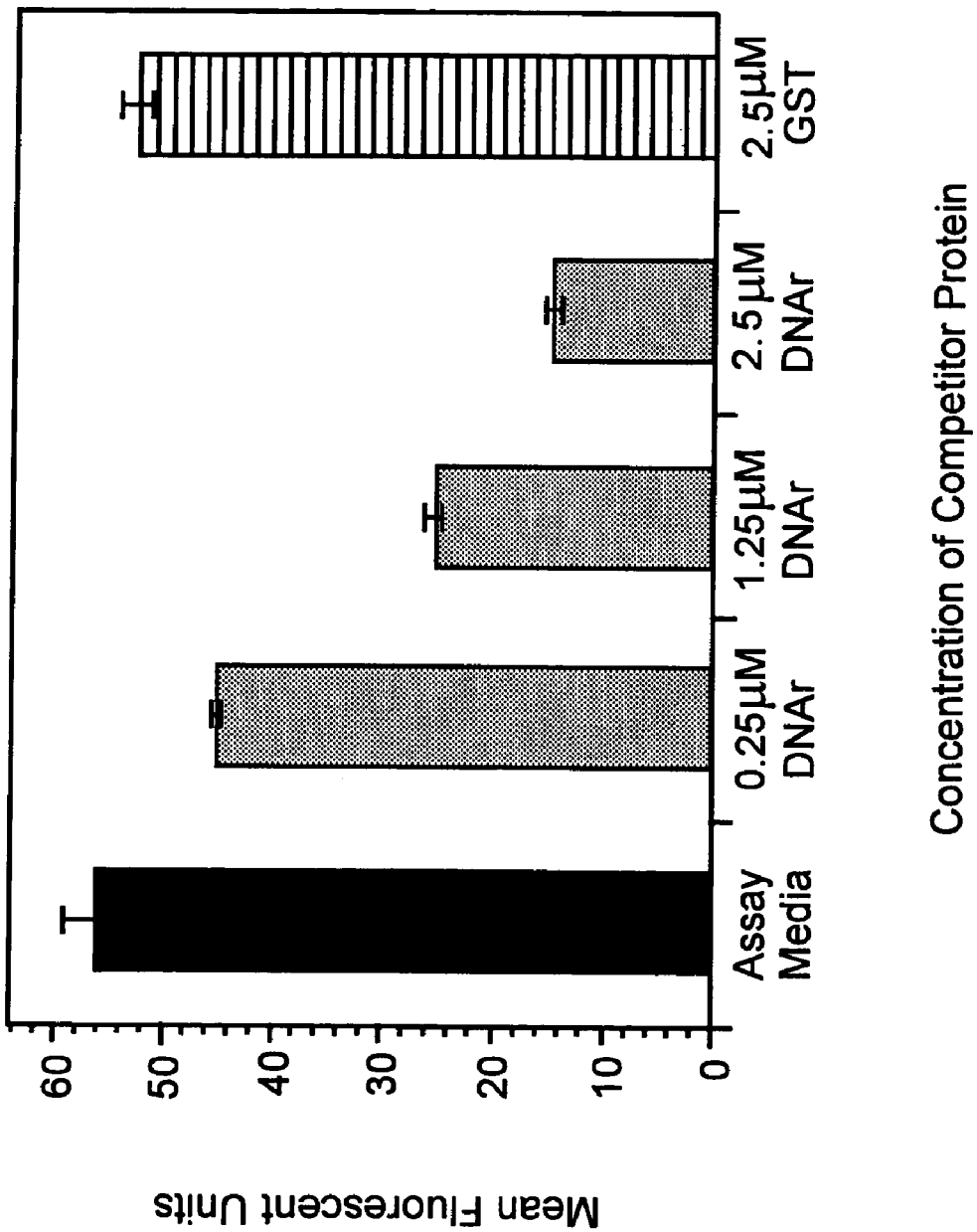
FIG. 15 illustrates competitive binding of plasmid DNA with soluble DNA-R. All samples have 0.25 nM (YOYO labeled) pGEM-DNA. The diagonal bars have varying amounts of soluble DNA-R added to block DNA binding. The horizontal line bar is control GST protein.

To determine whether soluble DNA-R protein fragment was capable of preventing DNA binding to cells, J774 cells (5×10$^5$ cells) and YOYO labeled pGEM-DNA were incubated with either the soluble DNA-R protein fragment or control GST protein. Cells were incubated for 30 minutes at 4° C., centrifuged and washed twice with assay media, resuspended and incubated with 7-amino actinomycin D (7AAD) on ice for 20 minutes in order to assess viability. The samples were assessed for DNA binding by FACScan (Becton-Dickinson, Franklin Lanes, N.J.). Results showed a dose-dependent inhibition of DNA binding to J774 cells (FIG. 15). Similar results were observed using human 293 cells. Additionally, the soluble DNA-R protein/DNA complex does not bind to the cell surface. The soluble DNA-R protein bound to DNA and is effective at preventing the association of DNA with the cell surface.

These results indicate that the soluble DNA-R fragment provided by this invention is useful for inhibiting cytokine release, and inflammation consequent thereto, by competitively binding either bacterial or mammalian extracellular DNA and reducing the amount of such DNA bound by cytokine-producing cells expressing the DNA-R of the invention.

EXAMPLE 6

DNA Binding to Cells Mediated by DNA-R

The experimental results disclosed above established that the soluble DNA-R fragment comprising amino acids 1–575 of the DNA-R of the invention was capable of binding DNA. Further experiments were performed to characterize DNA binding to the receptor, particularly whether the native receptor protein was capable of binding extracellular DNA at the cell surface, and whether binding is consistent with a receptor-mediated process.

In these experiments, A549 human lung carcinoma cells were harvested from log-phase cultures and treated with DNase and RNase to remove exogenous cell-surface bound nucleic acids. After treatment, the cells were washed with 10 mM EDTA and phosphate buffered saline (PBS) to stop the action of DNase and RNase. The cells were then plated in V-bottom 96-well plates at 10$^6$ cells/well in PBS containing 1% fetal calf serum (FCS) and 1 mM Ca$^{++}$Mg$^{++}$. YOYO-labeled pGEM4Z plasmid DNA was added at concentrations from 0–25 µg/mL in 0.2 mL media containing 1% FCS and 1 mM Ca$^{++}$Mg$^{++}$. The cells plus labeled plasmid were incubated for 30 minutes at 4° C., to minimize internalization of plasmid DNA. Upon completion of the 30 minute incubation, the cells were washed with 2× in PBS containing 1% FCS and 1 mM Ca$^{++}$Mg$^{++}$ and resuspended in 0.3 mL of PBS. Cells were then fixed in 1% formaldehyde and cell-surface binding of plasmid DNA quantified by FACS.

Figure 16:
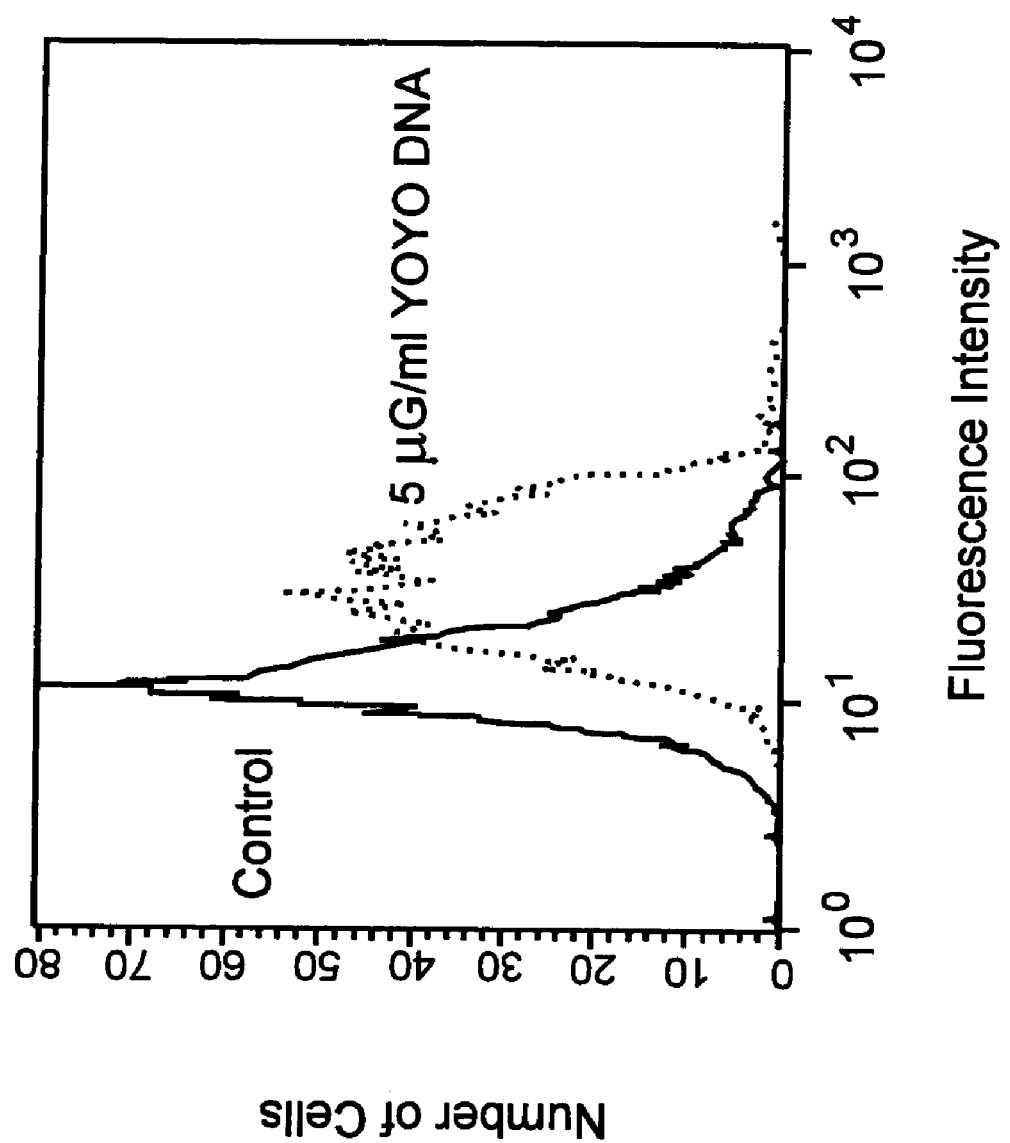
FIG. 16 are the results of fluorescence activated cell sorting (FACS) experiments illustrating cell-surface binding of YOYO labeled plasmid DNA in A549 cells. Cells were incubated in the presence (dashed line) and absence (solid line) of 5 µg/mL YOYO-labeled pGEM4Z DNA. The geometric mean fluorescence of untreated and treated cells is 13 and 34 respectively. The difference between the two values (21) is the increase in fluorescence intensity due to YOYO/pGEM4Z. This method of analysis is used for all YOYO/DNA binding analyses by FACS in subsequent figures.

The results of these experiments are shown in FIG. 16. This representative FACS histogram demonstrates the A549 cell profiles seen when comparing cells incubated with either medium (FIG. 16, curve on the left) or cells incubated with 5 µg/mL of YOYO/pGem4Z plasmid (FIG. 16, curve shifted to the right). The geometric mean of the intensity is used to describe the cell populations. In this example, the geometric mean of the A549 cell population, treated with medium only, was 13 and increased to 34 when incubated with YOYO-labeled plasmid DNA.

Figure 17A:
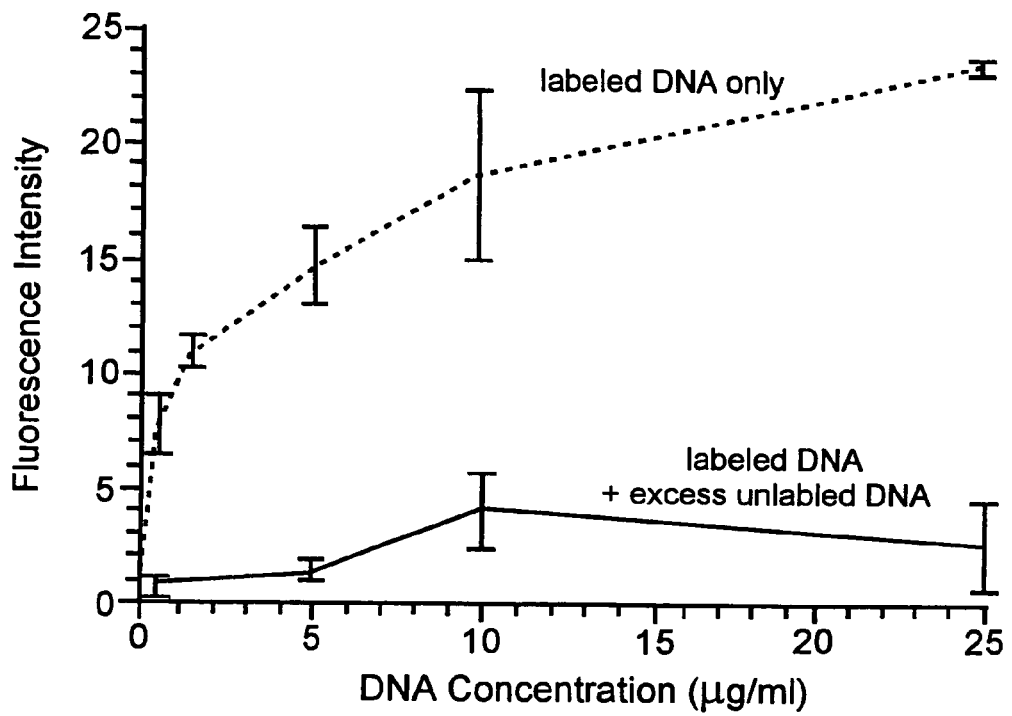
FIGS. 17A and 17B are the results of FACS analysis of YOYO labeled plasmid DNA binding to A549 cells in the presence of excess unlabeled DNA. Cell surface binding of YOYO/DNA to A549 cells.
Figure 17B:
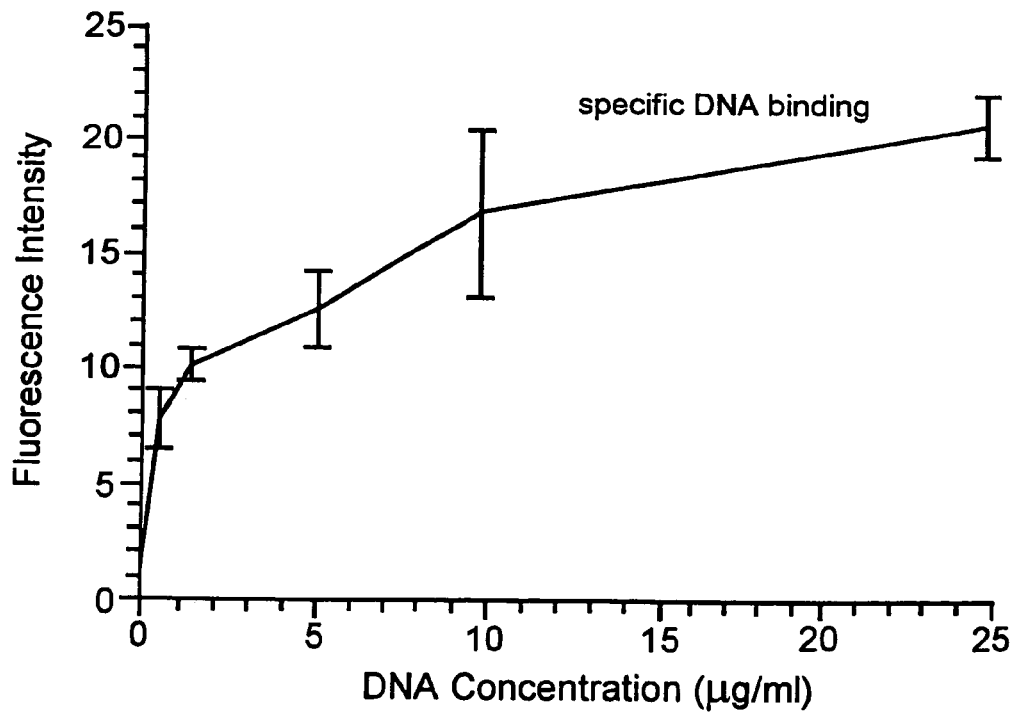

A binding curve for A549 cells was then generated using a range of plasmid DNA from 0–25 µg/mL (FIG. 17A and 17B). The Y-axis of the graph in FIG. 17A represents the geometric mean of the fluorescence intensity of the cell populations in the graph. Cell surface binding of plasmid DNA to A549 cells began to show saturation at approximately 10 µg/mL of DNA. Treatment of cells with a 25–100 fold excess of unlabeled DNA significantly blocked the binding of YOYO/DNA to the cell surface (FIG. 17A). The specific cell-surface binding to A549 cells, represented as the difference between total binding seen with excess unlabeled DNA, shows a binding curve with a characteristic saturation profile (FIG. 17B).

Also examined were the cell-surface plasmid DNA binding profiles for a variety of tumor cell lines, including B16 murine melanoma cells, MOLT-4 human lymphoblastic leukemia cells, and the human Raji Burkitt lymphoma cells. In all cells examined, cell-surface DNA saturable binding profiles were obtained, consistent with a receptor-mediated mechanism of binding. Under optimal DNA binding conditions the percent of cells in the population capable of binding DNA above the background level as detected by FACS, ranged from greater than 70% (S49, DHL-6, MOLT-4) to less than 10% (D10.S, HUT-78, K562 and G361).

TABLE II

| Cell Type | % Cells binding DNA | Lineage |
|---|---|---|
| S49 | 98 | Murine T-cell lymphoma |
| MOLT-4 | 79 | Human lymphoblastic leukemia |
| DHL-6 | 70 | Human B-cell |
| A549 | 55 | Human lung carcinoma |
| Dami | 44 | Human leukemia |
| B16 | 32 | Murine leukemia |
| B9 | 21 | Murine plasmacytoma |
| COS-7 | 20 | African green monkey kidney cell |
| HBE014 | 20 | Human bronchial epithelial cell |
| MO-7 | 16 | Human leukemia |
| NOR-10 | 16 | Murine muscle |
| J558 | 15 | Murine plasmacytoma |
| RAJI | 15 | Human Burkitt lymphoma |
| HeLa | 12 | Human cervical cancer |
| SW480 | 12 | Human colon adenocarcinoma |
| HUT-78 | 7 | Human cutaneous T-cell lymphoma |
| K562 | 5 | Human myelogenous leukemia |
| D10.S | 3 | Murine T cell |
| G361 | 3 | Human malignant melanoma |
| Spleen | 80 | Normal mouse spleen cells |

Figure 18:
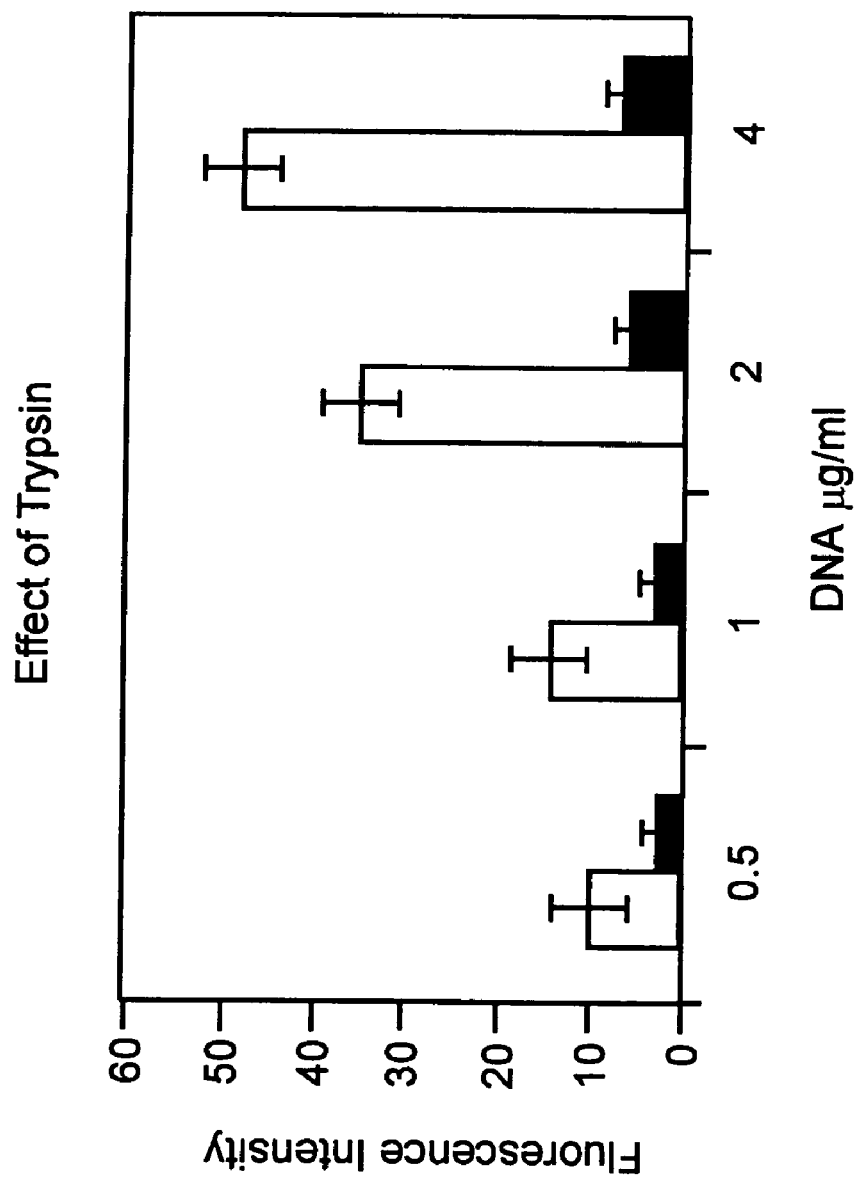
FIG. 18 shows the effects of trypsin treatment on DNA binding to A549 cells. A549 cells were incubated at 4° C. for 30 min with YOYO/pGEM4Z (0.5 to 4 µg/ml). After incubation the cells were washed (white bars) or trypsinized and washed (gray bars), then the fluorescence intensity was measured by FACS. The data are the mean±SD of triplicate determinations. Trypsin treatment was found to remove most cell-surface DNA binding.

To determine if DNA binding is mediated by a cell-surface protein, the experiments were performed substantially as described after cells were treated with trypsin. Cell-surface DNA-binding of plasmid DNA on A549 cells was significantly inhibited by treatment of cells with trypsin after binding with YOYO-labeled DNA at 4° C. (FIG. 18).

Figure 19:
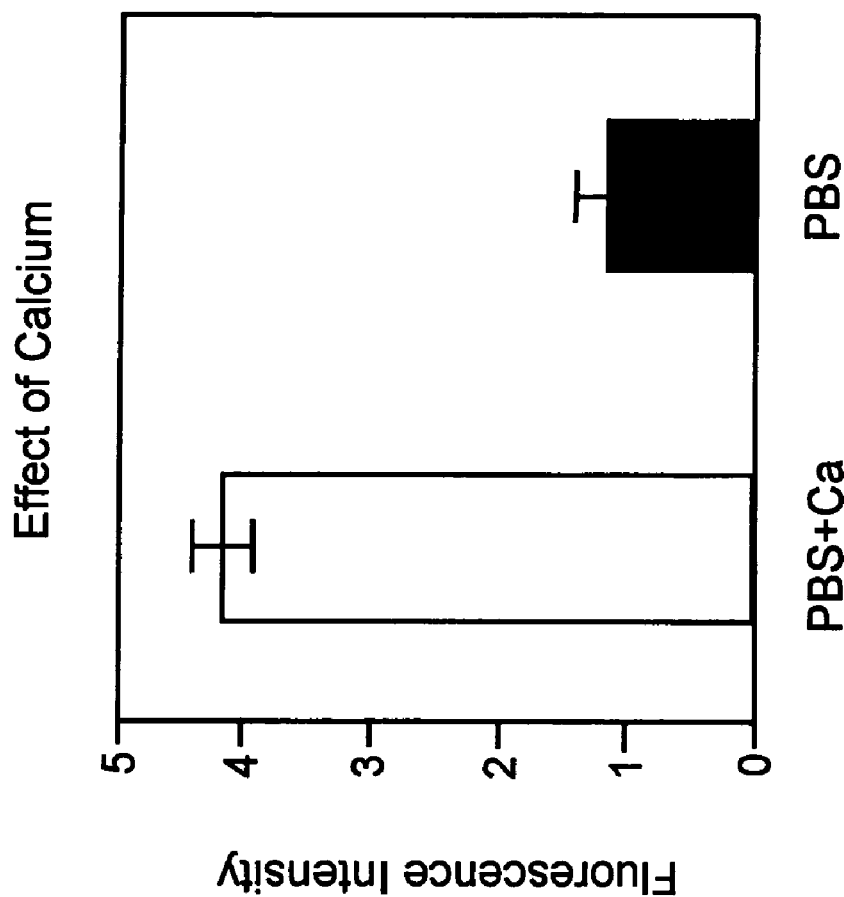
FIG. 19 shows the results of experiments indicating that DNA binding to the DNA-R of the receptor is calcium dependent. B16 cells were incubated with 1 µg/mL YOYO/pGEM4Z in PBS with (white bar) or without (gray bar) 1 mMCaCl$_2$, then the fluorescence intensity was measured by FACS. The data are mean±SD of triplicate measurements.

Finally, the effect of divalent cations on cell surface DNA binding was examined using B16 melanoma cells. These studies demonstrated a four-fold increase in fluorescence intensity when Ca$^{++}$ is added to the binding media (FIG. 19).

These results indicate that the DNA-R protein of the invention mediates cell surface binding of extracellular DNA in mammalian cells.

EXAMPLE 7

Internalization of Extracellular DNA into Cells Expressing DNA-R

The experiments described in Example 6 established that extracellular DNA was specifically bound to the DNA-R of the invention. Internalization of DNA into cells by the receptor was characterized using the following assay.

YOYO-labeled plasmid DNA was used to examine the kinetics of plasmid DNA internalization. The plasmid used in these assays was pEGFP-N1, encoding green fluorescent protein (Clontech, Palo Alto, Calif.). The assay required that cell surface binding of labeled DNA be distinguished from internalized plasmid DNA. This was accomplished by treatment of cells with trypsin to remove cell-surface proteins after incubation with plasmid DNA. This procedure permitted cell surface-bound plasmid DNA to be distinguished from internalized plasmid DNA, since trypsin treatment abolished cell surface bound DNA but not internalized plasmid DNA. In this assay, cells were plated in 24 well plates and incubated in culture media for 24 h. Media was then removed and various concentrations (0–25 µg/mL) of YOYO-labeled pEGFP-N1 plasmid DNA were added. The cells plus plasmid DNA were incubated for various times (0.5 to 5 hours) at 37° C. Thereafter, the media was removed, cells were treated with trypsin, washed, and then fixed with 1% formaldehyde. FACS analysis was used to quantify fluorescence intensity.

Figure 20:
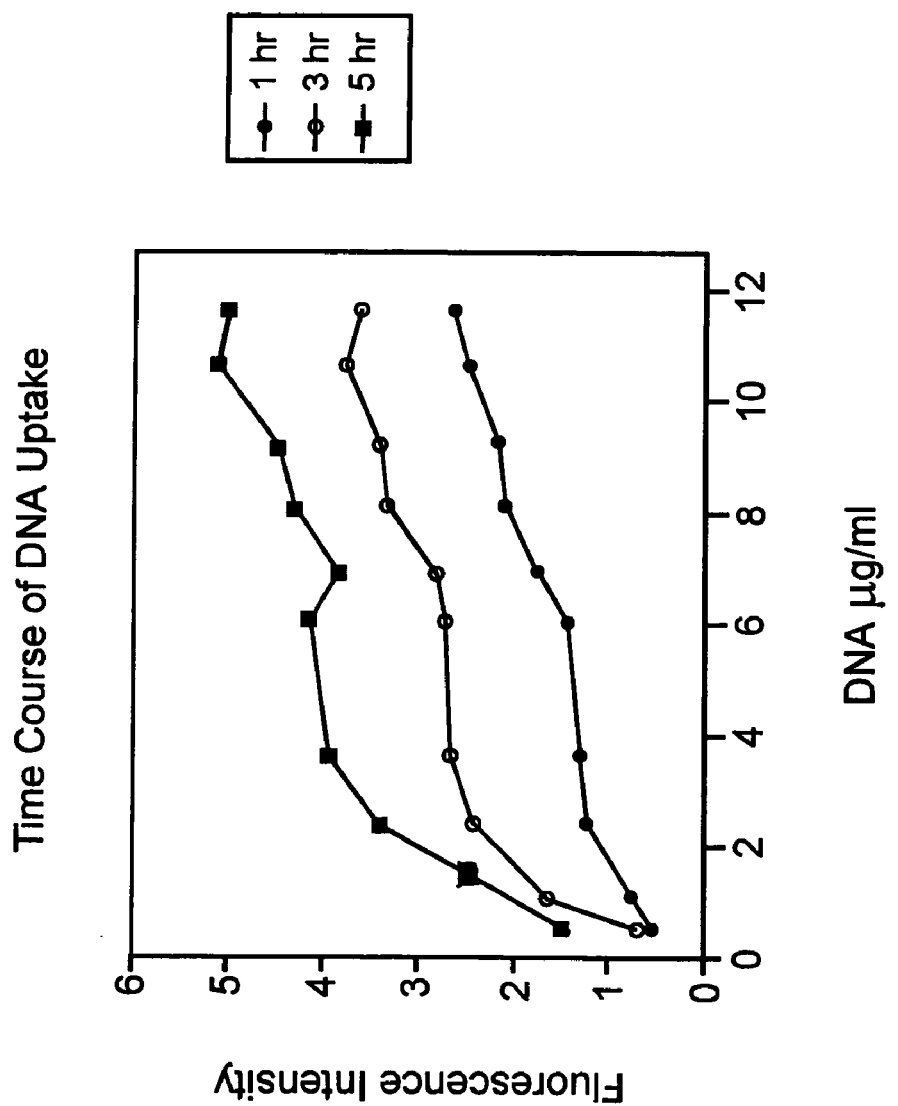
FIG. 20 shows a time course of plasmid DNA uptake by cells expressing the DNA-R of the invention. B16 cells were incubated at 37° C. with YOYO/pEGFP-N1 (0.6 to 12 µg/mL) for 1 hr (solid circles), 3 hr (open circles), or 5 hr (solid squares). The cells were then trypsinized to remove DNA bound to the cell-surface, and fluorescence intensity was measured by FACS.
Figure 21:
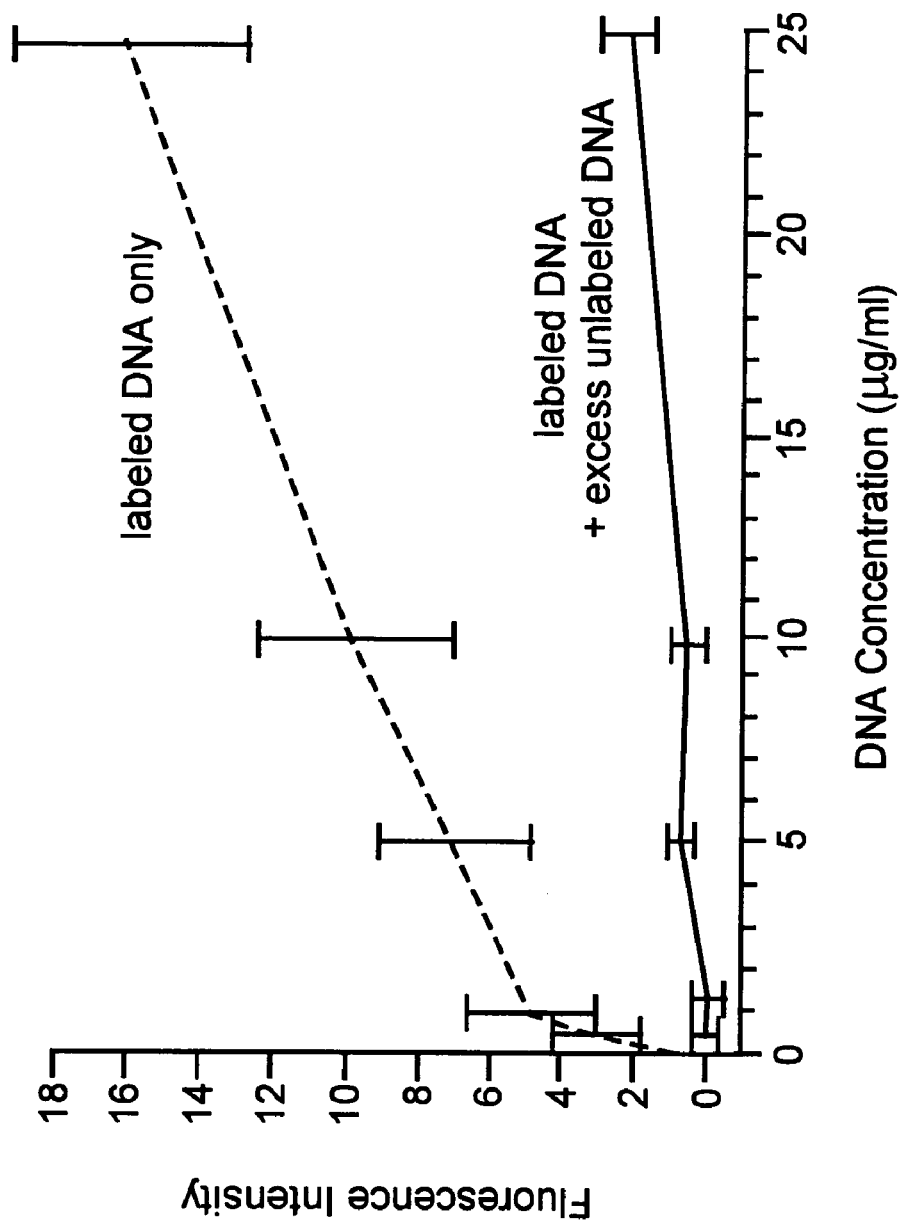
FIG. 21 shows that excess unlabeled DNA blocks internalization of YOYO/DNA by A549 cells. Cells were incubated for 2 hr at 37° C. with YOYO/pGEM4Z (1 to 25 µg/mL) in the presence (solid line) and absence (dashed line) of a 25- to 100-fold excess of calf thymus DNA. The cells were then washed and the fluorescence measured by FACS. Data are the mean±SEM of 5 experiments.

B16 murine melanoma cells were examined for internalization of YOYO/DNA using the above protocol after incubation for 1, 3, and 5 hours (FIG. 20). Internalization of pEGFP-N1 were found to be both dose- and time-dependent. An increasing amount of internalized plasmid DNA was seen with increasing dose of DNA and increasing time of incubation. Internalization of plasmid DNA by A549 cells was evaluated both with and without pre-treatment with unlabeled DNA. This assay was repeated with A549 cells, and similar results were obtained (FIG. 21). Moreover, pre-treatment of the A549 cells with a 25–100-fold excess of unlabeled calf thymus DNA significantly inhibited subsequent internalization of plasmid DNA (FIG. 21). Similar inhibition of internalization by pre-treatment of cells with excess unlabeled DNA was observed using a number of other cell lines (including B16, Raji, and MOLT-4). This demonstration of saturable DNA binding and internalization indicates that the cell-surface DNA receptor of the invention mediates internalization of extracellular plasmid DNA.

Figure 22:
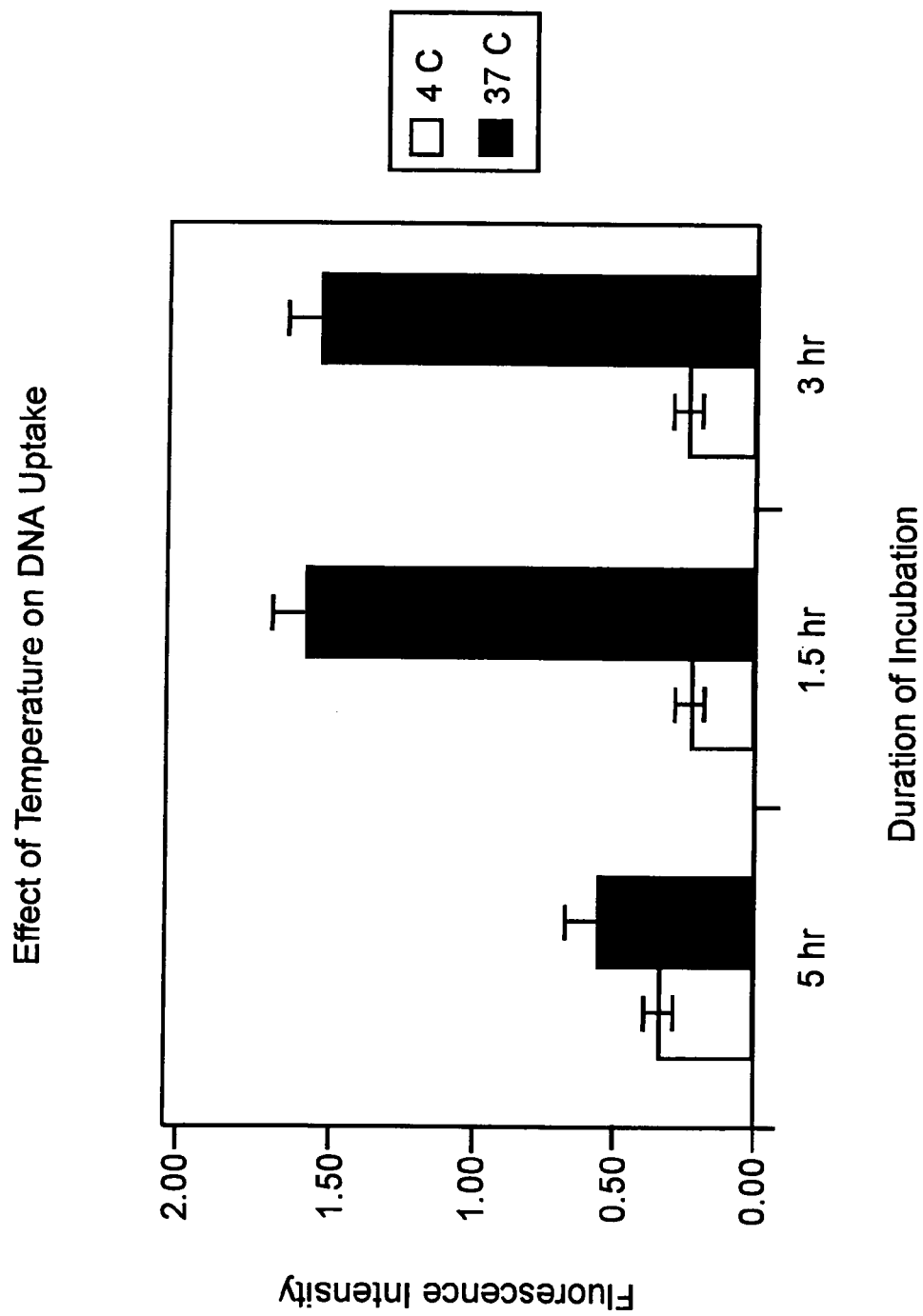
FIG. 22 illustrates that internalization of plasmid DNA in cells expressing the DNA-R of the invention is temperature dependent. B16 cells were incubated with YOYO/pGEM4Z (12 µg/mL) at 4° C. (white bars) or 37° C. (gray bars) for the indicated times. The cells were then trypsinized to remove cell-surface bound plasmid, washed, and the fluorescence measured by FACS. The data are the mean±SD of triplicate determinations.

Internalization of plasmid DNA was also observed to be a temperature-dependent process. Treatment of B16 cells at 4° C. significantly inhibited the amount of plasmid DNA that was internalized as compared to cells maintained at 37° C. (FIG. 22).

Figure 23A:
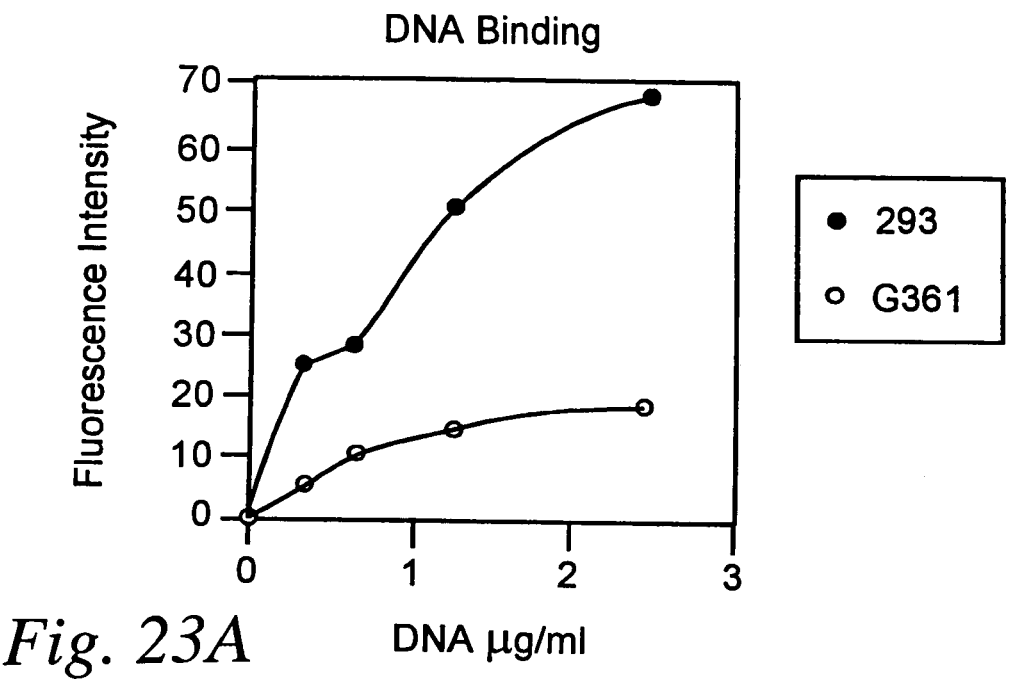
FIGS. 23A and 23B show that cell-surface DNA binding to the DNA-R of the invention is related to DNA uptake. 293 cells (solid circles) and G361 cells (open circles) were incubated for 3.5 hr with YOYO/pGEM4Z (at concentrations of from 0.3 to 2.5 µg/mL) at 4° C. for binding (FIG. 23A, left panel) or 37° C. for uptake (FIG. 23B, right panel).
Figure 23B:
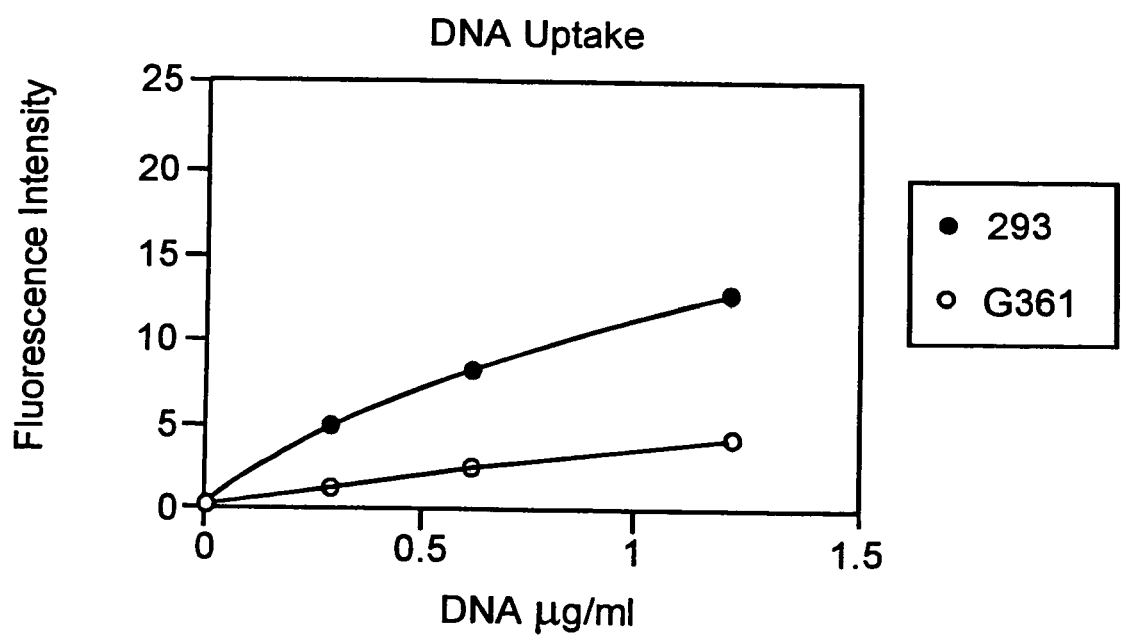

In order to ascertain whether the amount of DNA-R expressed on the cell surface influences the extent of extracellular DNA binding or DNA internalization, binding and internalization of plasmid DNA was compared in two cell lines: human melanoma G361 and the 293 human cell line. The G361 cells bound relatively low amounts of DNA, while 293 cells bound larger amounts of plasmid DNA as assessed by the cell-surface DNA binding assay (FIG. 23). Consistent with the binding results were the results obtained in these cells for DNA internalization, which showed that G361 cells internalized less plasmid DNA then 293 cells (FIG. 23). These data are consistent with identification of the DNA-R of the invention as a cell surface DNA receptor protein.

EXAMPLE 8

Gene Expression of DNA Internalized by DNA-R

Conditions for transgene expression using DNA internalized by the DNA-R of the invention were developed.

The experiments described above established plasmid DNA concentrations that saturated cell-surface binding. Used the pEGFP-N1 plasmid coding for green fluorescent protein (GFP), which was used because GFP remains exclusively intracellular. FACS analysis was used to quantify GFP expression. In this assay, cells ($1.25 \times 10^5$/well) were plated in 24-well plates and incubated overnight under mammalian cell culture conditions. On the next day, media was removed and the cells incubated for 3 hours at 37° C. in 5% $CO_2$ with plasmid DNA in 0.3 mL of growth medium. DNA was then removed and fresh medium added to the cells. In some cases 0.3 mL of growth medium was added to cells without removing the DNA. After 24–72 hours further incubation media was removed and cells washed once and then fixed with formaldehyde. Fluorescence intensity in the fixed cells was determined by FACS. However, no GFP expression was detected, even when using several different concentrations of pEGFP-N1 plasmid and incubation times. This result was consistently obtained, using a variety of cell lines (A459, B16, Raji), incubation times (24–72) hours), and ranges of plasmid DNA concentrations (0.1 to 100 µg/mL). This result was obtrained using cell lines that bind relatively higher levels of DNA on their cell-surface and those that bind lower levels of DNA. In positive controls, pEGFP-N1 plasmid was delivered by liposomes (Lipofectamine, Gibco-BRL, Gaithersburg, Md.) and resulted in significant GFP fluorescence within 24 hours. Representative data using the B16 cell incubated with either pEGFP-N1 alone or pEGFP-N1 delivered by liposomes shows the difference in GFP expression between these two techniques (FIG. 24).

In view of these results, the experiments were repeated with A549 cell in the presence of nocodazol, a microtubule inhibitor. Use of this inhibitor was indicated becausse one possible explanation of the unsuccessful experiments is that the DNA internalized by the DNA-R of the invention had been degraded, and nocodazol treatment was expected to reduce the extent of such degradation. Treatment of A549 cell with nocodazol prior to incubation with pEGFP-N1 resulted in a significant increase in expression of GFP as compared to cells that were not treated with nocodazol and incubated with pEGFP-N1 (FIG. 25). Cells which were not treated with nocodazol failed to demonstrate detectable expression of GFP (FIG. 25).

These results indicated that uptake of extracellular DNA mediated by the DNA-R of the invention required additional treatment to result in expression of genes encoded therein, and the above assay provides a prototype of assays for identifying such compounds. In these assays, an amount of GFP-encoding plasmid DNA known to reliably produce detectable GFP expression is contacted with a mammalian cell expression the DNA-R of the invention at levels known to mediate efficient uptake of extracellular DNA. GFP gene expression is then assayed in the presence and absence of a test compound to detect increased gene expression in the presence of the compound.

It should be understood that the foregoing disclosure emphasizes certain specific embodiments of the invention and that all modifications or alternatives equivalent thereto are within the spirit and scope of the invention as set forth in the appended claims.

We claim:

1. An isolated homogenous composition of a mammalian cell surface DNA receptor (DNA-R) or a DNA-binding fragment thereof, wherein the DNA-R comprises the amino acid sequence identified by SEQ ID No.:2 and wherein the DNA-binding fragment comprises amino acids 575 of SEQ ID No.:2.

2. An isolated homogenous composition of a DNA-binding fragment of a mammalian cell surface DNA receptor (DNA-R) comprising the amino acid sequence identified by amino acids 1–575 of SEQ ID No.:2.

3. An isolated homogenous composition of a soluble mammalian cell surface DNA receptor (DNA-R) comprising the amino acid sequence identified by SEQ ID No.:2 wherein amino acids 1133–1171 are deleted therefrom.

* * * * *